(12) United States Patent
Bruce et al.

(10) Patent No.: US 8,173,363 B2
(45) Date of Patent: May 8, 2012

(54) **RANDOM TRANSPOSON INSERTION IN *STAPHYLOCOCCUS AUREUS* AND USE THEREOF TO IDENTIFY ESSENTIAL GENES**

(75) Inventors: Kim Folger Bruce, Seattle, WA (US); Paul Warrener, Seattle, WA (US); Jennifer McLarnan, Everett, WA (US); Kevin Hou, Issaquah, WA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 792 days.

(21) Appl. No.: 10/525,062

(22) PCT Filed: Aug. 20, 2003
(Under 37 CFR 1.47)

(86) PCT No.: PCT/US03/25879
§ 371 (c)(1),
(2), (4) Date: Mar. 9, 2006

(87) PCT Pub. No.: WO2004/018624
PCT Pub. Date: Mar. 4, 2004

(65) Prior Publication Data
US 2006/0234233 A1    Oct. 19, 2006

Related U.S. Application Data

(60) Provisional application No. 60/404,406, filed on Aug. 20, 2002.

(51) Int. Cl.
*C12Q 1/68* (2006.01)
*C07H 21/04* (2006.01)
*G01N 33/48* (2006.01)

(52) U.S. Cl. ............ 435/6; 536/23.1; 536/24.1; 702/19; 702/20

(58) Field of Classification Search .................. None
See application file for complete search history.

(56) References Cited

U.S. PATENT DOCUMENTS
5,876,931 A    3/1999  Holden
5,962,222 A   10/1999  Kaderbhai FOREIGN PATENT DOCUMENTS
WO    WO 01/07651 A2    2/2001
WO    WO 01/70955 A2    9/2001

OTHER PUBLICATIONS

Karlyshev et al., BioTechniques, vol. 28, pp. 1078-1082, Jun. 2000.*
O'Toole, G.A., et al., "Initiation of Biofilm Formation in Pseudomonas Fluorescens WCS365 Proceeds Via Multiple, Convergent Signalling Pathways: A Genetic Analysis Molecular Microbiology," 28(3): 449-461 (1998).
Supplementary Partial European Search Report, mailed on Jun. 28, 2007, in counterpart European Patent Application No. 03770240.4.
Kuroda, M. et al., "Whole Genome Sequencing of Meticillin-Resistant *Staphylococcus aureus*," Lancet, vol. 357: 1225-1240 London, GB (2001).
Yinduo, J. et al., "Identification of Critical *Staphylococcal* Genes Using Conditional Phenotypes Generated by Antisense RNA," Science, vol. 293: 2266-2269, Washington D.C (2001).
Mingming, X. et al., "Rapid Method for the Identification of Essential Genes in *Staphylococcus aureus*," Plasmid, vol. 42: 144-149 (1999).
Fan et al.; (2001) "Regulated Ectopic Expression and Allelic-Replacement Mutagenesis as a Method for gene Essentiality Testing *Staphylococcus aureus*"; Source: Academic Press, Plasmid 46, pp. 71-75, doi:10.1006/plas.2001.1526, available online at http://www.academicpress.com.
Forsyth et al.; (2002) "A genome-wide strategy for the identification of essential genes in *Staphylococcus aureus*"; Source: Molecular Microbiology, vol. 43, No. 6, pp. 1387-1400.
Judson and Mekalanos; (Nov. 2000) "Transposon-based approaches to identify essential bacterial genes" Source: Trends in Microbiology, vol. 8, No. 11, pp. 521-526.
Zhang et al.; (2000) "Regulated gene expression in *Staphylococcus aureus* for identifying conditional lethal phenotypes and antibiotic mode of action"; Source: Gene, 255, pp. 297-305.

* cited by examiner

*Primary Examiner* — Shubo Zhou
(74) *Attorney, Agent, or Firm* — Banner & Witcoff, Ltd.

(57) ABSTRACT

The invention provides a method for generating a database of candidate essential genes in *Staphylococcus aureus*, as well as otherwise important genes that, when mutated, lead to a growth attenuated phenotype. Such genes and mutants of such genes are important for identifying antibacterial agents suitable for treating and preventing *S. aureus* infections. The invention includes methods for confirming the essentiality or importance of candidate genes, as well as methods for utilizing those genes to screen for new antibacterial drugs. The invention also includes the antibacterial agents identified using the disclosed methods, as well as methods of using the same for treating and preventing *Staphylococcus* infection.

14 Claims, 14 Drawing Sheets

Single-crossover recombination

Promoter Swap

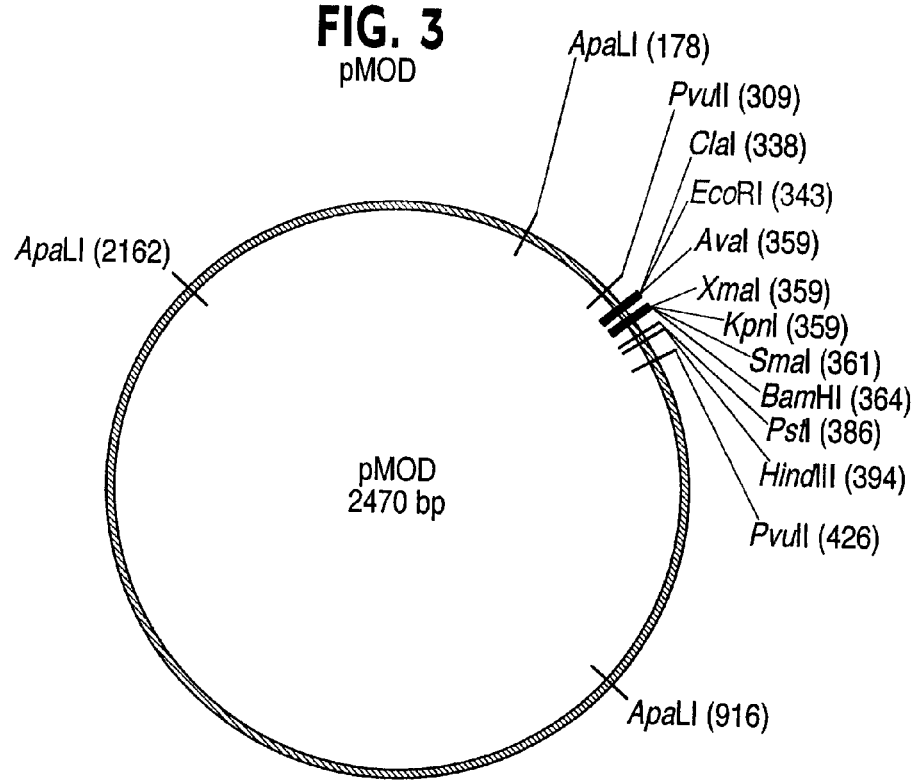

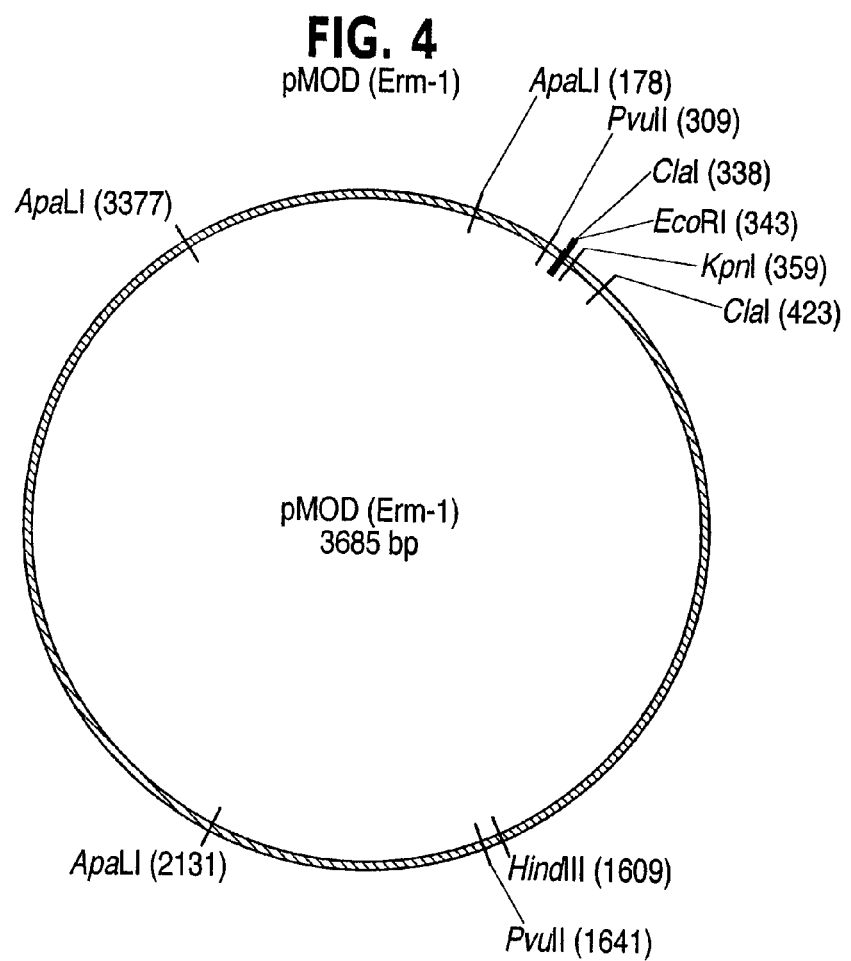

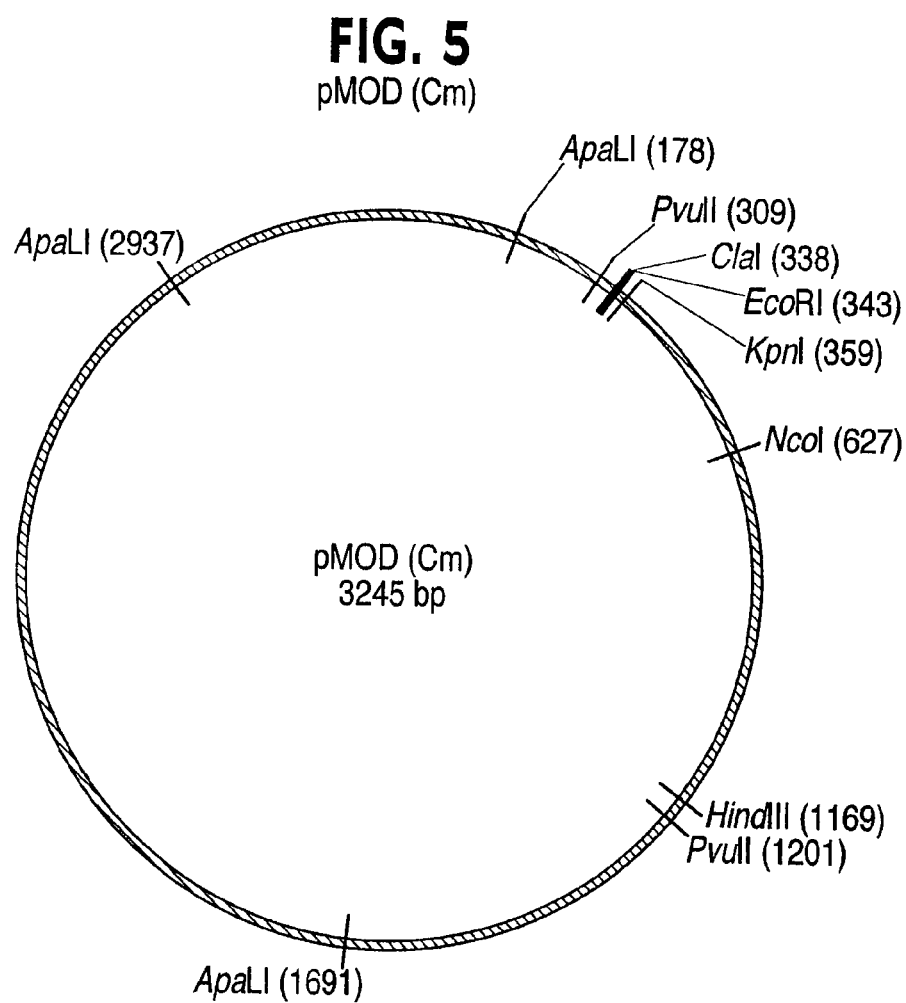

FIG. 6A pMOD

```
  1  TCGCGCGTTT  CGGTGATGAC  GGTGAAAACC  TCTGACACAT  GCAGCTCCCG
     AGCGCGCAAA  GCCACTACTG  CCACTTTTGG  AGACTGTGTA  CGTCGAGGGC
 51  GAGACGGTCA  CAGCTTGTCT  GTAAGCGGAT  GCCGGGAGCA  GACAAGCCCG
     CTCTGCCAGT  GTCGAACAGA  CATTCGCCTA  CGGCCCTCGT  CTGTTCGGGC
101  TCAGGGCGCG  TCAGCGGGTG  TTGGCGGGTG  TCGGGGCTGG  CTTAACTATG
     AGTCCCGCGC  AGTCGCCCAC  AACCGCCCAC  AGCCCCGACC  GAATTGATAC
                                         ApaLI
151  CGGCATCAGA  GCAGATTGTA  CTGAGAGTGC  ACCATATGCG  GTGTGAAATA
     GCCGTAGTCT  CGTCTAACAT  GACTCTCACG  TGGTATACGC  CACACTTTAT
201  CCGCACAGAT  GCGTAAGGAG  AAAATACCGC  ATCAGGCGCC  ATTCGCCATT
     GGCGTGTCTA  CGCATTCCTC  TTTTATGGCG  TAGTCCGCGG  TAAGCGGTAA
251  CAGGCTGCGC  AACTGTTGGG  AAGGGCGATC  GGTGCGGGCC  TCTTCGCTAT
     GTCCGACGCG  TTGACAACCC  TTCCCGCTAG  CCACGCCCGG  AGAAGCGATA
                                                    EcoRI
        PvuII                                       ClaI
301  TACGCCAGCT  GTCTCTTATA  CACATCTCAA  CCATCATCGA  TGAATTCGAG
     ATGCGGTCGA  CAGAGAATAT  GTGTAGAGTT  GGTAGTAGCT  ACTTAAGCTC
      KpnI       BamHI
         SmaI
          XmaI
           AvaI                           PstI       HindIII
351  CTCGGTACCC  GGGGATCCTC  TAGAGTCGAC  CTGCAGGCAT  GCAAGCTTCA
     GAGCCATGGG  CCCCTAGGAG  ATCTCAGCTG  GACGTCCGTA  CGTTCGAAGT
                             PvuII
401  GGGTTGAGAT  GTGTATAAGA  GACAGCTGCA  TTAATGAATC  GGCCAACGCG
     CCCAACTCTA  CACATATTCT  CTGTCGACGT  AATTACTTAG  CCGGTTGCGC
451  CGGGGAGAGG  CGGTTTGCGT  ATTGGGCGCT  CTTCCGCTTC  CTCGCTCACT
     GCCCCTCTCC  GCCAAACGCA  TAACCCGCGA  GAAGGCGAAG  GAGCGAGTGA
501  GACTCGCTGC  GCTCGGTCGT  TCGGCTGCGG  CGAGCGGTAT  CAGCTCACTC
     CTGAGCGACG  CGAGCCAGCA  AGCCGACGCC  GCTCGCCATA  GTCGAGTGAG
551  AAAGGCGGTA  ATACGGTTAT  CCACAGAATC  AGGGGATAAC  GCAGGAAAGA
     TTTCCGCCAT  TATGCCAATA  GGTGTCTTAG  TCCCCTATTG  CGTCCTTTCT
601  ACATGTGAGC  AAAAGGCCAG  CAAAAGGCCA  GGAACCGTAA  AAAGGCCGCG
     TGTACACTCG  TTTTCCGGTC  GTTTTCCGGT  CCTTGGCATT  TTTCCGGCGC
651  TTGCTGGCGT  TTTTCCATAG  GCTCCGCCCC  CCTGACGAGC  ATCACAAAAA
     AACGACCGCA  AAAAGGTATC  CGAGGCGGGG  GGACTGCTCG  TAGTGTTTTT
701  TCGACGCTCA  AGTCAGAGGT  GGCGAAACCC  GACAGGACTA  TAAAGATACC
     AGCTGCGAGT  TCAGTCTCCA  CCGCTTTGGG  CTGTCCTGAT  ATTTCTATGG
751  AGGCGTTTCC  CCCTGGAAGC  TCCCTCGTGC  GCTCTCCTGT  TCCGACCCTG
     TCCGCAAAGG  GGGACCTTCG  AGGGAGCACG  CGAGAGGACA  AGGCTGGGAC
801  CCGCTTACCG  GATACCTGTC  CGCCTTTCTC  CCTTCGGGAA  GCGTGGCGCT
     GGCGAATGGC  CTATGGACAG  GCGGAAAGAG  GGAAGCCCTT  CGCACCGCGA
851  TTCTCATAGC  TCACGCTGTA  GGTATCTCAG  TTCGGTGTAG  GTCGTTCGCT
     AAGAGTATCG  AGTGCGACAT  CCATAGAGTC  AAGCCACATC  CAGCAAGCGA
                         ApaLI
901  CCAAGCTGGG  CTGTGTGCAC  GAACCCCCCG  TTCAGCCCGA  CCGCTGCGCC
     GGTTCGACCC  GACACACGTG  CTTGGGGGGC  AAGTCGGGCT  GGCGACGCGG
```

FIG. 6B
pMOD

```
 951  TTATCCGGTA  ACTATCGTCT  TGAGTCCAAC  CCGGTAAGAC  ACGACTTATC
      AATAGGCCAT  TGATAGCAGA  ACTCAGGTTG  GGCCATTCTG  TGCTGAATAG
1001  GCCACTGGCA  GCAGCCACTG  GTAACAGGAT  TAGCAGAGCG  AGGTATGTAG
      CGGTGACCGT  CGTCGGTGAC  CATTGTCCTA  ATCGTCTCGC  TCCATACATC
1051  GCGGTGCTAC  AGAGTTCTTG  AAGTGGTGGC  CTAACTACGG  CTACACTAGA
      CGCCACGATG  TCTCAAGAAC  TTCACCACCG  GATTGATGCC  GATGTGATCT
1101  AGGACAGTAT  TTGGTATCTG  CGCTCTGCTG  AAGCCAGTTA  CCTTCGGAAA
      TCCTGTCATA  AACCATAGAC  GCGAGACGAC  TTCGGTCAAT  GGAAGCCTTT
1151  AAGAGTTGGT  AGCTCTTGAT  CCGGCAAACA  AACCACCGCT  GGTAGCGGTG
      TTCTCAACCA  TCGAGAACTA  GGCCGTTTGT  TTGGTGGCGA  CCATCGCCAC
1201  GTTTTTTTGT  TTGCAAGCAG  CAGATTACGC  GCAGAAAAAA  AGGATCTCAA
      CAAAAAAACA  AACGTTCGTC  GTCTAATGCG  CGTCTTTTTT  TCCTAGAGTT
1251  GAAGATCCTT  TGATCTTTTC  TACGGGGTCT  GACGCTCAGT  GGAACGAAAA
      CTTCTAGGAA  ACTAGAAAAG  ATGCCCCAGA  CTGCGAGTCA  CCTTGCTTTT
1301  CTCACGTTAA  GGGATTTTGG  TCATGAGATT  ATCAAAAAGG  ATCTTCACCT
      GAGTGCAATT  CCCTAAAACC  AGTACTCTAA  TAGTTTTTCC  TAGAAGTGGA
1351  AGATCCTTTT  AAATTAAAAA  TGAAGTTTTA  AATCAATCTA  AAGTATATAT
      TCTAGGAAAA  TTTAATTTTT  ACTTCAAAAT  TTAGTTAGAT  TTCATATATA
1401  GAGTAAACTT  GGTCTGACAG  TTACCAATGC  TTAATCAGTG  AGGCACCTAT
      CTCATTTGAA  CCAGACTGTC  AATGGTTACG  AATTAGTCAC  TCCGTGGATA
1451  CTCAGCGATC  TGTCTATTTC  GTTCATCCAT  AGTTGCCTGA  CTCCCCGTCG
      GAGTCGCTAG  ACAGATAAAG  CAAGTAGGTA  TCAACGGACT  GAGGGGCAGC
1501  TGTAGATAAC  TACGATACGG  GAGGGCTTAC  CATCTGGCCC  CAGTGCTGCA
      ACATCTATTG  ATGCTATGCC  CTCCCGAATG  GTAGACCGGG  GTCACGACGT
1551  ATGATACCGC  GAGACCCACG  CTCACCGGCT  CCAGATTTAT  CAGCAATAAA
      TACTATGGCG  CTCTGGGTGC  GAGTGGCCGA  GGTCTAAATA  GTCGTTATTT
1601  CCAGCCAGCC  GGAAGGGCCG  AGCGCAGAAG  TGGTCCTGCA  ACTTTATCCG
      GGTCGGTCGG  CCTTCCCGGC  TCGCGTCTTC  ACCAGGACGT  TGAAATAGGC
1651  CCTCCATCCA  GTCTATTAAT  TGTTGCCGGG  AAGCTAGAGT  AAGTAGTTCG
      GGAGGTAGGT  CAGATAATTA  ACAACGGCCC  TTCGATCTCA  TTCATCAAGC
1701  CCAGTTAATA  GTTTGCGCAA  CGTTGTTGCC  ATTGCTACAG  GCATCGTGGT
      GGTCAATTAT  CAAACGCGTT  GCAACAACGG  TAACGATGTC  CGTAGCACCA
1751  GTCACGCTCG  TCGTTTGGTA  TGGCTTCATT  CAGCTCCGGT  TCCCAACGAT
      CAGTGCGAGC  AGCAAACCAT  ACCGAAGTAA  GTCGAGGCCA  AGGGTTGCTA
1801  CAAGGCGAGT  TACATGATCC  CCCATGTTGT  GCAAAAAAGC  GGTTAGCTCC
      GTTCCGCTCA  ATGTACTAGG  GGGTACAACA  CGTTTTTTCG  CCAATCGAGG
1851  TTCGGTCCTC  CGATCGTTGT  CAGAAGTAAG  TTGGCCGCAG  TGTTATCACT
      AAGCCAGGAG  GCTAGCAACA  GTCTTCATTC  AACCGGCGTC  ACAATAGTGA
1901  CATGGTTATG  GCAGCACTGC  ATAATTCTCT  TACTGTCATG  CCATCCGTAA
      GTACCAATAC  CGTCGTGACG  TATTAAGAGA  ATGACAGTAC  GGTAGGCATT
1951  GATGCTTTTC  TGTGACTGGT  GAGTACTCAA  CCAAGTCATT  CTGAGAATAG
      CTACGAAAAG  ACACTGACCA  CTCATGAGTT  GGTTCAGTAA  GACTCTTATC
2001  TGTATGCGGC  GACCGAGTTG  CTCTTGCCCG  GCGTCAATAC  GGGATAATAC
      ACATACGCCG  CTGGCTCAAC  GAGAACGGGC  CGCAGTTATG  CCCTATTATG
2051  CGCGCCACAT  AGCAGAACTT  TAAAAGTGCT  CATCATTGGA  AAACGTTCTT
      GCGCGGTGTA  TCGTCTTGAA  ATTTTCACGA  GTAGTAACCT  TTTGCAAGAA
2101  CGGGGCGAAA  ACTCTCAAGG  ATCTTACCGC  TGTTGAGATC  CAGTTCGATG
      GCCCCGCTTT  TGAGAGTTCC  TAGAATGGCG  ACAACTCTAG  GTCAAGCTAC
```

FIG. 6C

```
                      ApaLI           pMOD
2151  TAACCCACTC  GTGCACCCAA  CTGATCTTCA  GCATCTTTTA  CTTTCACCAG
      ATTGGGTGAG  CACGTGGGTT  GACTAGAAGT  CGTAGAAAAT  GAAAGTGGTC
2201  CGTTTCTGGG  TGAGCAAAAA  CAGGAAGGCA  AAATGCCGCA  AAAAAGGGAA
      GCAAAGACCC  ACTCGTTTTT  GTCCTTCCGT  TTTACGGCGT  TTTTTCCCTT
2251  TAAGGGCGAC  ACGGAAATGT  TGAATACTCA  TACTCTTCCT  TTTTCAATAT
      ATTCCCGCTG  TGCCTTTACA  ACTTATGAGT  ATGAGAAGGA  AAAAGTTATA
2301  TATTGAAGCA  TTTATCAGGG  TTATTGTCTC  ATGAGCGGAT  ACATATTTGA
      ATAACTTCGT  AAATAGTCCC  AATAACAGAG  TACTCGCCTA  TGTATAAACT
2351  ATGTATTTAG  AAAAATAAAC  AAATAGGGGT  TCCGCGCACA  TTTCCCCGAA
      TACATAAATC  TTTTTATTTG  TTTATCCCCA  AGGCGCGTGT  AAAGGGGCTT
2401  AAGTGCCACC  TGACGTCTAA  GAAACCATTA  TTATCATGAC  ATTAACCTAT
      TTCACGGTGG  ACTGCAGATT  CTTTGGTAAT  AATAGTACTG  TAATTGGATA
2451  AAAAATAGGC  GTATCACGAG
      TTTTTATCCG  CATAGTGCTC
```

FIG. 7A
pMOD (Erm-1)

```
   1  TCGCGCGTTT  CGGTGATGAC  GGTGAAAACC  TCTGACACAT  GCAGCTCCCG
      AGCGCGCAAA  GCCACTACTG  CCACTTTTGG  AGACTGTGTA  CGTCGAGGGC
  51  GAGACGGTCA  CAGCTTGTCT  GTAAGCGGAT  GCCGGGAGCA  GACAAGCCCG
      CTCTGCCAGT  GTCGAACAGA  CATTCGCCTA  CGGCCCTCGT  CTGTTCGGGC
 101  TCAGGGCGCG  TCAGCGGGTG  TTGGCGGGTG  TCGGGGCTGG  CTTAACTATG
      AGTCCCGCGC  AGTCGCCCAC  AACCGCCCAC  AGCCCCGACC  GAATTGATAC
                                             ApaLI
 151  CGGCATCAGA  GCAGATTGTA  CTGAGAGTGC  ACCATATGCG  GTGTGAAATA
      GCCGTAGTCT  CGTCTAACAT  GACTCTCACG  TGGTATACGC  CACACTTTAT
 201  CCGCACAGAT  GCGTAAGGAG  AAAATACCGC  ATCAGGCGCC  ATTCGCCATT
      GGCGTGTCTA  CGCATTCCTC  TTTTATGGCG  TAGTCCGCGG  TAAGCGGTAA
 251  CAGGCTGCGC  AACTGTTGGG  AAGGGCGATC  GGTGCGGGCC  TCTTCGCTAT
      GTCCGACGCG  TTGACAACCC  TTCCCGCTAG  CCACGCCCGG  AGAAGCGATA
              PvuII                            ClaI        EcoRI
 301  TACGCCAGCT  GTCTCTTATA  CACATCTCAA  CCATCATCGA  TGAATTCGAG
      ATGCGGTCGA  CAGAGAATAT  GTGTAGAGTT  GGTAGTAGCT  ACTTAAGCTC
           KpnI
 351  CTCGGTACCG  TACCATTCAA  ATTTATCCTT  ATTGTACAAA  ATAACAGCGA
      GAGCCATGGC  ATGGTAAGTT  TAAATAGGAA  TAACATGTTT  TATTGTCGCT
                                  ClaI
 401  AATTTTTAAA  TCTATTCCTT  ATCGATACAA  ATTCCCCGTA  GGCGCTAGGG
      TTAAAAATTT  AGATAAGGAA  TAGCTATGTT  TAAGGGGCAT  CCGCGATCCC
 451  ACCTCTTTAG  CTCCTTGGAA  GCTGTCAGTA  GTATACCTAA  TAATTTATCT
      TGGAGAAATC  GAGGAACCTT  CGACAGTCAT  CATATGGATT  ATTAAATAGA
 501  ACATTCCCTT  TAGTAACGTG  TAACTTTCCA  AATTTACAAA  AGCGACTCAT
      TGTAAGGGAA  ATCATTGCAC  ATTGAAAGGT  TTAAATGTTT  TCGCTGAGTA
 551  AGAATTATTT  CCTCCCGTTA  AATAATAGAT  AACTATTAAA  AATAGACAAT
      TCTTAATAAA  GGAGGGCAAT  TTATTATCTA  TTGATAATTT  TTATCTGTTA
 601  ACTTGCTCAT  AAGTAACGGT  ACTTAAATTG  TTTACTTTGG  CGTGTTTCAT
      TGAACGAGTA  TTCATTGCCA  TGAATTTAAC  AAATGAAACC  GCACAAAGTA
 651  TGCTTGTGAA  ACTGATTTTT  AGTAAACAGT  TGACGATATT  CTCGATTGAC
      ACGAACACTT  TGACTAAAAA  TCATTTGTCA  ACTGCTATAA  GAGCTAACTG
 701  CCATTTTGAA  ACAAAGTACG  TATATAGCTT  CCAATATTTA  TCTGGAACAT
      GGTAAAACTT  TGTTTCATGC  ATATATCGAA  GGTTATAAAT  AGACCTTGTA
 751  CTGTGGTATG  GCGGGTAAGT  TTTATTAAGA  CACTGTTTAC  TTTTGGTTTA
      GACACCATAC  CGCCCATTCA  AAATAATTCT  GTGACAAATG  AAAACCAAAT
 801  GGATGAAAGC  ATTCCGCTGG  CAGCTTAAGC  AATTGCTGAA  TCGAGACTTG
      CCTACTTTCG  TAAGGCGACC  GTCGAATTCG  TTAACGACTT  AGCTCTGAAC
 851  AGTGTGCAAG  AGCAACCCTA  GTGTTCGGTG  AATATCCAAG  GTACGCTTGT
      TCACACGTTC  TCGTTGGGAT  CACAAGCCAC  TTATAGGTTC  CATGCGAACA
 901  AGAATCCTTC  TTCAACAATC  AGATAGATGT  CAGACGCATG  GCTTTCAAAA
      TCTTAGGAAG  AAGTTGTTAG  TCTATCTACA  GTCTGCGTAC  CGAAAGTTTT
 951  ACCACTTTTT  TAATAATTTG  TGTGCTTAAA  TGGTAAGGAA  TATTCCCAAC
      TGGTGAAAAA  ATTATTAAAC  ACACGAATTT  ACCATTCCTT  ATAAGGGTTG
1001  AATTTTATAC  CTCTGTTTGT  TAGGGAATTG  AAACTGTAGA  ATATCTTGGT
      TTAAAATATG  GAGACAAACA  ATCCCTTAAC  TTTGACATCT  TATAGAACCA
```

FIG. 7B
pMOD (Erm-1)

```
1051  GAATTAAAGT  GACACGAATG  TTCAGTTTTA  ATTTTTCTGA  CGATAAGTTG
      CTTAATTTCA  CTGTGCTTAC  AAGTCAAAAT  TAAAAAGACT  GCTATTCAAC
1101  AATAGATGAC  TGTCTAATTC  AATAGACGTT  ACCTGTTTAC  TTATTTTAGC
      TTATCTACTG  ACAGATTAAG  TTATCTGCAA  TGGACAAATG  AATAAAATCG
1151  CAGTTTCGTC  GTTAAATGCC  CTTTACCTGT  TCCAATTTCG  TAAACGGTAT
      GTCAAAGCAG  CAATTTACGG  GAAATGGACA  AGGTTAAAGC  ATTTGCCATA
1201  CGGTTTCTTT  TAAATTCAAT  TGTTTTATTA  TTTGGTTGAG  TACCTTTTCA
      GCCAAAGAAA  ATTTAAGTTA  ACAAAATAAT  AAACCAACTC  ATGGAAAAGT
1251  TTCGTTAAAA  AGTTTTGAGA  ATATTTTATA  TTTTTGTTCA  TGTAATCACT
      AAGCAATTTT  TCAAAACTCT  TATAAAATAT  AAAAACAAGT  ACATTAGTGA
1301  CCTGAAGTGA  TACATCTATA  AATAAATACA  GAAGTTAAAC  GATTTGTTTG
      GGACTTCACT  ATGTAGATAT  TTATTTATGT  CTTCAATTTG  CTAAACAAAC
1351  TAATTTTAGT  TATCTGTTTA  AAAAGTCATA  AGATTAGTCA  CTGGTAGGAA
      ATTAAAATCA  ATAGACAAAT  TTTTCAGTAT  TCTAATCAGT  GACCATCCTT
1401  TTAATCTAAA  CGTATTTATC  TGCGTAATCA  CTGTTTTTAG  TCTGTTTCAA
      AATTAGATTT  GCATAAATAG  ACGCATTAGT  GACAAAAATC  AGACAAAGTT
1451  AACAGTAGAT  GTTTTATCTA  CATTACGCAT  TTGGAATACC  AACATGACGA
      TTGTCATCTA  CAAAATAGAT  GTAATGCGTA  AACCTTATGG  TTGTACTGCT
1501  ATCCCTCCTT  CTTAATTACA  AATTTTTAGC  ATCTAATTTA  ACTTCAATTC
      TAGGGAGGAA  GAATTAATGT  TTAAAAATCG  TAGATTAAAT  TGAAGTTAAG
1551  CTATTATACA  AAATTTTAAG  ATAATGCACT  ATCAACACAC  TCTTAAGTTT
      GATAATATGT  TTTAAAATTC  TATTACGTGA  TAGTTGTGTG  AGAATTCAAA
               HindIII                                  PvuII
1601  GCTTCTAAAG  CTTCAGGGTT  GAGATGTGTA  TAAGAGACAG  CTGCATTAAT
      CGAAGATTTC  GAAGTCCCAA  CTCTACACAT  ATTCTCTGTC  GACGTAATTA
1651  GAATCGGCCA  ACGCGCGGGG  AGAGGCGGTT  TGCGTATTGG  GCGCTCTTCC
      CTTAGCCGGT  TGCGCGCCCC  TCTCCGCCAA  ACGCATAACC  CGCGAGAAGG
1701  GCTTCCTCGC  TCACTGACTC  GCTGCGCTCG  GTCGTTCGGC  TGCGGCGAGC
      CGAAGGAGCG  AGTGACTGAG  CGACGCGAGC  CAGCAAGCCG  ACGCCGCTCG
1751  GGTATCAGCT  CACTCAAAGG  CGGTAATACG  GTTATCCACA  GAATCAGGGG
      CCATAGTCGA  GTGAGTTTCC  GCCATTATGC  CAATAGGTGT  CTTAGTCCCC
1801  ATAACGCAGG  AAAGAACATG  TGAGCAAAAG  GCCAGCAAAA  GGCCAGGAAC
      TATTGCGTCC  TTTCTTGTAC  ACTCGTTTTC  CGGTCGTTTT  CCGGTCCTTG
1851  CGTAAAAAGG  CCGCGTTGCT  GGCGTTTTTC  CATAGGCTCC  GCCCCCCTGA
      GCATTTTTCC  GGCGCAACGA  CCGCAAAAAG  GTATCCGAGG  CGGGGGGACT
1901  CGAGCATCAC  AAAAATCGAC  GCTCAAGTCA  GAGGTGGCGA  AACCCGACAG
      GCTCGTAGTG  TTTTTAGCTG  CGAGTTCAGT  CTCCACCGCT  TTGGGCTGTC
1951  GACTATAAAG  ATACCAGGCG  TTTCCCCCTG  GAAGCTCCCT  CGTGCGCTCT
      CTGATATTTC  TATGGTCCGC  AAAGGGGGAC  CTTCGAGGGA  GCACGCGAGA
2001  CCTGTTCCGA  CCCTGCCGCT  TACCGGATAC  CTGTCCGCCT  TTCTCCCTTC
      GGACAAGGCT  GGGACGGCGA  ATGGCCTATG  GACAGGCGGA  AAGAGGGAAC
2051  GGGAAGCGTG  GCGCTTTCTC  ATAGCTCACG  CTGTAGGTAT  CTCAGTTCGG
      CCCTTCGCAC  CGCGAAAGAG  TATCGAGTGC  GACATCCATA  GAGTCAAGCC
                                                ApaII
2101  TGTAGGTCGT  TCGCTCCAAG  CTGGGCTGTG  TGCACGAACC  CCCCGTTCAG
      ACATCCAGCA  AGCGAGGTTC  GACCCGACAC  ACGTGCTTGG  GGGGCAAGTC
2151  CCCGACCGCT  GCGCCTTATC  CGGTAACTAT  CGTCTTGAGT  CCAACCCGGT
      GGGCTGGCGA  CGCGGAATAG  GCCATTGATA  GCAGAACTCA  GGTTGGGCCA
```

FIG. 7C
pMOD (Erm-1)

```
2201  AAGACACGAC  TTATCGCCAC  TGGCAGCAGC  CACTGGTAAC  AGGATTAGCA
      TTCTGTGCTG  AATAGCGGTG  ACCGTCGTCG  GTGACCATTG  TCCTAATCGT
2251  GAGCGAGGTA  TGTAGGCGGT  GCTACAGAGT  TCTTGAAGTG  GTGGCCTAAC
      CTCGCTCCAT  ACATCCGCCA  CGATGTCTCA  AGAACTTCAC  CACCGGATTG
2301  TACGGCTACA  CTAGAAGGAC  AGTATTTGGT  ATCTGCGCTC  TGCTGAAGCC
      ATGCCGATGT  GATCTTCCTG  TCATAAACCA  TAGACGCGAG  ACGACTTCGG
2301  AGTTACCTTC  GGAAAAAGAG  TTGGTAGCTC  TTGATCCGGC  AAACAAACCA
      TCAATGGAAG  CCTTTTTCTC  AACCATCGAG  AACTAGGCCG  TTTGTTTGGT
2401  CCGCTGGTAG  CGGTGGTTTT  TTTGTTTGCA  AGCAGCAGAT  TACGCGCAGA
      GGCGACCATC  GCCACCAAAA  AAACAAACGT  TCGTCGTCTA  ATGCGCGTCT
2451  AAAAAAGGAT  CTCAAGAAGA  TCCTTTGATC  TTTTCTACGG  GGTCTGACGC
      TTTTTTCCTA  GAGTTCTTCT  AGGAAACTAG  AAAAGATGCC  CCAGACTGCG
2501  TCAGTGGAAC  GAAAACTCAC  GTTAAGGGAT  TTTGGTCATG  AGATTATCAA
      AGTCACCTTG  CTTTTGAGTG  CAATTCCCTA  AAACCAGTAC  TCTAATAGTT
2551  AAAGGATCTT  CACCTAGATC  CTTTTAAATT  AAAAATGAAG  TTTTAAATCA
      TTTCCTAGAA  GTGGATCTAG  GAAAATTTAA  TTTTTACTTC  AAAATTTAGT
2601  ATCTAAAGTA  TATATGAGTA  AACTTGGTCT  GACAGTTACC  AATGCTTAAT
      TAGATTTCAT  ATATACTCAT  TTGAACCAGA  CTGTCAATGG  TTACCAATTA
2651  CAGTGAGGCA  CCTATCTCAG  CGATCTGTCT  ATTTCGTTCA  TCCATAGTTG
      GTCACTCCGT  GGATAGAGTC  GCTAGACAGA  TAAAGCAAGT  AGGTATCAAC
2701  CCTGACTCCC  CGTCGTGTAG  ATAACTACGA  TACGGGAGGG  CTTACCATCT
      GGACTGAGGG  GCAGCACATC  TATTGATGCT  ATGCCCTCCC  GAATGGTAGA
2751  GGCCCCAGTG  CTGCAATGAT  ACCGCGAGAC  CCACGCTCAC  CGGCTCCAGA
      CCGGGGTCAC  GACGTTACTA  TGGCGCTCTG  GGTGCGAGTG  GCCGAGGTCT
2801  TTTATCAGCA  ATAAACCAGC  CAGCCGGAAG  GGCCGAGCGC  AGAAGTGGTC
      AAATAGTCGT  TATTTGGTCG  GTCGGCCTTC  CCGGCTCGCG  TCTTCACCAG
2851  CTGCAACTTT  ATCCGCCTCC  ATCCAGTCTA  TTAATTGTTG  CCGGGAAGCT
      GACGTTGAAA  TAGGCGGAGG  TAGGTCAGAT  AATTAACAAC  GGCCCTTCGA
2901  AGAGTAAGTA  GTTCGCCAGT  TAATAGTTTG  CGCAACGTTG  TTGCCATTGC
      TCTCATTCAT  CAAGCGGTCA  ATTATCAAAC  GCGTTGCAAC  AACGGTAACG
2951  TACAGGCATC  GTGGTGTCAC  GCTCGTCGTT  TGGTATGGCT  TCATTCAGCT
      ATGTCCGTAG  CACCACAGTG  CGAGCAGCAA  ACCATACCGA  AGTAAGTCGA
3001  CCGGTTCCCA  ACGATCAAGG  CGAGTTACAT  GATCCCCCAT  GTTGTGCAAA
      GGCCAAGGGT  TGCTAGTTCC  GCTCAATGTA  CTAGGGGGTA  CAACACGTTT
3051  AAAGCGGTTA  GCTCCTTCGG  TCCTCCGATC  GTTGTCAGAA  GTAAGTTGGC
      TTTCGCCAAT  CGAGGAAGCC  AGGAGGCTAG  CAACAGTCTT  CATTCAACCC
3101  CGCAGTGTTA  TCACTCATGG  TTATGGCAGC  ACTGCATAAT  TCTCTTACTG
      GCGTCACAAT  AGTGAGTACC  AATACCGTCG  TGACGTATTA  AGAGAATGAC
3151  TCATGCCATC  CGTAAGATGC  TTTTCTGTGA  CTGGTGAGTA  CTCAACCAAG
      AGTACGGTAG  GCATTCTACG  AAAAGACACT  GACCACTCAT  GAGTTGGTTC
3201  TCATTCTGAG  AATAGTGTAT  GCGGCGACCG  AGTTGCTCTT  GCCCGGCGTC
      AGTAAGACTC  TTATCACATA  CGCCGCTGGC  TCAACGAGAA  CGGGCCGCAG
3251  AATACGGGAT  AATACCGCGC  CACATAGCAG  AACTTTAAAA  GTGCTCATCA
      TTATGCCCTA  TTATGGCGCG  GTGTATCGTC  TTGAAATTTT  CACGAGTAGT
3301  TTGGAAAACG  TTCTTCGGGG  CGAAAACTCT  CAAGGATCTT  ACCGCTGTTG
      AACCTTTTGC  AAGAAGCCCC  GCTTTTGAGA  GTTCCTAGAA  TGGCGACAAC
```

FIG. 7D
pMOD (Erm-I)

```
                                        ApaI I
3351  AGATCCAGTT  CGATGTAACC  CACTCGTGCA  CCCAACTGAT  CTTCAGCATC
      TCTAGGTCAA  GCTACATTGG  GTGAGCACGT  GGGTTGACTA  GAAGTCGTAG
3401  TTTTACTTTC  ACCAGCGTTT  CTGGGTGAGC  AAAAACAGGA  AGGCAAAATG
      AAAATGAAAG  TGGTCGCAAA  GACCCACTCG  TTTTTGTCCT  TCCGTTTTAC
3451  CCGCAAAAAA  GGGAATAAGG  GCGACACGGA  AATGTTGAAT  ACTCATACTC
      GGCGTTTTTT  CCCTTATTCC  CGCTGTGCCT  TTACAACTTA  TGAGTATGAG
3501  TTCCTTTTTC  AATATTATTG  AAGCATTTAT  CAGGGTTATT  GTCTCATGAG
      AAGGAAAAAG  TTATAATAAC  TTCGTAAATA  GTCCCAATAA  CAGAGTACTC
3351  CGGATACATA  TTTGAATGTA  TTTAGAAAAA  TAAACAAATA  GGGGTTCCGC
      GCCTATGTAT  AAACTTACAT  AAATCTTTTT  ATTTGTTTAT  CCCCAAGGCG
3601  GCACATTTCC  CCGAAAAGTG  CCACCTGACG  TCTAAGAAAC  CATTATTATC
      CGTGTAAAGG  GGCTTTTCAC  GGTGGACTGC  AGATTCTTTG  GTAATAATAG
3651  ATGACATTAA  CCTATAAAAA  TAGGCGTATC  ACGAG
      TACTGTAATT  GGATATTTTT  ATCCGCATAG  TGCTC
```

FIG. 8A
pMOD (Cm)

```
  1  TCGCGCGTTT  CGGTGATGAC  GGTGAAAACC  TCTGACACAT  GCAGCTCCCG
     AGCGCGCAAA  GCCACTACTG  CCACTTTTGG  AGACTGTGTA  CGTCGAGGGC
 51  GAGACGGTCA  CAGCTTGTCT  GTAAGCGGAT  GCCGGGAGCA  GACAAGCCCG
     CTCTGCCAGT  GTCGAACAGA  CATTCGCCTA  CGGCCCTCGT  CTGTTCGGGC
101  TCAGGGCGCG  TCAGCGGGTG  TTGGCGGGTG  TCGGGGCTGG  CTTAACTATG
     AGTCCCGCGC  AGTCGCCCAC  AACCGCCCAC  AGCCCCGACC  GAATTGATAC
                                              ApaLI
151  CGGCATCAGA  GCAGATTGTA  CTGAGAGTGC  ACCATATGCG  GTGTGAAATA
     GCCGTAGTCT  CGTCTAACAT  GACTCTCACG  TGGTATACGC  CACACTTTAT
201  CCGCACAGAT  GCGTAAGGAG  AAAATACCGC  ATCAGGCGCC  ATTCGCCATT
     GGCGTGTCTA  CGCATTCCTC  TTTTATGGCG  TAGTCCGCGG  TAAGCGGTAA
251  CAGGCTGCGC  AACTGTTGGG  AAGGGCGATC  GGTGCGGGCC  TCTTCGCTAT
     GTCCGACGCG  TTGACAACCC  TTCCCGCTAG  CCACGCCCGG  AGAAGCGATA
                                                         EcoRI
         PvuII
301  TACGCCAGCT  GTCTCTTATA  CACATCTCAA  CCATCATCGA  TGAATTCGAG
     ATGCGGTCGA  CAGAGAATAT  GTGTAGAGTT  GGTAGTAGCT  ACTTAAGCTC
       KpnI                                ClaI
351  CTCGGTACCG  TTAGTGACAT  TAGAAAACCG  ACTGTAAAAA  GTACAGTCGG
     GAGCCATGGC  AATCACTGTA  ATCTTTTGGC  TGACATTTTT  CATGTCAGCC
401  CATTATCTCA  TATTATAAAA  GCCAGTCATT  AGGCCTATCT  GACAATTCCT
     GTAATAGAGT  ATAATATTTT  CGGTCAGTAA  TCCGGATAGA  CTGTTAAGGA
451  GAATAGAGTT  CATAAACAAT  CCTGCATGAT  AACCATCACA  AACAGAATGA
     CTTATCTCAA  GTATTTGTTA  GGACGTACTA  TTGGTAGTGT  TTGTCTTACT
501  TGTACCTGTA  AAGATAGCGG  TAAATATATT  GAATTACCTT  TATTAATGAA
     ACATGGACAT  TTCTATCGCC  ATTTATATAA  CTTAATGGAA  ATAATTACTT
551  TTTTCCTGCT  GTAATAATGG  GTAGAAGGTA  ATTACTATTA  TTATTGATAT
     AAAAGGACGA  CATTATTACC  CATCTTCCAT  TAATGATAAT  AATAACTATA
                                Ncol
601  TTAAGTTAAA  CCCAGTAAAT  GAAGTCCATG  GAATAATAGA  AAGAGAAAAA
     AATTCAATTT  GGGTCATTTA  CTTCAGGTAC  CTTATTATCT  TTCTCTTTTT
651  GCATTTTCAG  GTATAGGTGT  TTTGGGAAAC  AATTTCCCCG  AACCATTATA
     CGTAAAAGTC  CATATCCACA  AAACCCTTTG  TTAAAGGGGC  TTGGTAATAT
701  TTTCTCTACA  TCAGAAAGGT  ATAAATCATA  AAACTCTTTG  AAGTCATTCT
     AAAGAGATGT  AGTCTTTCCA  TATTTAGTAT  TTTGAGAAAC  TTCAGTAAGA
751  TTACAGGAGT  CCAAATACCA  GAGAATGTTT  TAGATACACC  ATCAAAAATT
     AATGTCCTCA  GGTTTATGGT  CTCTTACAAA  ATCTATGTGG  TAGTTTTTAA
801  GTATAAAGTG  GCTCTAACTT  ATCCCAATAA  CCTAACTCTC  CGTCGCTATT
     CATATTTCAC  CGAGATTGAA  TAGGGTTATT  GGATTGAGAG  GCAGCGATAA
851  GTAACCAGTT  CTAAAAGCTG  TATTTGAGTT  TATCACCCTT  GTCACTAAGA
     CATTGGTCAA  GATTTTCGAC  ATAAACTCAA  ATAGTGGGAA  CAGTGATTCT
901  AAATAAATGC  AGGGTAAAAT  TTATATCCTT  CTTGTTTTAT  GTTTCGGTAT
     TTTATTTACG  TCCCATTTTA  AATATAGGAA  GAACAAAATA  CAAAGCCATA
951  AAAACACTAA  TATCAATTTC  TGTGGTTATA  CTAAAGTCG   TTTGTTGGTT
     TTTTGTGATT  ATAGTTAAAG  ACACCAATAT  GATTTTCAGC  AAACAACCAA
1001 CAAATAATGA  TTAAATATCT  CTTTTCTCTT  CCAATTGTCT  AAATCAATTT
     GTTTATTACT  AATTTATAGA  GAAAAGAGAA  GGTTAACAGA  TTTAGTTAAA
```

FIG. 8B
pMOD (Cm)

```
1051 TATTAAAGTT CATTTGATAT GCCTCCTAAA TTTTTATCTA AAGTGAATTT
     ATAATTTCAA GTAAACTATA CGGAGGATTT AAAAATAGAT TTCACTTAAA
1101 AGGAGGCTTA CTTGTCTGCT TTCTTCATTA GAATCAATCC TTTTTTAAAA
     TCCTCCGAAT GAACAGACGA AAGAAGTAAT CTTAGTTAGG AAAAAATTTT
                    HindIII                              PvuII
1151 GTCAATATTA CTGTAACAAG CTTCAGGGTT GAGATGTGTA TAAGAGACAG
     CAGTTATAAT GACATTGTTC GAAGTCCCAA CTCTACACAT ATTCTCTGTC
     PvuII
1201 CTGCATTAAT GAATCGGCCA ACGCGCGGGG AGAGGCGGTT TGCGTATTGG
     GACGTAATTA CTTAGCCGGT TGCGCGCCCC TCTCCGCCAA ACGCATAACC
1251 GCGCTCTTCC GCTTCCTCGC TCACTGACTC GCTGCGCTCG GTCGTTCGGC
     CGCGAGAAGG CGAAGGAGCG AGTGACTGAG CGACGCGAGC CAGCAAGCCG
1301 TGCGGCGAGC GGTATCAGCT CACTCAAAGG CGGTAATACG GTTATCCACA
     ACGCCGCTCG CCATAGTCGA GTGAGTTTCC GCCATTATGC CAATAGGTGT
1351 GAATCAGGGG ATAACGCAGG AAAGAACATG TGAGCAAAAG GCCAGCAAAA
     CTTAGTCCCC TATTGCGTCC TTTCTTGTAC ACTCGTTTTC CGGTCGTTTT
1401 GGCCAGGAAC CGTAAAAAGG CCGCGTTGCT GGCGTTTTTC CATAGGCTCC
     CCGGTCCTTG GCATTTTTCC GGCGCAACGA CCGCAAAAAG GTATCCGAGG
1451 GCCCCCCTGA CGAGCATCAC AAAAATCGAC GCTCAAGTCA GAGGTGGCGA
     CGGGGGGACT GCTCGTAGTG TTTTTAGCTG CGAGTTCAGT CTCCACCGCT
1501 AACCCGACAG GACTATAAAG ATACCAGGCG TTTCCCCCTG GAAGCTCCCT
     TTGGGCTGTC CTGATATTTC TATGGTCCGC AAAGGGGGAC CTTCGAGGGA
1551 CGTGCGCTCT CCTGTTCCGA CCCTGCCGCT TACCGGATAC CTGTCCGCCT
     GCACGCGAGA GGACAAGGCT GGGACGGCGA ATGGCCTATG GACAGGCGGA
1601 TTCTCCCTTC GGGAAGCGTG GCGCTTTCTC ATAGCTCACG CTGTAGGTAT
     AAGAGGGAAG CCCTTCGCAC CGCGAAAGAG TATCGAGTGC GACATCCATA
                                                ApaLI
1651 CTCAGTTCGG TGTAGGTCGT TCGCTCCAAG CTGGGCTGTG TGCACGAACC
     GAGTCAAGCC ACATCCAGCA AGCGAGGTTC GACCCGACAC ACGTGCTTGG
1701 CCCCGTTCAG CCCGACCGCT GCGCCTTATC CGGTAACTAT CGTCTTGAGT
     GGGGCAAGTC GGGCTGGCGA CGCGGAATAG GCCATTGATA GCAGAACTCA
1751 CCAACCCGGT AAGACACGAC TTATCGCCAC TGGCAGCAGC CACTGGTAAC
     GGTTGGGCCA TTCTGTGCTG AATAGCGGTG ACCGTCGTCG GTGACCATTG
1801 AGGATTAGCA GAGCGAGGTA TGTAGGCGGT GCTACAGAGT TCTTGAAGTG
     TCCTAATCGT CTCGCTCCAT ACATCCGCCA CGATGTCTCA AGAACTTCAC
1851 GTGGCCTAAC TACGGCTACA CTAGAAGGAC AGTATTTGGT ATCTGCGCTC
     CACCGGATTG ATGCCGATGT GATCTTCCTG TCATAAACCA TAGACGCGAG
1901 TGCTGAAGCC AGTTACCTTC GGAAAAAGAG TTGGTAGCTC TTGATCCGGC
     ACGACTTCGG TCAATGGAAG CCTTTTTCTC AACCATCGAG AACTAGGCCG
1951 AAACAAACCA CCGCTGGTAG CGGTGGTTTT TTTGTTTGCA AGCAGCAGAT
     TTTGTTTGGT GGCGACCATC GCCACCAAAA AAACAAACGT TCGTCGTCTA
2001 TACGCGCAGA AAAAAAGGAT CTCAAGAAGA TCCTTTGATC TTTTCTACGG
     ATGCGCGTCT TTTTTTCCTA GAGTTCTTCT AGGAAACTAG AAAAGATGCC
2051 GGTCTGACGC TCAGTGGAAC GAAAACTCAC GTTAAGGGAT TTTGGTCATG
     CCAGACTGCG AGTCACCTTG CTTTTGAGTG CAATTCCCTA AAACCAGTAC
2101 AGATTATCAA AAAGGATCTT CACCTAGATC CTTTTAAATT AAAAATGAAG
     TCTAATAGTT TTTCCTAGAA GTGGATCTAG GAAAATTTAA TTTTTACTTC
```

FIG. 8C
pMOD (Cm)

```
2151  TTTTAAATCA  ATCTAAAGTA  TATATGAGTA  AACTTGGTCT  GACAGTTACC
      AAAATTTAGT  TAGATTTCAT  ATATACTCAT  TTGAACCAGA  CTGTCAATGG
2201  AATGCTTAAT  CAGTGAGGCA  CCTATCTCAG  CGATCTGTCT  ATTTCGTTCA
      TTACGAATTA  GTCACTCCGT  GGATAGAGTC  GCTAGACAGA  TAAAGCAAGT
2251  TCCATAGTTG  CCTGACTCCC  CGTCGTGTAG  ATAACTACGA  TACGGGAGGG
      AGGTATCAAC  GGACTGAGGG  GCAGCACATC  TATTGATGCT  ATGCCCTCCC
2301  CTTACCATCT  GGCCCCAGTG  CTGCAATGAT  ACCGCGAGAC  CCACGCTCAC
      GAATGGTAGA  CCGGGGTCAC  GACGTTACTA  TGGCGCTCTG  GGTGCGAGTG
2351  CGGCTCCAGA  TTTATCAGCA  ATAAACCAGC  CAGCCGGAAG  GGCCGAGCGC
      GCCGAGGTCT  AAATAGTCGT  TATTTGGTCG  GTCGGCCTTC  CCGGCTCGCG
2401  AGAAGTGGTC  CTGCAACTTT  ATCCGCCTCC  ATCCAGTCTA  TTAATTGTTG
      TCTTCACCAG  GACGTTGAAA  TAGGCGGAGG  TAGGTCAGAT  AATTAACAAC
2451  CCGGGAAGCT  AGAGTAAGTA  GTTCGCCAGT  TAATAGTTTG  CGCAACGTTG
      GGCCCTTCGA  TCTCATTCAT  CAAGCGGTCA  ATTATCAAAC  GCGTTGCAAC
2501  TTGCCATTGC  TACAGGCATC  GTGGTGTCAC  GCTCGTCGTT  TGGTATGGCT
      AACGGTAACG  ATGTCCGTAG  CACCACAGTG  CGAGCAGCAA  ACCATACCGA
2551  TCATTCAGCT  CCGGTTCCCA  ACGATCAAGG  CGAGTTACAT  GATCCCCCAT
      AGTAAGTCGA  GGCCAAGGGT  TGCTAGTTCC  GCTCAATGTA  CTAGGGGGTA
2601  GTTGTGCAAA  AAAGCGGTTA  GCTCCTTCGG  TCCTCCGATC  GTTGTCAGAA
      CAACACGTTT  TTTCGCCAAT  CGAGGAAGCC  AGGAGGCTAG  CAACAGTCTT
2651  GTAAGTTGGC  CGCAGTGTTA  TCACTCATGG  TTATGGCAGC  ACTGCATAAT
      CATTCAACCG  GCGTCACAAT  AGTGAGTACC  AATACCGTCG  TGACGTATTA
2701  TCTCTTACTG  TCATGCCATC  CGTAAGATGC  TTTTCTGTGA  CTGGTGAGTA
      AGAGAATGAC  AGTACGGTAG  GCATTCTACG  AAAAGACACT  GACCACTCAT
2751  CTCAACCAAG  TCATTCTGAG  AATAGTGTAT  GCGGCGACCG  AGTTGCTCTT
      GAGTTGGTTC  AGTAAGACTC  TTATCACATA  CGCCGCTGGC  TCAACGAGAA
2801  GCCCGGCGTC  AATACGGGAT  AATACCGCGC  CACATAGCAG  AACTTTAAAA
      CGGGCCGCAG  TTATGCCCTA  TTATGGCGCG  GTGTATCGTC  TTGAAATTTT
2851  GTGCTCATCA  TTGGAAAACG  TTCTTCGGGG  CGAAAACTCT  CAAGGATCTT
      CACGAGTAGT  AACCTTTTGC  AAGAAGCCCC  GCTTTTGAGA  GTTCCTAGAA
                                                    ApaLI
2901  ACCGCTGTTG  AGATCCAGTT  CGATGTAACC  CACTCGTGCA  CCCAACTGAT
      TGGCGACAAC  TCTAGGTCAA  GCTACATTGG  GTGAGCACGT  GGGTTGACTA
2951  CTTCAGCATC  TTTTACTTTC  ACCAGCGTTT  CTGGGTGAGC  AAAAACAGGA
      GAAGTCGTAG  AAAATGAAAG  TGGTCGCAAA  GACCCACTCG  TTTTTGTCCT
3001  AGGCAAAATG  CCGCAAAAAA  GGGAATAAGG  GCGACACGGA  AATGTTGAAT
      TCCGTTTTAC  GGCGTTTTTT  CCCTTATTCC  CGCTGTGCCT  TTACAACTTA
3051  ACTCATACTC  TTCCTTTTTC  AATATTATTG  AAGCATTTAT  CAGGGTTATT
      TGAGTATGAG  AAGGAAAAAG  TTATAATAAC  TTCGTAAATA  GTCCCAATAA
3101  GTCTCATGAG  CGGATACATA  TTTGAATGTA  TTTAGAAAAA  TAAACAAATA
      CAGAGTACTC  GCCTATGTAT  AAACTTACAT  AAATCTTTTT  ATTTGTTTAT
3151  GGGGTTCCGC  GCACATTTCC  CCGAAAAGTG  CCACCTGACG  TCTAAGAAAC
      CCCCAAGGCG  CGTGTAAAGG  GGCTTTTCAC  GGTGGACTGC  AGATTCTTTG
3201  CATTATTATC  ATGACATTAA  CCTATAAAAA  TAGGCGTATC  ACGAG
      GTAATAATAG  TACTGTAATT  GGATATTTT   ATCCGCATAG  TGCTC
```

RANDOM TRANSPOSON INSERTION IN STAPHYLOCOCCUS AUREUS AND USE THEREOF TO IDENTIFY ESSENTIAL GENES

This application is a National Stage application of copending PCT application PCT/US2003/025879 filed 20 Aug. 2003, which was published in the English language under PCT Article 21(2) on 04 Mar. 2004, and claims the benefit of provisional application Ser. No. 60/404,406 filed Aug. 20, 2002. The disclosures of each are expressly incorporated herein.

FIELD OF INVENTION

The present invention relates to a novel method of generating random transposon insertions in the genome of Staphylococcus aureus (S. aureus). The present invention further relates to the use of random transposon mutants generated by such method to identify putative essential S. aureus genes. The invention further relates to the use of such genes in screening assays to identify, evaluate or design antibacterial agents useful for the treatment of Staphylococcus infections and for the production of Staphylococcus vaccines. Such antibacterial agents are useful for treating or preventing opportunistic infections in immunocompromised individuals and for treating and preventing hospital acquired staphylococcus infections, septicemia, endocarditis, scarlet fever and toxic-shock syndrome associated with Staphylococcus infection. Also disclosed is a Bayession statistical model that may be used to increase the statistical confidence that any given gene-identified using the disclosed transposon insertion methodology is essential.

BACKGROUND OF INVENTION

S. aureus is a gram-positive bacterium grouped within Bacillus sp. on the basis of ribosomal RNA sequences. This immobile coccus grows in aerobic and anaerobic conditions, in which it forms grape-like clusters. Its main habitats are the nasal membranes and skin of warm-blooded animals, in r whom it causes a range of infections from mild to serve, such as pneumonia, sepsis, osteomyelitis, and infectious endocarditis. The organism produces many toxins and is highly effective at overcoming antibiotic effectiveness. In fact, S. aureus is one of the major causes of community-acquired and hospital-acquired infections, and its toxins include super-antigens that cause unique disease entities such as toxic shock syndrome and Staphylococcus-associated scarlet fever. In 1961 it was first reported that this bacteria developed resistance to methicillin, invalidating almost all antibiotics including the most potent beta lactams.

In this regard, reports of bacterial strains becoming resistant to known antibiotics are becoming more common, signaling that new antibiotics are needed to combat all bacterial infections, and particularly combat S. aureus, an organism responsible for many nosocomial infections. Unfortunately, historically the identification of new antibiotics has been painstakingly laborious with no guarantee of success. Traditional methods have involved blindly and randomly testing potential drug candidate molecules, with the hope that one might be effective. Presently, the average cost to discover and develop a new drug is nearly $500 million, and average time for drug development is 15 years from laboratory to patient. Clearly new identification and screening methods that will shorten and reduce the cost of this process are needed.

A newly emerging regime for identifying new antibacterial agents is to first identify gene sequences and proteins required for bacterial proliferation of ("essential genes and essential proteins") and then conduct a biochemical and structural analysis of the particular target gene or protein in order to identify compounds that interact with the target. Such methodology combines molecular modeling technology, combinational chemistry and the means to design candidate drugs, and affords a more directed alternative to merely screening random compounds with the hope that one might be effective for inhibiting or eradicating a particular bacteria.

Nevertheless, even this preferred approach presents obstacles including the identification of essential genes and proteins, and the design of new assays for the genes thus identified in order to efficiently screen candidate compounds. With report to this approach, several groups have proposed systems for the identification of essential genes. For instance, Zyskind and colleagues propose a method of identifying essential genes in Escherichia coli by subcloning a library of E. coli nucleic acid sequences into an inducible expression vector, introducing the vectors into a population of E. coli cells, isolating those vectors that, upon activation and expression, negatively impact the growth of the E. coli cell, and characterizing the nucleic acid sequences and open reading frames contained on the subclones identified. See WO 00/44906, herein incorporated by reference. The disadvantage of this method is that the overexpression of nonessential genes can also negatively impact the cell, particularly the overexpression of membrane proteins and sugar transport proteins that are not necessary for growth where alternative carbon sources exist. Such proteins typically become trapped in membrane export systems when the cell is overloaded, and would be identified by this methodology. See Muller, FEMS Microbiol. Lett. 1999 Jul. 1; 176(1):219-27.

Another group proposes the identification of growth conditional mutants, and more specifically temperature sensitive (ts) mutants, as a means to identify essential genes in Staphylococcus aureus. See Benton et al., U.S. Pat. No. 6,037,123, issued Mar. 14, 2000, herein incorporated by reference. Each gene is identified by isolating recombinant bacteria derived from growth conditional mutant strains, i.e., following introduction of a vector containing a library of nucleic acid sequences, which would grow under non-permissive conditions but which were not revertants. These recombinant bacteria were found to contain DNA inserts that encoded wild type gene products that replaced the function of the mutated gene under non-permissive growth conditions. By this method, Benton and colleagues were able to identify 38 loci on the S. aureus chromosome, each consisting of at least one essential gene.

The disadvantages of this method are first, the chemical employed to induce mutagenesis (diethyl sulfate, DES) is capable of causing several mutations in the same cell, thereby complicating interpretation of the results. Second, the method is particularly labor intensive in that one must painstakingly analyze replica plates of individual colonies grown at permissive and non-permissive temperatures, where replica plates include both mutant and non-mutant cells. Thus, employing the appropriate level of mutagen to achieve a balance between minimizing the number of non-mutant colonies one must screen in order to identify one mutant, while at the same time avoiding multiple mutations in the same cell, may be an arduous task.

Another group has proposed a transposon mutagenesis system for identifying essential genes called "GAMBIT" ("genomic analysis and mapping by in vitro transposition"), and has used the system to identify essential genes first in the gram positive bacteria Haemophilus influenzae and Streptococcus pneumoniae, and more recently in Pseudomonas

*aeruginosa.* See Akerley et al., Systematic identification of essential genes by In vitro mariner mutagenesis, Proc. Natl. Acad. Sci USA 95(15): 8927-32; Wong and Mekalanos, 2000, Proc. Natl. Acad. Sci. USA 97(18): 10191-96; and Mekalanos et al., U.S. Pat. No. 6,207,384, issued Mar. 27, 2001, herein incorporated by reference. GAMBIT involves first isolating and purifying specific genomic segments of approximately 10 kilobases using extended-length PCR, and creating a high density transposon insertion map of the isolated region using Himar1 transposon mutagenesis. The transposon insertions are then transferred to the chromosome following transformation of the bacteria with the transposon containing vectors, and selection for the antibiotic resistance marker on the transposon. The position of each transposon insertion with respect to a given PCR primer is then determined by genetic footprinting, i.e., by amplifying sub-PCR products using one of the original PCR primers and a primer that recognizes an internal site in the Himar1 transposon. By analyzing the length of PCR fragments thus identified, it is possible to identify regions that are devoid of transposon insertions, thereby signaling regions that might contain essential genes.

While the GAMBIT method is a good technique for looking at a small region of the genome for essential genes, it would be extremely labor intensive to use this method for analyzing the entire genome. Furthermore, GAMBIT is not readily applicable for use in organisms that are less recombinogenic than *H. influenzae.*

Another group at Abbott Laboratories has proposed a genome scanning method for identification of putative essential genes in *H. influenzae*, whereby random transposon insertions are mapped and analyzed to identify open reading frames containing no insertion in order to identify putative essential genes. Reich et al., 1999, Genome Scanning in *Haemophilus influenzae* for Identification of Essential Genes, J. Bacteriol. 181(16): 4961-68. However, even though transposon insertions were isolated that spanned the whole genome, the authors employed a genomic footprinting technique similar to that used in GAMBIT to map insertions in a short contiguous region of the chromosome. The method further employs the methods of mutation exclusion and zero time analysis in order to monitor the fate of individual insertions after transformation in growing culture, which looks at individual insertions on a case-by-case basis.

Wong and Mekalanos also proposed identifying essential genes in *P. aeruginosa* by starting with the knowledge of three essential genes in *H. influenzae* and using genetic footprint analysis to determine if the homologues of these genes are essential in *P. aeruginosa.* Of three homologues tested, only one was unable to accommodate a transposon insertion. See Wong and Mekalanos, supra. Such results underscore the fact that a gene that is shown to be essential in one species will not necessarily be essential in another, given that some gene products may fulfill different functional roles in different species.

Because of the fact that *S. aureus* is a major cause of life-threatening infection, and its notorious resistance to antibiotics, various groups have reported approaches for identification of *S. aureus* essential genes as these genes are useful potential targets for antibacterial chemotherapy and for producing therapeutic and prophylactic vaccines.

The availability of the genome sequence of *S. aureus*, and related bacteria, makes possible studies attempting to identify genes that are essential for viability of the microorganism in vitro or for its ability to cause infection. The products of both types of genes are potential targets in the effort to produce effective antimicrobial agents. Related thereto, Kuroda et al. recently published in the Lancet the whole genome sequence of two related *S. aureus* strains (N315 and Mu50) by shot-gun random sequencing. N315 is a meticillin-resistant *S. aureus* strain isolated in 1982 and Mu50 is an MRSA strain with vancomycin resistance isolated in 1997. In their paper Kuroda et al. reported the identification of open reading frames by the use of GAMBLER and GLIMMER programs, and annotation of each by BLAST homology search, motif analysis and protein localisation prediction.

Also, Ji et al. recently reported a method for the identification of essential *Staphylococcus* genes using conditional phenotypes generated by antisense RNA. (Ji et al., Science, 293: 2266-2269 (Sep. 21, 2001)). Using this method, Ji et al. reported the identification of more than 150 putative essential *Staphylococcus* genes where antisense ablation was lethal or had growth inhibitory effects. Of these genes, 40% are reportedly orthologs or homologs of known essential bacterial genes.

Further, Xia et. al. recently reported a method reportedly useful for rapid identification of essential genes of *Staphylococcus aureus* using a vector host-dependent for autonomous replication, PSA3182. This approach is based on the insertion by a single crossover of a specific DNA sequence both in the middle of a structural gene, with the inherent inactivation of the gene, and at its 3' end, where the insertion does not affect the structural gene but might have a polar effect on downstream genes (Xia et al., Plasmid 42:144-49(1999)). Their approach includes comparison of the frequency of the insertion at these two locations as a means for predicting of the essential character of a particular gene. Accordingly, in their strategy, for each studied gene, different fragments located either in the middle of a coding sequence or at its 3' end, are introduced into a vector host dependent for autonomous replication, PSA3182. Xia et al., report the use of their approach to test the essential character of four *S. aureus* genes, nusG, divIB, dbpA and dbpB.

Also, Jana et al., also recently reported a method for identifying genes that are essential in *S. aureus*, by fusing the gene of interest to an IPTG controllable spac promoter and provide a general approach by constructing a plasmid in which the Cat-Pspac cos sites is flanked by cloning sites suitable for inserting DNA fragments of interest (Jana et al., Plasmid 44:100-4 (2000)).

Still further, Zhang et al., report a method for identifying essential genes of *S. aureus* using a chromosomally-integrated spac system in combination with a Lac 1-expressing plasmid PFF 40. This combination reportedly provides an inducible, titratable and well-regulated system for testing the requirements of specific gene products for cell viability and conditional lethal phenotypes in *S. aureus.* (Zhang et al. Gene 235: 297-305 (2000)).

Another method for the identification of bacterial essential genes is entitled Transposon Mediated Differential Hybridisation (TMDH), which is disclosed in WO 01/07651, herein incorporated by reference. This method entails (i) providing a library of transposon mutants of the target organism; (ii) isolating polynucleotide sequences from the library which flank inserted transposons; (iii) hybridising said polynucleotide sequences with a polynucleotide library from said organism; and (iv) identifying a polynucleotide in the polynucleotide library to which said polynucleotide sequences do not hybridise in order to identify an essential gene of the organism. However, the problem with this methodology is that it has a high propensity to lead to false positives, and many essential genes will be missed. Furthermore, the method does not yield any detailed information regarding the loci disrupted by transposons, or whether they were hit more than once.

Previous attempts to generate random tranposon insertions in the *S. aureus* genome have encountered numerous difficulties. For instance, previous transposon systems for *S. aureus* have created insertions predominantly concentrated in genomic "hot spots". In addition, difficulties have been encountered in obtaining viable *S. aureus* bacteria after electroporation procedures, making it difficult to generate a statistically significant number of mutations for mapping and to differentiate between essential and nonessential mutations.

Thus, there is a great need for more efficient methods to identify essential genes, particularly in *S. aureus* so that new antibacterial agents may be designed therefrom for use in treatment of *S. aureus* infections.

SUMMARY OF INVENTION

The present inventors have developed a novel and efficient method for generating random transposon insertions in the *Staphylococcous* genome, preferably in the genome of *S. aureus*. The inventive method provides for random insertion into the entire bacterial *Staphylococcus* genome.

The methods of the invention further provide a method for generating a random insertion into a *Staphylococcus* genome comprising subjecting Staphylococcal cells to random mutagenesis and culturing the mutagenized cells in a recovery broth. Preferably, the recovery broth is B2 Broth.

The recovery broth used in the invention preferably comprises B2 Broth. The B2 Broth used in the invention comprises from 0.5% to 1.5% casein hydrolysate, preferably 1.0% casein hydrosylate, from 2.0% to 3.0% yeast extract, preferably 2.5% yeast extract, from 2.0% to 3.0% NaCl, preferably 2.5% NaCl, and from 0.05% to 0.15% $K_2HPO_4$, preferably 0.1% $K_2HPO_4$. The B2 Broth used in the invention is preferably buffered to about pH 7.0.

Methods of subjecting cells to random mutagenesis are known in the art, and include, for instance, commercially available transposon mutagenesis products.

More particularly, using this novel random transposon insertion method, the present inventors have generated >7400 viable transposon mutants, and have determined through PCR and DNA sequencing the genomic insertion site of a majority of these mutants. Since the insertion of a transposon DNA into a bacterial genome disrupts the function of the gene at a particular location, the generation of a viable transposon mutant provides direct evidence that the disrupted gene contained in the particular mutant is not essential to the bacteria survival under the tested growth conditions. Accordingly, by systematically repeating the subject random transposon insertion method, it is anticipated that all or substantially all *S. aureus* non-essential genes can be identified, based on the successful generation of viable transposon mutants which contain a transposon DNA inserted into the particular non-essential gene. Thus, putative essential genes are identified by elimination, i.e., putative essential genes are *S. aureus* where no transposon mutants are generated containing a transposon DNA inserted therein. (As discussed in greater detail infra, the probability that a putative essential gene identified according to the invention is in fact essential also depends on the size of the particular gene, and can be further validated by use of statistical methods).

Moreover, the present inventors have developed a method that is useful for providing a database of potential essential or otherwise important *S. aureus* genes which may be used to verify essentiality and to design antibacterial agents active against the identified targets.

Also, the invention encompasses the use of essential genes and proteins identified by the invention transposon mutagenesis protocols to produce therapeutic and prophylactic vaccines for conferring therapeutic and prophylactic immunity against *Staphylococcus* infection. These vaccines will comprise the bacterial antigen or fragment thereof identified by the invention, antibodies that specifically bind the antigen, including both polyclonal, monclonal and nonclonal, or may comprise nuclear acid sequence based vaccines that contain a DNA sequence that encodes the said antigen or antigen fragment or antibody specification thereto.

Additionally, the invention allows for the identification of "motifs", of the essential genes identified by the invention, i.e., regions of the gene which are similar or related to that of other bacterial genes, and the use of these motifs as targets to screen compound libraries for compounds that inhibit or inactivate a desired gene function.

Particularly, the inventors have generated >7400 transposon mutants and have determined the genomic insertion site of most of these mutants via PCR and DNA sequencing. Using the publicly available *S. aureus* genomic sequence, a map of transposon insertions is then generated, preferably using a library of at least about 3,000 to 6,000 transposon insertions, and more preferably using a library of at least about 4,000 to 5,000 transposon insertions. The generated map is used to provide a database of about 500 to 1500 open reading frames, or more particularly 1000 to 1400 reading frames for which no transposon insertions are obtained, each of which represents a potential essential gene required for growth and proliferation of *S. aureus* in the growth media and conditions disclosed infra in the experimental protocols or an important gene, the mutation of which results in an attenuated growth mutant.

Thus, one aspect of the invention is to provide a database of putative essential important genes, defined by the absence of transposon insertions in those genes in a High Throughput Transposon Insertion Map (HTTIM) database comprising about 3000 to 8000 transposon insertions in the genome of *S. aureus*. Minimally, such a database comprises approximately 1294 open reading frames (ORFs), each of which may be further tested for essentiality using a variety of tests disclosed herein. However, predictions of essentiality may be bolstered based on length of the ORF and predicted function and other statistical factors, thereby providing for more narrow databases of putative essential genes. Thus, the invention also encompasses the production of databases that are more narrow and comprise only those genes for which essentiality may be predicted with at least an 80% confidence level, and include at least about 600 to 625 genes. The invention also includes databases assigned a confidence level of about 85% and including at least about 530 to 543 genes. The invention further includes databases assigned a confidence level of about 90% including at least about 400 to 407 genes. Further, the invention includes databases assigned a confidence level of about 95% and including at least about 240 to 246 genes.

The transposon insertion map and database of putative essential open reading frames (ORFs) obtained may be used to confirm the essentiality of genes, for example by integration knock outs in the presence of chromosomal complementation or by integration and activation of a regulatable promoter. An "essential" gene is one that cannot be "knocked out," i.e. for which null mutants having complete absence of the gene product are not viable. This does not mean, however, that such genes could not tolerate point mutations or truncations that preserve sufficient gene product function so as to enable cell growth and survival. Essential genes are to be distinguished from "important" genes in that a "knock out" of an important gene does not lead to cell death but rather results in an attenuated growth mutant. Such genes may be included in the database of open reading frames not hit by random transposon mutagenesis as described herein, because attenuated growth colonies may be significantly smaller than the average *S. aureus* colony and may have been overlooked when transposon insertion mutants were picked to generate the high throughput transposon insertion database (HTTIM).

Nevertheless, important gene products may interact with or regulate other genes, gene products or cellular processes that are essential, thereby making such gene products appropriate targets for drug design. Moreover, most drugs do not effectively kill all the pathogenic bacteria in the body; rather, they kill or growth attenuate a portion of the bacteria, empowering the immune system to target the remainder. Hence, important genes that, when targeted with an antibacterial agent, result in attenuated growth, are also targets for the antibacterial drugs of the present invention.

Such attenuated mutants grow more slowly than wild type, and may grow more slowly due to reduced expression of an essential gene, i.e., transposon is in a gene that regulates expression of an essential gene, or due to expression of a truncated form of an essential gene, i.e., transposon is in the essential gene itself and leads to expression of a truncated mRNA. For example, mutants that show a higher drug susceptibility could be the result of insertions in a gene that potentiates resistance, such an efflux pump, or due to reduced expression of essential genes involved in the mechanism of action of the drug. Expression of mutated forms of essential and important genes may make the cell more susceptible to compounds that inhibit that particular gene or gene product, and may allow the identification of antibacterial agents with greater sensitivity. Furthermore, screening in whole cells overcomes the potential problems of uptake and efflux that are sometimes an issue for compounds identified via enzyme-based assays.

The essential and important genes of the invention may be used to design, screen for and evaluate potential antibacterial agents for the purpose of developing new treatments for *S. aureus* infection. Antibacterial agents identified according to the invention may have activity against the gene or against the corresponding gene product or metabolic pathways requiring the gene product. For instance, antibacterial agents according to the invention may include antisense nucleic acids or regulatory proteins that bind to open reading frames, to upstream polar sequences or to promoters that drive expression of the genes encoded by such open reading frames. Active agents according to the invention may also include antibodies or proteins that bind to proteins encoded by open reading frames, or to transcriptional or translational regulators of such genes or proteins, or to binding partners of such proteins. Agents may also be chemical compounds designed following molecular modeling of essential gene products according to the invention, or mutant proteins designed therefrom that compete with the essential wild type protein for reactive cell components or for interacting nutrients, as well as agents from random chemical libraries.

The present invention therefore includes methods and assays for identifying antibacterial agents having specificity for the essential or important open reading frames identified, or to genes or proteins that interact with such open reading frames or the products encoded thereby. Once essential and important open reading frames are identified, antibacterial agents may be identified using the assays and methods described herein, or by any suitable assay. Such assays may vary depending on the function delineated for each essential locus, as would be apparent to those of skill in the art. For instance, enzyme assays may be designed based on the predicted function of essential and important genes in order to define classes of inhibitors to be tested. Also, random chemical libraries may be screened for activity against the isolated genes or gene products. Cell lines may be designed or isolated that demonstrate reduced expression of essential genes, thereby providing a sensitive screening tool for inhibitors that effect the activity of that gene or gene product as it functions in the cell. Such cell lines may be devised from cells having transposon insertions that lead to attenuated growth, or may be constructed by the promoter swap techniques described herein, by using a regulatable promoter that can be used to increase gene expression, allowing for confirmation of target specificity. Here, the minimal inhibitory concentration of the inhibitor is directly related to the expression level of the target gene, such that under low expression, an attenuated growth cell is more susceptible to an inhibitor than the wild type strain, and as you raise the expression level, the minimum inhibitory concentration (MIC) increases. The MIC shift will be consistent when the inhibitor acts on the regulated target.

In addition, by targeting agents against more than one essential or important gene, the possibility of developing resistant bacterial strains is reduced.

Active agents and compounds can be formulated into pharmaceutical compounds and compositions, effective for treating and preventing *Staphylococcus* infections in accordance with the methods of the invention. Such therapy will be particularly useful in the hospital setting for preventing and treating nosocomial infections. Depending on the activity of the essential or important gene targeted, such agents could also be useful in treating all types of *Staphylococcus* infections ranging from bacteraemia and septicemia, urinary-tract infections, pneumonia and chronic lung infections, burn infections, food poisoning and other gastrointestinal infections, *Staphylococcus* associated scarlet fever, cancer, AIDS, endocarditis, dermatitis, osteochondritis, ear and eye infections, bone and joint infections, gastrointestinal infections and skin and soft tissue infections, including wound infections, pyoderma and dermatitis. Further, the invention provides pharmaceutical compositions appropriate for use in methods of treating bacterial infections described above.

In particular, the invention provides therapeutic and prophylactic vaccines for conferring therapeutic or prophylactic immunity against *Staphylococcus* infection, containing *S. aureus* antigens, fragments, motifs, antibodies specific thereto, or nucleic acid sequences encoding, optionally in association with other anti-bacterial active agents and carriers or adjuvants.

Also, the invention provides motifs of essential genes identified according to the invention which may be used to identify essential genes in other bacteria as targets to identify compounds for inhibiting or eradicating *Staphylococcus*. Further, motifs identified according to the invention may allow for inhibition of multiple essential genes.

BRIEF DESCRIPTION OF THE DRAWINGS

FIGS. 3-5 respectively contain schematics of plasmids pMOD, pMOD (Erm-1) and pMOD (Cm). FIG. 6 contains the sequence for pMOD (SEQ ID NO: 11). FIG. 7 contains the sequence for pMOD (Erm-1) (SEQ ID NO: 12). FIG. 8 contains the sequence for pMOD (Cm) (SEQ ID NO: 13).

DETAILED DESCRIPTION OF THE INVENTION

Figure 1:
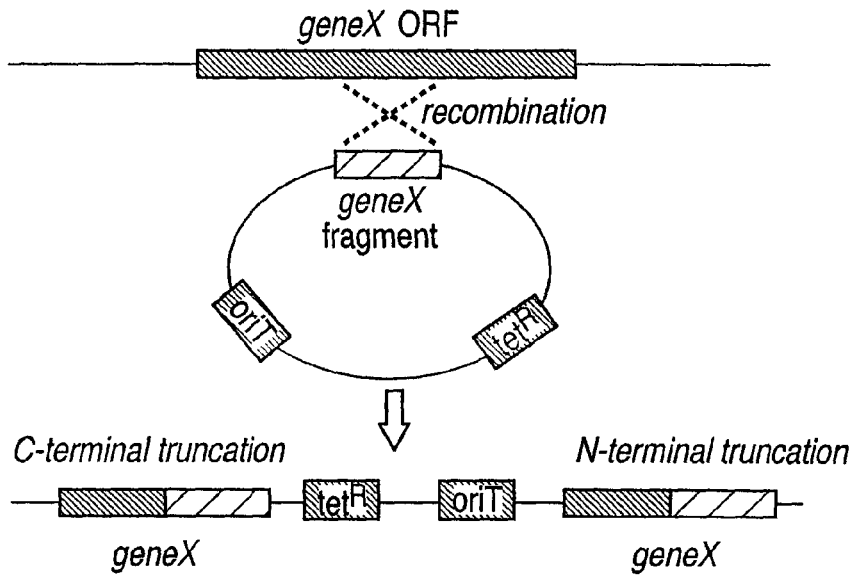
FIG. 1. Depiction of a single crossover recombination event resulting in integration of a plasmid into the bacterial chromosome. Isolation of such recombinants indicates that the targeted gene is not essential.

The essential open reading frames identified in the present invention are set forth in Table 1. These open reading frames were originally part of a library of putative nucleic acid sequences generated from S. aureus strain. The sequence of staph col, a staph aureus strain similar to RN4220, is available at the web address having the domain name tigr.org and pathname tigr-scripts/CMR2/GenomePage3.spl?database=gsa, which sequence is incorporated herein by reference. The SA Numbers in Table 1 correspond to the Tigr number system. RN4220. Nevertheless, it is expected that the genes identified will be also be essential or important in related S. aureus strains as well as other Staphylococcus species, given the low sequence diversity that exists between S. aureus strains of widely diverse environments and the pronounced structural and functional homology of gene products. Thus, it is expected that agents identified as antibacterial based on their interaction with genes or gene products S. aureus will be broadly applicable as antibacterial agents against a variety of Staphylococcus species as well as other bacteria including but not limited to Escherichia, Hemophilus, Vibrio, Borrelia, Enterococcus, Heliobacter, Legionella, Mycobacterium, Mycoplasma, Neisseria, Pseudomonas, Streptococcus, etc.

Thus, the present invention encompasses an isolated nucleic acid molecule comprising a nucleic acid sequence encoding a polypeptide having at least 80% sequence identity to a polypeptide encoded by a nucleic acid sequence selected from the group consisting of the Staphylococcus aureus open reading frames (ORFs) listed in Table 1. More preferably, the present invention encompasses an isolated nucleic acid molecule comprising a nucleic acid sequence encoding a polypeptide having at least about 85 to 90% sequence identity to a polypeptide encoded by a nucleic acid sequence selected from the group consisting of the Staphylococcus aureus open reading frames (ORFs) listed in Table 1. Even more preferably, the present invention encompasses an isolated nucleic acid molecule comprising a nucleic acid sequence encoding a polypeptide having at least about 90 to about 95% sequence identity to a polypeptide encoded by a nucleic acid sequence selected from the group consisting of the Staphylococcus aureus open reading frames (ORFs) listed in Table 1.

In particular, the invention encompasses isolated nucleic acid molecules comprising nucleic acid sequences encoding polypeptides having at least 80% sequence identity, or more preferably at least about 85 to 90 to 95% identity, to a polypeptide encoded by an essential or important nucleic acid sequence selected from the group consisting of the Staphylococcus aureus open reading frames (ORFs) listed in Table 1, wherein essentiality or importance of said nucleic acid sequence is determined by integration knock-out coupled with extra-chromosomal complementation. Likewise, the invention encompasses isolated nucleic acid molecules comprising nucleic acid sequences encoding polypeptides having at least 80% sequence identity, or more preferably at least about 85 to 90 to 95% identity, to a polypeptide encoded by an essential nuclei d sequence selected from the group consisting of the Staphylococcus aureus open reading frames (ORFs) listed in Table 1, wherein essentiality or importance of said nucleic acid sequence is determined by integration of a regulatable promoter into the gene, or via any other suitable method.

Given that the library of nucleic acid sequences encompassed in Table 1 provides an unprecedented tool useful for the identification of essential and otherwise important genes in Staphylococcus and the construction and isolation of attenuated mutants, the present invention includes a library of nucleic acid sequences consisting essentially of nucleic acid sequences having at least 70% sequence identity, or more preferably at least about 80 to 90 to 95% identity, to a nucleic acid sequence selected from the group consisting of the Staphylococcus aureus open reading frames (ORFs) listed in Table 1, wherein said library of nucleic acid sequences is employed to identify essential or otherwise important genes or to construct or isolate attenuated mutants in Staphylococcus.

Also encompassed in the invention is a map of at least about 3,000 to 6,000 transposon insertions in the genome of Staphylococcus aureus (High-Throughput Transposon Insertion Database or HTTIM), wherein said map is useful for identifying genes that are essential or important for survival of said Staphylococcus aureus, i.e., by permitting the generation of a database of open reading frames that do not contain a transposon insertion.

Thus, the databases and libraries disclosed herein may be used to formulate useful subsets of these libraries and databases. Accordingly, the invention includes subsets of the databases and libraries disclosed. Moreover, such a group of mutants identified from the HTTIM database of transposon hits provides a useful subset database for comparing homologies with essential genes of other organisms, for computer modeling of potential antibacterial agents, etc. A particularly useful database subset is one containing essential genes from S. aureus that are also identified as essential in other Gram negative or Gram positive bacteria. Indeed, genes that have essential homologs in other bugs are likely to provide useful targets for broad spectrum antibacterial agents, i.e., agents that have broad spectrum activity as an antibacterial agent.

Further, the databases and subset databases of the present invention may also be used as comparative tools with other like databases or database subsets to identify broad spectrum. For instance, particularly envisioned is an embodiment wherein the database of putative essential genes identified in S. aeureus is cross-referenced with a similar database formed from Pseudomonas aeruginosa, wherein homologues present in both databases signal a potential target for a broad spectrum antibacterial agent. Cross-referencing between P. aeruginosa and S. aureus in particular will identify antibacterial targets for identifying broad spectrum antibiotics active against both Gram negative and Gram positive bacteria. However, databases derived from any bacteria could be employed in such comparisons, as well as databases formed from yeast, fungi, mycoplasma, and other potential pathogens.

Also encompassed in the invention is the use of essential and important genes and the corresponding proteins expressed thereto in the design of vaccines for eliciting prophylactic or therapeutic immune responses against S. aureus.

Such vaccines will typically comprise a S. aureus protein antigen or fragment or derivative thereof encoded by an essential or important gene. Preferably, the protein antigen expressed from a recombinant polynucleotide. Additionally, such antigens will preferably be a protein expressed on the surface of the bacteria.

Where the invention is directed to a fragment of a protein encoded by an essential or important gene, said fragment is preferably at least 8 to 12 amino acids long, and even more preferably at least about 20 to 30 amino acids long. Preferably, the fragment comprises either a B cell or a T cell epitope.

Where the invention is directed to a derivative of a protein encoded by an essential or important gene, said derivative may contain one or more amino acid substitutions, additions or deletions. Preferably, the amino acid substitutions are conservative amino acid replacements. Conservative amino acid replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonably predictable that an isolated replacement of a leucine with an isoleucine or valine, an asparate with glutamate, a threonine with a serine, or a similar conservative replacement of an amino acid with a structurally related amino acid will not have a major effect on the biological activity. Polypeptide molecules having substantially the same amino acid sequence as the protein by possessing minor amino acid substitutions that do not substantially affect the functional aspects are encompassed with the scope of derivatives of the proteins of the invention.

The polypeptide fragment or derivative is preferably immunologically identifiable with the polypeptide encoded by the essential or important gene. The polypeptide fragment or derivative is preferably immunogenic and is able to cause a humoral and/or cellular immune response, either alone or when linked to a carrier, in the presence or absence of an adjuvant. The polypeptide fragment or derivative may be fused to or incorporated into another polypeptide sequence. This other polypeptide sequence may include one or more other proteins, fragments or derivatives thereof encoded by an essential or important gene. The other polypeptide sequence may also include a polypeptide sequence which allows for presentation of the polypeptide fragment or derivative.

Accordingly, the present invention encompasses an isolated polypeptide and fragments and derivatives thereof, wherein said polypeptide has at least 80% sequence identity to a polypeptide encoded by a nucleic acid sequence selected from the group consisting of the S. aureus open reading frames (ORFs) listed in Table 1. More preferably, the present invention encompasses an isolated polypeptide and fragments and derivatives thereof, wherein said polypeptide has at least about 85 to 90% sequence identity to a polypeptide encoded by a nucleic acid sequence selected from the group consisting of the S. aureus open reading frames (ORFs) listed in Table 1. Even more preferably, the present invention encompasses an isolated polypeptide and fragments and derivatives thereof, wherein said polypeptide has at least about 90% to about 95% sequence identity to a polypeptide encoded by a nucleic acid sequence selected from the group consisting of the S. aureus open reading frames (ORFs) listed in Table 1.

In particular, the invention encompasses isolated polypeptides and fragments and derivatives thereof, wherein said polypeptides have at least 80% sequence identity, or more preferably at least about 85 to 90 to 95% identity, to a polypeptide encoded by an essential or important nucleic acid sequence selected from the group consisting of the S. aureus open reading frames (ORFs) listed in Table 1, wherein the essentiality or importance of said nucleic acid sequence is determined by integration knock-out couple with extra-chromosomal complementation. Likewise, the invention encompasses isolated polypeptides and fragments and derivatives thereof, wherein said polypeptides have at least 80% sequence identify, or more preferably at least about 85 to 90 to 95% identity, to a polypeptide encoded by an essential nucleic acid sequence selected from the group consisting of the S. aureus open reading frames (ORFs) listed in Table 1, wherein essentiality or importance of said nucleic acid sequence is determined by integration of a regulatable promoter into the gene, or via any other suitable method.

Also encompassed in the invention are therapeutic and prophylactic vaccines that comprise ligands that specifically bind antigens encoded by essential or important genes identified according to the invention, for use in, for instance, passive immunization. Preferred ligands are antibodies and antibody fragments that specifically bind the antigen encoded by the essential gene. Such antibodies may be polyclonal or monoclonal. Types of antibodies and antibody fragments include by way of examples murine antibodies, chimeric, antibodies, humanized antibodies, Fab fragments, $Fab_2$ fragments and human antibodies and scFv's. Methods for producing antibodies and antibody fragments by recombinant and non-recombinant methods are well known to those skilled in the art. In some embodiments the antigen used in such passive immunization may be attached to a cytotoxic moiety, e.g., a radionuclide or other agent that is cytotoxic against the bacteria.

Further encompassed within the scope of the invention are cells or viral vectors that express on their surface a S. aureus essential gene, fragment or variant identified according to the invention.

In the case of prophylactic vaccines, the vaccine will comprise an immunogenic composition comprising a prophylactically effective amount of an antigen, antibody, cells or vector expressing an antigen encoded by an essential or important gene and will be formulated such that upon administration it elicits a protective immune response. In the case of therapeutic vaccines, the vaccine will comprise an immunogenic compostiion comprising a therapeutically effective amount of an antigen, antibody, cells or vectors expressing an antigen encoded by an essential or important gene and will be formulated such that upon administration it elicits a therapeutic immune response. Dosage effective amounts of prophylactic and therapeutic vaccines will be determined by known methods and will typically vary from about 0.00001 g/kg body weight to about 5-10 g/kg body weight.

The immunogenic compositions of the invention can be administered by known methods, i.e., mucosally or parenterally.

Suitable routes of mucosal administration include oral, intranasal (IN), intragastric, pulmonary, intestinal, rectal, ocular, and vaginal routes. Preferably, mucosal administration is oral or intranasal.

Where mucosal administration is used, the immunogenic composition is preferably adapted for mucosal administration. For instance, where the composition is administered orally, it may be in the form of tablets or capsules (optionally enteric-coated), liquid, transgenic plants, etc. Where the composition is administered intranasally, it may be in the form of a nasal spray, nasal drops, gel or powder. Where the antigen composition is adapted for mucosal administration, it may further be formulated such that the antigen remains stable, for instance by the use of carriers and excipients.

The immunogenic compositions of the invention can further comprise a mucosal adjuvant. Mucosal adjuvants suitable for use in the invention include (a) E. coli beat-labile enterotoxin ("LT"), or detoxified mutants thereof, such as the K63 or R72 mutants; (B) cholera toxin ("CT"), or detoxified mutants thereof; or (C) microparticles (i.e., a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone etc.); (D) a polyoxyethylene ether or a polyoxyethylene ester (see International patent application WO 99/52549); (E) a polyoxyethylene sorbitan ester surfactant in combination with an octoxynol (see International patent application WO 01/21207) or a polyoxyethylene alkyl ether or ester surfactant in combination with at least one additional non-ionic surfactant such as an octoxynol (see International patent application WO 01/21152); (F) chitosan (e.g. International patent application WO 99/27960) and (G) an immunostimulatory oligonucleotide (e.g. a CpG oligonucleotide) and a saponin (see International patent application WO 00/62800). Other mucosal adjuvants are also available (e.g. see chapter 7 of Vaccine design: the subunit and adjuvant approach, eds. Powell & Newman, Plenum Press 1995 (ISBN 0-306-44867-X).

Mutants of LT are preferred mucosal adjuvants, in particular the "K63" and "R72" mutants (e.g. see International patent application WO 98/18928), as these result in an enhanced immune response.

Microparticles are also preferred mucosal adjuvants. These are preferably derived from a poly(α-hydroxy acid), in particular, from a poly(lactide) ("PLA"), a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered antigen.

Antigen may be entrapped within the microparticles, or may be adsorbed to them. Entrapment within PLG microparticles is preferred. PLG microparticles are discussed in further detail in Morris et al., (1994), Vaccine, 12:5-11, in chapter 13 of Mucosal Vaccines, eds. Kiyono et al., Academic Press 1996 (ISBN 012410587), and in chapters 16 & 18 of Vaccine design: the subunit and adjuvant approach, eds. Powell &Newman, Plenum Press 1995 (ISBN 0-306-44867-X).

LT mutants may advantageously be used in combination with microparticle-entrapped antigen, resulting in significantly enhanced immune responses.

Suitable routes of parenteral administration include intramuscular (IM), subcutaneous, intravenous, intraperitoneal, intradermal, transcutaneous, and transdermal (see e.g., International patent application WO 98/20734) routes, as well as delivery to the interstitial space of a tissue.

The immunogenic compositions of the invention may be adapted for parenteral administration (e.g., in the form of an injectable, which will typically be sterile and pyrogen-free).

The immunogenic composition may further comprise a parenteral adjuvant. Parenteral adjuvants suitable for use in the invention include: (A) aluminum compounds (e.g. aluminum hydroxide, aluminum phosphate, aluminum hydroxyphosphate, oxyhydroxide, orthophosphate, sulfate etc. (e.g. see chapters 8 & 9 of Vaccine design: the subunit and adjuvant approach, eds. Powell & Newman, Plenum Press 1995 (ISBN 0-306-44867-X) (hereinafter "Vaccine design"), or mixtures of different aluminum compounds, with the compounds taking any suitable form (e.g. gel, crystalline, amorphous etc.), and with adsorption being preferred; (B) MF59™ (5% Squalene, 0.5% TWEEN®-80 (polyoxyethylenesorbitan, monooleate), and 0.5% SPAN®85 (sorbitan trioleate), formulated into submicron particles using a microfluidizer) (see Chapter 10 of Vaccine design; see also International patent application WO 90/14837); (C) liposomes (see Chapters 13 and 14 of Vaccine design); (D) ISCOMs (see Chapter 23 of Vaccine design); (E) SAF, containing 10% Squalane, 0.4% TWEEN®-80 (polyoxyethylenesorbitan, monooleate), 5% PLURONIC™L121 (block copolymer of propylene oxide and ethylene oxide), and thr-MDP, either microfluidized into a submicron emulsion or vortexed to generate a larger particle size emulsion (see Chapter 12 of Vaccine design); (F) Ribi™ adjuvant system (RAS), (Ribi Immunochem) containing 2% Squalene, 0.2% TWEEN®-80(polyoxyethylenesorbitan, monooleate), and one Or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 (see Chapter 22 of Vaccine design), also known as Stimulon™; (H) ISCOMs, which may be devoid of additional detergent (International patent application WO 00/07621); (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. (see Chapters 27 & 28 of Vaccine design); (K) microparticles (see above); (L) monophosphoryl lipid A (MPL) or 3-O-deacylated MPL (3dMPL) (e.g. chapter 21 of Vaccine design); (M) combinations of 3dMPL with, for example, QS21 and/or oil-in-water emulsions (European patent applications 0835318, 0735898 and 0761231); (N) oligonucleotides comprising CpG motifs (see Krieg (2000) Vaccine, 19:618-622; Krieg (2001) Curr. Opin. Mol. Ther., 2001, 3:35-24; WO 96/02555, WO 98/16247, WO 98/18810, WO 98/40100, WO 98/55495, WO 98/37919 and WO 98/52581, etc.) i.e. containing at least one CG dinucleotide, with 5-methylcytosine optionally being used in place of cytosine; (O) a polyoxyethylene ether or a polyoxyethylene ester (International patent application WO 99/52549); (P) a polyoxyethylene sorbitan ester surfactant in combination with an octoxynol (International patent application WO 01/21207) or a polyoxyethylene alkyl ether or ester surfactant in combination with at least one additional non-ionic surfactant such as an octoxynol (International patent application WO 01/21152); (Q) an immunostimulatory oligonucleotide (e.g. a CpG oligonucleotide) and a saponin (International patent application WO 00/62800); (R) an immunostimulant and a particle of metal salt (International patent application WO 00/23105); (S) a saponin and an oil-in-water emulsion (International patent application WO 99/11241); (T) a saponin (e.g. QS21)+3dMPL+IL-12 (optionally+a sterol) (International patent application WO 98/57659); and (U) other substances that act as immunostimulating agents to enhance the effectiveness of the composition (e.g. see Chapter 7 of Vaccine design).

Aluminium compounds and MF59™ are preferred adjuvants for parenteral use.

The immunognic compositions of the invention may be administered in a single dose, or as part of an administration regime. The regime may include priming and boosting doses, which may be administered mucosally, parenterally, or various combinations thereof.

In some instances the vaccines of the invention may comprise several antigens, fragments or variants encoded by essential genes identified according to the invention. Alternatively, the vaccine may further comprise antigens identified by other methods, or specific to other bacteria, e.g., in order to provide multivalent vaccines.

With respect to libraries according to the invention, a library of polynucleotides or a library of transposon insertion sites is a collection of sequence information, which information is provided in either biochemical form (e.g., as a collection of polynucleotide molecules), or in electronic form (e.g., as a collection of polynucleotide sequences stored in a computer-readable form, as in a computer system and/or as part of a computer program). The sequence information of the polynucleotides can be used in a variety of ways, for instance as a resource for gene discovery, i.e., for identifying and verifying essential and important genes in *Staphylococcus aureus*, or for identifying essential or important homologues in other genera or species. A polynucleotide sequence in a library can be a polynucleotide that represents an mRNA, polypeptide, or other gene product encoded by the polynucleotide, and accordingly such a polynucleotide library could be used to formulate corresponding RNA or amino acid libraries according to the sequences of the library members.

The nucleotide sequence information of the library can be embodied in any suitable form, e.g., electronic or biochemical forms. For example, a library of sequence information embodied in electronic form comprises an accessible computer data file (or, in biochemical form, a collection of nucleic acid molecules) that contains the representative nucleotide sequences of essential and important genes and/or insertion mutants that are differentially expressed (e.g., attenuated growth mutants). Other combinations and comparisons of cells affected by various diseases or stages of disease will be readily apparent to the ordinarily skilled artisan. Biochemical embodiments of the library include a collection of nucleic acids that have the sequences of the genes or transposon insertion sites in the library, where the nucleic acids can correspond to the entire gene in the library or to a fragment thereof, as described in greater detail below.

The polynucleotide libraries of the subject invention generally comprise sequence information of a plurality of polynucleotide sequences, where at least one of the polynucleotides has a sequence of any of the sequences in Table 1. By plurality is meant at least 2, usually at least 3 and can include up to all of the sequences included in these tables. The length and number of polynucleotides in the library will vary with the nature of the library, e.g., if the library is an oligonucleotide array, a cDNA array, a computer database of the sequence information, etc.

Where the library is an electronic library, the nucleic acid sequence information can be present in a variety of media. "Media" refers to a manufacture, other than an isolated nucleic acid molecule, that contains the sequence information of the present invention. Such a manufacture provides the genome sequence or a subset thereof in a form that can be examined by means not directly applicable to the sequence as it exists in a nucleic acid. For example, the nucleotide sequence of the present invention, e.g. the nucleic acid sequences of any of the polynucleotides of identified in Table 1, can be recorded on computer readable media, e.g. any medium that can be read and accessed directly by a computer. Such media include, but are not limited to: magnetic storage media, such as a floppy disc, a bard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc. In addition to the sequence information, electronic versions of the libraries of the invention can be provided in conjunction or connection with other computer-readable information and/or other types of computer-readable files (e.g., searchable files, executable files, etc, including, but not limited to, for example, search program software, etc.).

By providing the nucleotide sequence in computer readable form, the information can be accessed for a variety of purposes. Computer software to access sequence information is publicly available. For example, the gapped BLAST (Altschul et al. *Nucleic Acids Res*. (1997) 25:3389-3402) and BLAZE (Brutlag et al. *Comp. Chem*. (1993) 17:203) search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

"Search means" refers to one or more programs implemented on the computer-based system, to compare a target sequence or target structural motif, or expression levels of a polynucleotide in a sample, with the stored sequence information. Search means can be used to identify fragments or regions of the genome that match a particular target sequence or target motif. A variety of known algorithms are publicly known and commercially available, e.g. MacPattern (EMBL), BLASTN and BLASTX (NCBI). A "target sequence" can be any polynucleotide or amino acid sequence of six or more contiguous nucleotides or two or more amino acids, preferably from about 10 to 100 amino acids or from about 30 to 300 nucleotides. A variety of comparing means can be used to accomplish comparison of sequence information from a sample (e.g., to analyze target sequences, target motifs, or relative expression levels) with the data storage means. A skilled artisan can readily recognize that any one of the publicly available homology search programs can be used as the search means for the computer based systems of the present invention to accomplish comparison of target sequences and motifs. Computer programs to analyze expression levels in a sample and in controls are also known in the art.

A "target structural motif," or "target motif," refers to any rationally selected sequence or combination of sequences in which the sequence(s) are chosen based on a three-dimensional configuration that is formed upon the folding of the target motif, or on consensus sequences of regulatory or active sites. There are a variety of target motifs known in the art. Protein target motifs include, but arc not limited to, enzyme active sites and signal sequences. Nucleic acid target motifs include, but are not limited to, hairpin structures, promoter sequences and other expression elements such as binding sites for transcription factors.

A variety of structural formats for the input and output means can be used to input and output the information in the computer-based systems of the present invention. One format for an output means ranks the relative expression levels of different polynucleotides. Such presentation provides a skilled artisan with a ranking of relative expression levels to determine a gene expression profile.

As discussed above, the "library" as used herein also encompasses biochemical libraries of the polynucleotides of Table 1, e.g., collections of nucleic acids representing the provided polynucleotides. The biochemical libraries can take a variety of forms, e.g., a solution of cDNAs, a pattern of probe nucleic acids stably associated with a surface of a solid support (i.e., an array) and the like. Of particular interest are nucleic acid arrays in which one or more of the sequences identified in Table 1 is represented on the array. By "array" is meant an article of manufacture that has at least a substrate with at least two distinct nucleic acid targets on one of its surfaces, where the number of distinct nucleic acids can be considerably higher, typically being at least 10 nt, usually at least 20 nt and often at least 25 nt. A variety of different array formats have been developed and are known to those of skill in the art. The arrays of the subject invention find use in a variety of applications, including gene expression analysis, drug screening, mutation analysis and the like, as disclosed in the above-listed exemplary patent documents.

In addition to the above nucleic acid libraries, analogous libraries of polypeptides are also provided, where the polypeptides of the library will represent at least a portion of the polypeptides encoded by a gene corresponding to one or more of the sequences identified in Table 1.

"Identity" as it is used in the present invention should be distinguished from "homology" or "homologous." In the context of the coding sequences and genes of this invention, "homologous" refers to genes whose expression results in expression products which have a combination of amino acid sequence similarity (or base sequence similarity for transcript products) and functional equivalence, and are therefore homologous genes. In general such genes also have a high level of DNA sequence similarity (i.e., greater than 80% identity when such sequences are identified among members of the same genus, but lower when these similarities are noted across bacterial genera), but are not identical. Relationships across bacterial genera between homologous genes are more easily identified at the polypeptide (i.e., the gene product) rather than the DNA level. The combination of functional equivalence and sequence similarity means that if one gene is useful, e.g., as a target for an antibacterial agent, or for screening for such agents, then the homologous gene is probably also useful, but may not react in the same manner or to the same degree to the activity of a specific antibacterial agent.

Nevertheless, the identification of one such gene serves to identify a homologous gene through the same relationships as indicated above, and can serve as a starting point to determine whether the homologous gene is also essential, whether it responds to the same antibacterial agents, etc. Typically, such homologous genes are found in other bacterial species, especially, but not restricted to, closely related species. Due to the DNA sequence similarity, homologous genes are often identified by hybridizing with probes from the initially identified gene under hybridizing conditions that allow stable binding under appropriately stringent conditions. For instance, nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., bind to the provided polynucleotide sequences under stringent hybridization conditions. By using probes, particularly labeled probes of DNA sequences, one can isolate homologous or related or substantially identical genes. The equivalent function of the product is then verified using appropriate biological and/or biochemical assays.

Using such hybridization technique for the identification of homologous genes, it will be possible to screen other species of bacteria, particularly other genera of gram positive pathogenic bacteria although gram negative bacteria may also be screened, to determine if any essential or important gene identified herein has a homologue in that particular genus of bacteria. If so, such gene could be cloned and isolated for essentiality in the particular genus, and further tested for sensitivity or susceptibility to the antibacterial agents and inhibitors identified herein. Specific genera of bacteria particularly appropriate for hybridization screening for the presence of homologues of essential and important genes include *Escherichia, Hemophilus, Vibrio, Borrelia, Enterococcus, Heliobacter, Legionella, Mycobacterium, Mycoplasma, Neisseria, Pseudomonas, Streptococcus*, etc.

"Identity," on the other hand, is gauged from the starting point of complete homology. Thereafter, identity may be described in terms of percentages according to the number of base changes in the DNA sequence taking into account any gaps. For purposes of the present invention, variants of the invention have a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). A preferred method of calculating percent identity is the Smith-Waterman algorithm, using the following. Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Amino acid sequence variants are also included in the invention. Preferably, naturally or non-naturally occurring protein variants have amino acid sequences which are at least 85%, 90%, or 95% identical to the amino acid sequences identified herein, or to a shorter portion of these sequences. More preferably, the molecules are 98% or 99% identical. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* (1981) 2:482-489.

Also included in the invention are fragments of the nucleic acid sequences and amino acid sequences identified herein, as well as RNAs and RNA fragments corresponding to the DNA sequences disclosed. Such nucleic acid fragments are at least about 10 nucleotides, more preferably at least about 20 to 25 nucleotides, and more preferably at least about 50 to 100 nucleotides, and can include any fragment or variant of a fragment. Such nucleic acid fragments may be used as probes for identifying similar or substantially identical or identical nucleic acid sequences in other genera, or as tools in constructing nucleic acid vectors for knock out and promoter swap experiments. Such amino acid fragments are at least about four amino acids in length, more preferably at least about 8 to 12 amino acids in length, and more preferably at least about 20 to 30 amino acids in length, and may be used as agonists or antagonists to test binding interactions of the proteins disclosed herein, or alternatively as immunogens to isolate antibodies that recognize and bind to specific epitopes of a target protein.

Once a gene is identified as being essential or important for *Staphylococcus* growth on rich media or in any specific environment, the invention also encompasses the identification of antibacterial agents that have specific activity against the essential or important genes or their gene products or the biochemical pathways in which they are involved. In this context, the term "biochemical pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway.

Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene. An "expression product" of a gene means that, in a bacterial cell of interest, the gene is transcribed to form RNA molecules. For those genes that are transcribed into mRNAs, the mRNA is translated to form polypeptides. More generally, in this context, "expressed" means that a gene product is formed at the biological level that would normally have the relevant biological activity (i.e., RNA or polypeptide level).

Thus, the invention includes a method of screening for an antibacterial agent, comprising determining whether a test compound is active against an essential or important bacterial gene identified by the methods herein. The invention also includes a method of screening for an antibacterial agent, comprising determining whether a test compound is active against a protein encoded by an essential bacterial gene identified herein, or active to inhibit the biochemical pathway that involves said protein. The term "antibacterial agent" refers to both naturally occurring antibiotics produced by microorganisms to suppress the growth of other microorganisms, and agents synthesized or modified in the laboratory which have either bactericidal or bacteriostatic activity. An "active" agent in this context will inhibit the growth of *S. aureus* and possibly related species. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half life, etc. to compounds in order to correlate enzyme inhibition with growth inhibition.

Assays may include any suitable method and may be expected to vary on the type of essential gene or protein involved. For instance, one embodiment is a method comprising the steps of:
a) contacting said protein or a biologically active fragment thereof with a test compound; and
b) determining whether said test compound binds to said essential gene product or protein or fragment of said protein;
wherein binding of said test compound to said polypeptide or said fragment is indicative that said test compound is an antibacterial agent. It is quite common in identifying antibacterial agents, to assay for binding of a compound to a particular polypeptide where binding is an indication of a compound which is active to modulate the activity of the polypeptide. Binding may be determined by any means according to the agent tested and techniques known in the art.

Also, agents that inhibit binding of two proteins or polypeptides may also be identified, for instance using a yeast two-hybrid system. Such a system will entail cloning the genes encoding each protein and expressing each in a reporter cell system such that interaction between the two proteins is monitored by observing the expression of a reporter gene. For instance, cDNAs cloned in a yeast two-hybrid expression system (Chien et al. (1991) Proc. Natl. Acad. Sci. (U.S.A.) 88: 9578; Zervos et al. (1993) Cell 72: 233) can be used to identify other cDNAs encoding proteins that interact with the protein encoded by the first, thereby produce expression of the GAL4-dependent reporter gene. Thereafter, cells expressing both proteins leading to expression of the reporter gene are used to screen for agents that interact with either protein, or the gene encoding either protein. Such systems are well known in the art and are well within the realm of ordinary skill.

Another embodiment is a method for evaluating a test agent for inhibition of expression of an essential gene identified according to the methods herein, comprising:
a) contacting a cell expressing said essential gene with said agent; and
b) determining the amount or level of expression of said essential gene in said sample.
The exact determination method will be expected to vary depending on the characteristics of the expression product as would be readily apparent to one of ordinary skill in the art. Such methods can include, for example, antibody binding methods, enzymatic activity determinations, and substrate analog binding assays. Such level of expression could be monitored by monitoring the level of the product of the essential gene in the cell, i.e., by SDS-PAGE, or by calorimetric assays using, for example, a lacZ gene or protein fusion and detection on media using X-Gal or spectrophotometric detection.

When such fusions are employed, fusions may be designed using the chromosomal gene so long as the fusion does not disrupt the function of the essential gene, i.e., as with a gene fusion where lacZ is inserted just downstream of the essential gene and is expressed from the same promoter as the essential gene. Alternatively, one could employ an extrachromosomal fusion construct whereby the wild type chromosomal copy of the gene is not disrupted. In this case, one could employ a protein fusion, i.e., where a portion of lacZ sufficient to be detected with a colorimetric test is fused in frame with the coding region of the essential gene such that a fusion protein is obtained. Other detectable or measurable proteins commonly used in the art may be used as an alternative to lacZ, for instance, phoA, Lux/luciferase, etc.

Another method of the invention for evaluating an potential antibacterial agent, comprises the steps of:
a) providing a bacterial strain comprising a mutant or normal form of the essential or important gene, wherein said mutant form of the gene confers a growth conditional phenotype;
b) contacting bacteria of said bacterial strain with a test compound in semi-permissive or permissive growth conditions; and
c) determining whether the growth of said bacterial strain comprising said mutant form of a gene is reduced in the presence of said test compound to a greater extent than a comparison bacteria comprising a normal form of said gene.

In this context, a "mutant form" of a gene is a gene which has been altered, either naturally or artificially, changing the base sequence of the gene, which results in a change in the amino acid sequence of an encoded polypeptide. The change in the base sequence may be of several different types, including changes of one or more bases for different bases, small deletions, and small insertions. Mutations may also include transposon insertions that lead to attenuated activity, i.e., by resulting in expression of a truncated protein. By contrast, a normal form of a gene is a form commonly found in a natural population of a bacterial strain. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the bacterial strain having that gene, while a mutant form of a gene suitable for use in these methods does provide such a growth conditional phenotype.

As used in the present disclosure, the term "growth conditional phenotype" indicates that a bacterial strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a bacterial strain having a heat-sensitive phenotype) exhibits significantly reduced growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes. A growth conditional phenotype can also be conferred by cloning an essential or important gene behind a regulatable promoter, for instance, a promoter that is only active, or only leads to transcription, under particular environmental conditions or in response to a specific environmental stimulus. Such growth conditional promoter mutants may be isolated according to the promoter swap strategies described herein.

"Semi-permissive conditions" are conditions in which the relevant culture parameter for a particular growth conditional phenotype is intermediate between permissive conditions and non-permissive conditions. Consequently, in semi-permissive conditions the bacteria having a growth conditional phenotype will exhibit growth rates intermediate between those shown in permissive conditions and non-permissive conditions. In general, such intermediate growth rate is due to a mutant cellular component which is partially functional under semi-permissive conditions, essentially fully functional under permissive conditions, and is non-functional or has very low function under non-permissive conditions, where the level of function of that component is related to the growth rate of the bacteria.

The term "method of screening" means that the method is suitable, and is typically used, for testing for a particular property or effect in a large number of compounds. Therefore, the method requires only a small amount of time for each compound tested; typically more than one compound may be tested simultaneously (as in a 96-well microtiter plate, or in a series of replica plates), and preferably significant portions of the procedure can be automated. "Method of screening" also refers to determining a set of different properties or effects of one compound simultaneously.

Because the essential and important genes identified herein can be readily isolated and the genes cloned into a variety of vectors known in the art, the invention also encompasses vectors comprising the nucleic acid sequences, open reading frames and genes of the invention, as well as host cells containing such vectors. Because the essential genes identified herein can be readily isolated and the encoded gene products expressed by routine methods, the invention also provides the polypeptides encoded by those genes, as well as genes having at least about 50%, or more preferably about 60%, or more preferably about 70%, or more preferably about 80%, or more preferably about 90%, or most preferably about 95% protein sequence identity.

Thus, by identifying certain essential and/or important genes, this invention provides a method of screening for an antibacterial agent by contacting a polypeptide encoded by one of the identified essential or important genes, or a biologically active fragment of such a polypeptide, with a test compound, and determining whether the test compound binds to the polypeptide or polypeptide fragment. In addition, to simple binding determinations, the invention provides a method for identifying or evaluating an agent active on one of the identified essential genes. The method involves contacting a sample containing an expression product of one of the identified genes with the known or potential agent, and determining the amount or level of activity of the expression product in the sample.

In particular, antibodies to essential and important gene products are anticipated to be suitable diagnostic binding and antibacterial agents. Thus, antibodies to the proteins encoded by the essential and important genes identified by the methods described herein are also included in the invention. Such antibodies may be isolated according to well known techniques in the art, i.e., Kohler and Milstein for monoclonal antibodies. Also included are polyclonal antibodies and antibody fragments such as Fv, Fab and $Fab_2$ fragments, as well as chimeric and humanized antibodies, and human antibodies, i.e., made using a Xeno mouse.

In a further aspect, this invention provides a method of diagnosing the presence of a bacterial strain having one of the genes identified above, by probing with an oligonucleotide at least 15 nucleotides in length, which specifically hybridizes to a nucleotide sequence which is the same as or complementary to the sequence of one of the bacterial genes identified above. In some cases, it is practical to detect the presence of a particular bacterial strain by direct hybridization of a labeled oligonucleotide to the particular gene. In other cases, it is preferable to first amplify the gene or a portion of the gene before hybridizing labeled oligonucleotides to those amplified copies.

In a related aspect, this invention provides a method of diagnosing the presence of a bacterial strain by specifically detecting the presence of the transcriptional or translational product of the gene. Typically, a transcriptional (RNA) product is detected by hybridizing a labeled RNA or DNA probe to the transcript. Detection of a specific translational (protein) product can be performed by a variety of different tests depending on the specific protein product. Examples would be binding of the product by specific labeled antibodies and, in some cases, detection of a specific reaction involving the protein product. Diagnostic assays find particular use in assaying tissue and fluid samples of patients suspect of having a *Staphylococcus* infection.

Antibacterial agents identified according to the methods of the invention may be employed in pharmaceutical compositions. Such compositions may be administered to patients in order to treat an infection by or involving *S. aureus*, either alone or in combination with secondary agents targeted at, for instance virulence factors of *S. aureus*, or other bacteria that may be present in addition to *S. aureus*. In this context, the term "administration" or "administering" refers to a method of giving a dosage of an antibacterial pharmaceutical composition to a mammal, where the method is, e.g., topical, oral, intranasal, inhaled, intravenous, transdermal, intraperitoneal, or intramuscular. The preferred method of administration can vary depending on various factors, e.g., the components of the pharmaceutical composition, the site of the potential or actual bacterial infection, the bacterium involved, and the severity of an actual bacterial infection.

As used above and throughout this application, "hybridize" has its usual meaning from molecular biology. It refers to the formation of a base-paired interaction between nucleotide polymers. The presence of base pairing implies that at least an appreciable fraction of the nucleotides in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

The term, "DNA molecule", should be understood to refer to a linear polymer of deoxyribonucleotides, as well as to the linear polymer, base-paired with its complementary strand, forming double-strand DNA (dsDNA). The term is used as equivalent to "DNA chain" or "a DNA" or "DNA polymer" or "DNA sequence", so this description of the term meaning applies to those terms also. The term does not necessarily imply that the specified "DNA molecule" is a discrete entity with no bonding with other entities. The specified DNA molecule may have H-bonding interactions with other DNA molecules, as well as a variety of interactions with other molecules, including RNA molecules. In addition, the specified DNA molecule may be covalently linked in a longer DNA chain at one, or both ends. Any such DNA molecule can be identified in a variety of ways, including, by its particular nucleotide sequence, by its ability to base pair under stringent conditions with another DNA or RNA molecule having a specified sequence, or by a method of isolation which includes hybridization under stringent conditions with another DNA or RNA molecule having a specified sequence.

References to a "portion" of a DNA or RNA chain mean a linear chain which has a nucleotide sequence which is the same as a sequential subset of the sequence of the chain to which the portion refers. Such a subset may contain all of the sequence of the primary chain or may contain only a shorter sequence. The subset will contain at least 15 bases in a single strand. However, by "same" is meant "substantially the same"; deletions, additions, or substitutions of specific nucleotides of the sequence, or a combination of these changes, which affect a small percentage of the full sequence will still leave the sequences substantially the same. Preferably this percentage of change will be less than 20%, more preferably less than 10%, and even more preferably less than 3%. "Same" is therefore distinguished from "identical"; for identical sequences there cannot be any difference in nucleotide sequences.

As used in reference to nucleotide sequences, "complementary" has its usual meaning from molecular biology. Two nucleotide sequences or strands are complementary if they have sequences that would allow base pairing between the strands according to the usual pairing rules. This does not require that the strands would necessarily base pair at every nucleotide; two sequences can still be complementary with a low level of base mismatch such as that created by deletion, addition, or substitution of one or a few (up to 5 in a linear chain of 25 bases) nucleotides, or a combination of such changes.

Other embodiments of the invention will be immediately envisaged by those of skill in the art upon reading the methods and examples to follow. Such examples are merely illustrative of the invention, and should not be construed as limiting the scope of the invention in any way.

A. Methodology

The following methods are used for generating transposon libraries in *S. aureus*. It should be emphasized that these methods are exemplary of methods which may be used to identify and map *S. aureus* essential genes and to construct a database of *S. aureus* essential genes according to the invention. In particular, is should be understood that modification of these particular methods and protocols is within the scope of the invention and within the purview of the ordinary skilled artisan.

1. Method for Obtaining Electrocompetent *S. aureus*

An overnight culture of *S. aureus* was diluted 1 to 25 in B2 broth, pH 7.0 [1] and shaken at 37° C. until the culture reached mid log phase, an $OD_{600}$ 0.6-0.8. The cells were then chilled on ice and washed with 500 mM sucrose as described by Iandolo et Al. [2]. However the centrifuge condition of the procedure is modified to, 10,000 g for 20 minutes. The final cell pellet is resuspended in a cold sucrose solution and immediately frozen at −0 C as 35 ul aliquots.

2. Transposon Construction

TN5 transposons are prepared using EZ:: TN™pMOD<MCS> Transposon Construction Vector and EZ::TN™ Transposase (Epicentre Technologies, Madison, Wis.). Initially two separate transposomes are designed using either chloramphenicol or erythromycin markers. Although both are successful in producing transposon mutants, the majority of the library is the result of the erythormycin transposon as it produces more mutants per electroporation. The choloramphenicol marker is amplified from plasmid pC194 and cloned into the pMOD™<MCS>. Amplifications from pC194 are performed using the primers Cm194-HindF (5'-TATATaagcttGTTACAGTAATATTGACTTT-3') (SEQ ID NO: 1) and Cm194-KpnR (5'-TAACGggtaccGTrAGTGA-CATTAGAAAACC-3') (SEQ ID NO: 2). The erythromycin marker is amplified from plasmid pTLV-1 using the primers Erm917-HindF (5'-AAATaagcttTAGAAGCAAACTTAA-GAGTG-3') (SEQ ID NO: 3) and Erm9117-KpnR (5'CG-GTCGTTATggtaccATTCAAATTTATCC-3') (SEQ ID NO: 4). Each primer contains a restriction enzyme site, designated in lower case above, for cloning. The antibiotic markers are amplified from their respective plasmids under the following conditions: 94° C. for 1 minute followed by 30 cycles of 94° C. for 1 min 30 sec, 60° C. for 45 sec and 72° C. for 1 min with a final extension time of 5 min. The markers are then cloned into the MCS of plasmid pMOD™<MCS> Transposon Construction Vector. The transposon is then removed from the pMOD backbone by digestion with PvuII and run on an agarose gel. The DNA is purified from the agarose using QIAquick Gel Extraction Kit (Qiagen Inc., Valencia, Calif.). 100 ng per microliter is generally obtained. Transposomes are made by mixing 500 ng of the purified transposon DNA with 5 ul of sterile water or (10 mm TRIS, pH8), 5 Units of EZ::TN™ Transposase (Eppicentre Technologies, Madison, Wis.) and 5 ul of 100% glycerol. The transposome reaction is mixed and incubated at room temperature for 30 minutes. 2 microliters of the transposome mixture is electroporated per aliquot of electrocompetent cells.

3. Eletrotransformation of S. aureus

Prior to electroporation, the competent cell aliquots are thawed on ice. Once completely, thawed, the cells are mixed with 2 ul of transposon and the volume is adjusted to 70 ul with cold 500 mM sucrose. The cell mixture is then aliquoted into a pre-chilled 0.1 cm gap electroporation cuvette. The mixture was then elecoporated as described by Laddaga et al. [1] using a Gene Pulserf and pulse controller (Bio-Rad Laboratories Inc., Hercules, Calif.) (2.5 KV, 25 MF capacitance, 100 ohm resistance, time constant 2.0-2.4). The cells are then immediately resuspended in 1.0 milliliter of B2 broth (10 mM $CaCl_2$ and 10 mM $MgCl_2$), incubated on ice for 5 minutes and transferred to a round bottom test tube and incubated with agitation at 37° C. for 1 to 2 hours, depending upon the transposon marker. To induce erythromycin expression of the transposon marker, half way through the 37° C. incubation, erythromycin is added at 10 ng/ml. The cells were then plated on NYE agar pH 7.0 [1] containing erythromycin (1 ug/ml) and lincomycin (5 ug/ml) and incubated at 37° C. for 48 hours.

4. DNA Extraction

Colonies are picked from the NYE antibiotic plates directly into a 96 deep well block containing 0.5 milliliters per well B2 broth (plus appropriate antibiotics). The blocks are allowed to incubate at 37° C. for 24 hours with agitation. After 24 hours, 0.1 milliliter is transferred to a 0.2 ml thin walled PCR plate using a multichannel pipette. Frozen stocks are also made from the deep well blocks and stored at –80° C. containing 10% (vol/vol) glycerol. The liquid in the PCR plates is pelleted by centrifugation at 2,000 rpm for 5 minutes. The supernatant is then removed and 150 microliters of a lysis cocktail is added to each well using a multichannel pipette and the plate is sealed with a sterile cap mat. The lysis cocktail consists of 1.0 mg/ml Lysoszyme (Sigma), 10 ug/ml Lysostaphin (Recombinant, AMBI Inc.) and Instagene Matrix (Bio-Rad). Once the lysis cocktail is added, the 96-well plates are incubated at 37 C for 30 minutes in a thermocycler with the lid heat turned off. During the incubation, the cocktail/cell mixture is mixed once by end over end shaking. Following the 37° C. incubation, the plates are centrifuged at 2,000 rpm briefly to remove any liquid that may be on the cap mat surface. The plates are then incubated at 98° C. in a thermocycler with the lid temperature on for 10 minutes. Following the 98° C. incubation, the plates are cooled to 4° C., mixed and then centrifuged at 3,000 rpm for 10-20 minutes. 5 ul of the resulting supernatant are used as template for PCR reactions.

5. DNA

The techniques used to characterize the DNA sequence of the transposon mutants consists of two PCR reactions were previously described by Kolter et al. [3]. For the first round of amplification, 5 ul of the InstaGene Lysis suspernatant is used as the template. In the first round of amplification, the primer unique to the transposon TNErm-1R (5'CTGTTTCAAAACAGTAGATG-3') (SEQ ID NO: 5) is used for the Erythromycin transposon and TNCm-1R2 (5'GATAGGCCTAAT-GACTGGC-3') (SEQ ID NO: 6) is used for the Chloramphenicol transposon with arbitrary primer arb-8 (5'-GGCCACGCGTCGACTAGTACNNNNGATAT-3') (SEQ ID NO: 7). This first amplification conditions are 1 minute at 94° C., followed by 6 cycles (30 seconds at 94° C., 30 seconds at 30° C., 2minutes at 72° C.) and 30 cycles (30 seconds at 94° C., 45 seconds at 45° C., 2 minute at 72° C.). The first PCR products are used for the second amplification. The primers used in the second are TNErm-2R (5'CAACATGACGAATC-CCTCCTTC-3') (SEQ ID NO: 8) or TNCm-2R2 (5'-GTCG-GTTTTCTAATGTCACTAACG-3') (SEQ ID NO: 9) for the erythromycin or chloramphenicol transposons respectively, plus an arbitrary primer arb-tail (5'-GGCCACGCGTCGAC-TAGTAC-3') (SEQ ID NO: 10). For the second, PCR, 5 ul from the first amplification round are used for template. The amplification conditions for the second PCR were 1 minute at 94° C. followed by 30 cycles (30 seconds of 94° C., 45 seconds at 50° C. and 1 minutes at 72° C.). The PCR product from the second amplification was purified prior to sequencing by treatment with S1 nuclease and Shrimp Alkaline Phosphatase SAP (Roche). For this, 100 ul sinculease/SAP was added to 10 ul PCR product. The S1/SAP mixture was incubated at 37° C. for 20 minutes followed by a 15 minute incubation at 80° C. 7 ul of the S1/SAP products were sequenced on an ABI 377 using the primer from the secondary PCR, TNErm-2R or TNCm -2R2.

REFERENCES RELATING TO FOREGOING PROTOCOLS

1) S. Schenk and Richard A. Laddaga
   Improved method for electroporation of Staphylococcus aureus.
   FEMS Microbiol Lett. 1992 Jul. 1; 73(1-2):133-8.
   PMID: 1521761 [PubMed—indexed for MEDLINE]
2) Ginger Rhoads Kraemer and John J. Iandolo
   High-Frequency Transformation of Staphylococcus aureus by Electroporation.
   Current Mibrobiol. 1990 Vol. 21 Pp. 373-376
3) Geore A. O'Toole and Roberto Kolter
   Initiation of biofilm formation in Pseudomonas fluorescens WCS365 proceeds via multiple, convergent signalling pathways: a genetic analysis.
   Mol Microbiol. 1998 May; 28(3): 449-61.
   PSMID: 9632250 [PubMed—indexed for MEDLINE])

Transposon insertions are generated using the above-described methods in S. aureus. The pMOD, pMOD (Erm-1) and pMOD (Can) plasmids referred to in the described methods are contained in FIGS. 3, 4 and 5 respectively. The sequences for these plasmids are contained in FIG. 6 (SEQ ID NO: 11), FIG. 7 (SEQ ID NO: 12) and FIG. 8 (SEQ ID NO: 13) respectively also available at the web address having the domain name epicentre.com and pathname sequences.asp Epicentre DNA sequences. Using these methods >7400 transposon mutants are generated.

High-Throughput Transposon Insertion Mapping (HTTIM)

Precise transposon insertion sites are determined by an anchored, semi-random PCR method for amplification of the transposase/genome junction region. (O'Toole and Kolter, 1998, Initiation of biofilm formation in Pseudomonas fluorescens WCS365 proceeds via multiple, convergent signaling pathways: a genetic analysis, Mol. Microbiol. 28(3): 449-61). The technique, HTTIM, uses both Tn5 specific and semi-random primers with conserved primer tails. A small aliquot of transposon mutant liquid culture is used as a template and amplification of a fragment containing an insertion site is achieved in a two-step process. The PCR product is then sequenced and the insertion site is entered into an Oracle database for analysis. To date, about 7,000 insertions have been mapped, each insertion representing the disruption of a gene or intergenic region that is not essential for survival on rich media.

Of these, ~7000 (6977) mutants are analyzed. Of these, about 6250 (6247, 89.5% total) have Tn5 sequences trimmed off. The mutants which map to a COL comprise about 5600 (5609, or about 80.3% of total). The mutants which correspond to a unique restriction site are about 5000 (4980, which corresponds to a sib rate of ~11.2% of total).

The mutants which map to an ORF are about 4650 (4651). Of these, 1404 ORF's are disrupted (51.2% of total). Of the mutants analyzed, 140 map to rDNA and 818 (14.6% of mapped mutants) are intergenic mutants.

Further, the analysis revealed a total of 2387600 bp of COL in ORF's or rDNA (15.0% intergenic regions).

With every insertion added to the map, the regions of the genome containing essential genes, and particularly those containing operons containing essential genes (because of potential polar effects of insertions in upstream genes), begin to become apparent because these regions will not be able to accommodate transposon insertions. Table 1 shows a listing of the open reading frames identified as existing between transposon insertions, with an assigned probability of essentiality according to the length of the putative open reading frames. These open reading frames cane be subjected to further analysis. For instance, the predicted ORFs can be examined individually for (1) identity with known genes of *S. aureus* with sequences deposited in GENBANK® (genetic sequence database), (2) similarity with well-characterized genes from other bacteria, or (3) presence of known functional motifs.

Statistical Analysis of Putative Essential and Important Genes

Probability correlates with length of the ORF, such that the longer the ORF, the higher the probability of hitting the ORF in a random transposon mutagenesis experiment, and the higher the confidence level that the ORF represents an essential or an important gene given that no transposon insertions therein were isolated. Statistical confidence levels in essentiality or importance can help narrow the focus in the screening of specific genes, thereby shortening the verification process and the subsequent identification of antibacterial agents specific for that gene or gene product. Thus, one of the benefits of the HTTIM approach is that it is a quantitative approach that lends itself well to statistical analysis.

The High-Throughput Transposon Insertion Mapping (HTTIM) strategy utilizes a transposon, which is a small, mobile DNA element that randomly inserts into the chromosome. Any transposon may be employed so long as its insertion into the chromosome is random, i.e., devoid of hot spots.

When the transposon insertion disrupts one of the essential genes in the *Staphylococcus* genome, the function of that gene is lost. If the disrupted gene is essential for growth, the transposon insertion mutant dies and cannot be characterized. If the transposon disrupts a gene that is non-essential, the mutant survives, grows and the transposon insertion site is mapped. By examining the insertion sites of a large number of transposon mutants, all, of the non-essential *S. aureus* genes can be identified, and by implication, all of the essential genes may be identified as well. Characterization of about 7000 transposon insertions revealed insertions in essential genes and resulted in an even distribution of insertions across the entire length of the genome. The remaining essential genes, in which a transposon insertion has never been observed, are candidates of essential genes (48.8%).

Because insertion of the transposon used here into the chromosome was proposed to be random, it was possible that some of the *Staphylococcus aureus* genes that did not receive a transposon insertion were simply not hit by random chance. One cannot truly know that a transposon has no hot spots and is entirely random until the data is analyzed, and the data here confirmed that the transposon derivative employed underwent random insertion in *S. aureus*. Thus, the chance that a gene will not be hit by the transposon as a matter of random chance increases as the length of the gene decreases, particularly for very small genes (<600 base pairs).

A Bayesian statistical model for truncated counting data is applied to the candidate essential gene set, and permits a determination that 37% percent of *S. aureus* genes are essential. Such a model may therefore be utilized to increase the statistical confidence that a given gene in the candidate subset is essential. An exemplary statistical model is provided in Example 1.

Physical Methods for Target Gene Validation

While the above methodology and the database of putative essential and important gene candidates established thereby is believed to be superior to existing methods with regard to the quantity of experimentation required to identify essential and important genes in *S. aureus* and the degree of confidence conferred, it should be understood that the methodology described herein can be incorporated into combined protocols with technology known in the art. For instance, the methods for verifying essentiality disclose in WO 01/07651, herein incorporated by reference in its entirety, would be useful as a secondary method to be utilized in combination with the methods described in this disclosure. Alternatively or additionally, one of several approaches may be used to determine whether a particular gene is essential (absolutely required for survival on rich medium) or important (the absence of which results in attenuated growth) to *S. aureus*.

Integration Knockouts

In one preferred embodiment of the invention, target validation is accomplished by use of integration knockouts. Methods of generating integration knockouts are known in the art. In one method, PCR is used to amplify a small (200-500 base pairs) portion of the coding sequence, or open reading frame (ORF) of the gene of interest. This fragment should be centrally located within the ORF. It should not include either termini of the gene's coding region. This fragment is then cloned into a plasmid vector that cannot replicate in *S. aureus*. The vector should have a drug resistance marker that is suitable for selection in *S. aureus*. Such a vector is then transformed into an electroporation competent strain of *S. aureus*, such as RN4220.

Following electroporation, the culture is plated on media which selects for *S. aureus* that contain the plasmid, and colonies that arise are the result of homologous recombination between the *S. aureus* and the cloned gene fragment on the plasmid. This is referred to as single-crossover recombination; a single recombination event takes place between the plasmid and the chromosome. This results in the integration of the entire plasmid into the *S. aureus* chromosome and the disruption of the gene from which the fragment is amplified (FIG. 1).

Variations of this approach are also possible. For instance, one could clone out the entire locus and isolate transposon insertion mutants in *E. coli*. Then, using general molecular biology techniques, i.e. by transposition from the *E. coli* genome, one can select plasmid insertions by transferring the vector into a recipient cell that does not contain the transposon or the antibiotic resistance marker encoded by the transposon. The plasmid would then be analyzed for insertions in the cloned gene. Thereafter, a similar assay could be performed by screening for double crossover events in *S. aureus* that result in recombination of the transposon into the chromosomal locus from the suicide vector.

Integration of the plasmid, or other insertion at the locus, can be confirmed by a relatively rapid PCR-based screen of the resulting recombinant clones. The advantage of this strategy, particularly the plasmid single crossover strategy, is that it requires only amplification of a short stretch of DNA followed by a single cloning step before recombination experiments can be performed. The disadvantage is that if the target gene is essential, no recombinants can be obtained. Failure to obtain recombinants as proof of essentiality is only suggestive evidence for essentiality. However, if a gene is in fact non-essential, this method will demonstrate that quickly.

Integration Knockouts with Extra-Chromosomal Complementation

In another embodiment of the invention, target validation is accomplished by use of integration knockouts with extra-chromosomal complementation. The method provides more convincing data when the target gene is essential. It employs the same type of non-replicating plasmid as described above, but recombinations are performed in strains already carrying a second copy of the target gene on an extra-chromosomal plasmid. This second copy can then supply the essential function when the chromosomal copy is disrupted. If disruptions can only be obtained when a complementing plasmid is present and not when a control plasmid is present, this is strong evidence that the target gene is essential. The advantage of this method is that you obtain colonies even when your gene of interest is essential. The disadvantage is that construction and sequencing of the complementing plasmid takes additional time.

Integration with a Regulatable Promoter (Promoter Swap)

Figure 2:
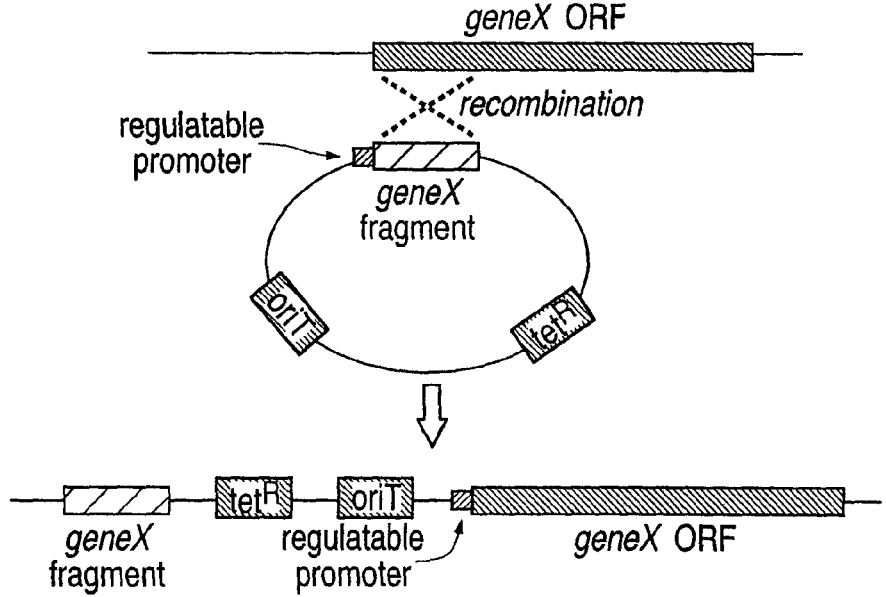
FIG. 2. Single crossover and integration of a plasmid resulting in the replacement of a wild type promoter with a regulatable promoter ("promoter swap" strategy).

In yet another embodiment of the invention, target validation is accomplished by use of integration with a regulatable promoter (a promoter swap). This approach also involves selecting for chromosomal integration of non-replicating plasmids via homologous recombination. However, the design of the integrating plasmid is different. In this case, the 5'300-500 base pairs of the coding sequence of the target gene is PCR amplified and cloned into a vector downstream of a regulated promoter, i.e. a let, xyl, or spac promoter, which is inducible in the presence of anhydrous tetracycline, xylose, or IPTG, respectively. The activity of the promoter can be modulated by the presence of a specific inducer molecule. The plasmid is electroporated into *S. aureus* and integration events selected for under conditions where the regulatable promoter is active. The resulting chromosomal integration replaces the target gene's natural promoter with the regulatable promoter from the plasmid (FIG. 2). If the target gene is essential, recombinants can only survive when the inducer molecule is present in their growth media to stimulate expression of the target gene. If the gene is non-essential, the recombinants' growth is independent of the addition of the inducer. The advantage of this strategy is that it requires only amplification of a short stretch of DNA followed by a single cloning step before recombination experiments can be performed.

REFERENCES

1. Lana Kim, Axel Mogk and Wolfgang Schumann. 1996. A Xylose-inducible *Bacillus subtilis* integration vector and its application. Gene 181: 71-76
2. Bateman, B. T., N. P. Donegan, T. M. Jarry, M. Palma, and A. L. Cheung. 2001. Evaluation of a Tetracycline-inducible promoter in *S. aureus* in vitro and in vivo and its application in demonstrating the role of sigB in microcolony formation. Infection and Immunity. 69 (12): 7851-7857.
3. Yansura, D., and D. J. Henner. 1984. Use of the *Escherichia coli* lac repressor and operator to control gene expression in *Bacillus subtilis*. Proc. Natl. Acad. Sci. USA 81: 439-443.

Accordingly, the invention includes a method for identifying an essential or important gene in a *Staphylococcus* genome comprising generating random transposon insertions in a Staphylococcal genome and screening the screening the mutants for essential and important genes.

Preferably, the method for generating random insertion into a Staphylococcal genome comprises subjecting Staphylococcal cells to random mutagenesis and culting the mutagenized cells in a recovery broth. Preferably, the recovery broth is B2 broth.

The method may further comprise validating the identification of an essential or important gene by use of one or more confirmation processes. Such confirmation processes include, but are not limited to confirmation by use of integration knockouts, confirmation by use of integration knockouts with extra-chromosomal complementation, confirmation by use of integration with a regulatable promoter (promoter swap).

LIST OF EMBODIMENTS

1. An isolated nucleic acid molecule comprising a nucleic acid sequence encoding a polypeptide having at least 80% sequence identity to a polypeptide encoded by a nucleic acid sequence selected from the group consisting of the *Staphylococcus aureus* open reading frames (ORFs) listed in Table 1.
2. An isolated nucleic acid molecule comprising a nucleic acid sequence encoding a polypeptide having at least 80% sequence identity to a polypeptide encoded by an essential or important nucleic acid sequence selected from the group consisting of the *Staphylococcus aureus* open reading frames (ORFs) listed in Table 1, wherein said essential or important nucleic acid sequence is identified as being essential or important by integration knock-out coupled with extra-chromosomal complementation.
3. An isolated nucleic acid molecule comprising a nucleic acid sequence encoding a polypeptide having at least 80% sequence identity to a polypeptide encoded by an essential or important nucleic acid sequence selected from the group consisting of the *Staphylococcus aureus* open reading frames (ORFs) listed in Table 1, wherein said essential or important nucleic acid sequence is identified as being essential by integration of a regulatable promoter into the gene.
4. A method of screening for an antibacterial agent, comprising determining whether a test compound is active against the bacterial gene of embodiment 1.
5. A method of screening for an antibacterial agent, comprising determining whether a test compound is active against the protein encoded by the bacterial gene of embodiment 1.
6. A method of screening for an antibacterial agent, comprising determining whether a test compound is active against the essential or important bacterial gene of embodiment 2.
7. A method of screening for an antibacterial agent, comprising determining whether a test compound is active against the protein encoded by the essential or important bacterial gene of embodiment 2.
8. A method of screening for an antibacterial agent, comprising determining whether a test compound is active against the essential or important bacterial gene of embodiment 3.

9. A method of screening for an antibacterial agent, comprising determining whether a test compound is active against the protein encoded by the essential or important bacterial gene of embodiment 3.

10. The method of embodiment 5, comprising the steps of:
a) contacting said protein or a biologically active fragment thereof with a test compound; and
b) determining whether said test compound binds to said protein or said fragment; wherein binding of said test compound to said polypeptide or said fragment is indicative that said test compound is an antibacterial agent.

11. The method of embodiment 7, comprising the steps of:
a) contacting said protein or a biologically active fragment thereof with a test compound; and
b) determining whether said test compound binds to said protein or said fragment; wherein binding of said test compound to said polypeptide or said fragment is indicative that said test compound is an antibacterial agent.

12. The method of embodiment 9, comprising the steps of:
a) contacting said protein or a biologically active fragment thereof with a test compound; and
b) determining whether said test compound binds to said protein or said fragment; wherein binding of said test compound to said polypeptide or said fragment is indicative that said test compound is an antibacterial agent.

13. A method for evaluating a test agent for inhibition of expression of the gene of embodiment 1, comprising:
a) contacting a cell expressing said gene with said agent; and
b) determining the amount or level of expression of said essential gene in said sample.

14. A method for evaluating a test agent for inhibition of expression of the essential or important gene of embodiment 2, comprising:
a) contacting a cell expressing said essential or important gene with said agent; and
b) determining the amount or level of expression of said essential or important gene in said sample.

15. A method for evaluating a test agent for inhibition of expression of the essential or important gene of embodiment 3, comprising:
a) contacting a cell expressing said essential or important gene with said agent; and
b) determining the amount or level of expression of said essential or important gene in said sample.

16. The method of embodiment 13, wherein said level of expression is measured by measuring the amount of expression product in said cell relative to a cell that has not been contacted with said agent.

17. The method of embodiment 13, wherein said level of expression is measured by measuring the level of expression of a gene fusion to said gene relative to a cell containing said gene fusion that has not been contacted with said agent.

18. The method of embodiment 13, wherein said level of expression is measured by measuring the level of expression of a protein fusion to said gene relative to a cell containing said protein fusion that has not been contacted with said agent.

19. A method for evaluating an potential antibacterial agent, comprising the steps of:
a) providing a bacterial strain comprising a mutant form of the gene of embodiment 1, wherein said mutant form of the gene confers a growth conditional or attenuated growth phenotype;
b) contacting bacteria of said bacterial strain with said test compound in semi-permissive or permissive growth conditions; and
c) determining whether the growth of said bacterial strain comprising said mutant form of a gene is reduced in the presence of said test compound to a greater extent than a comparison bacteria comprising a normal form of said gene.

20. A library of nucleic acid sequences consisting essentially of nucleic acid sequences having at least about 80% protein sequence identity to a nucleic acid sequence selected from the group consisting of the *Staphylococcus aureus* open reading frames (ORFs) listed in Table 1, wherein said library of nucleic acid sequences is employed to identify essential genes in *Staphylococcus*.

21. A map of at least about 500-1500 transposon insertions in the genome of *Staphylococcus aureus*, wherein said map is useful for identifying genes that are essential for survival of said *Staphylococcus aureus*.

22. A vector comprising a promoter operably linked to the nucleic acid sequence of embodiment 1.

23. The vector of embodiment 22, wherein said promoter is active in *Staphylococcus aureus, Escherichia coli, Pseudomonas aeruginosa, Hemophilus influenzae, Neisseria gonorrhea, Klebsiella pneumoniae*, and *Streptocooci*.

24. A host cell comprising the vector of embodiment 22.

25. A fragment of the nucleic acid of embodiment 1, said fragment comprising at least 10, at least 20, at least 25, at least 30, or at least 50 consecutive bases of said nucleic acid.

26. A protein having at least about 80% sequence identity to the protein encoded by the nucleic acid of embodiment 1.

27. A protein having at least about 80% sequence identity to the protein encoded by the nucleic acid of embodiment 2.

28. A protein having at least about 80% sequence identity to the protein encoded by the nucleic acid of embodiment 3.

29. An antibody or antibody fragment capable of specifically binding the protein of embodiment 26.

30. An antibody or antibody fragment capable of specifically binding the protein of embodiment 27.

31. An antibody or antibody fragment capable of specifically binding the protein of embodiment 28.

32. An agent identified as having anti-bacterial activity by any of the methods of embodiments 4-19.

33. A method for inhibiting the growth or survival of *Staphylococcus aureus* comprising contacting said bacteria with the agent of embodiment 32 so as to inhibit growth or survival.

34. A pharmaceutical composition comprising the agent of embodiment 32.

35. A method for treating a patient having a *Staphylococcus aureus* infection, comprising administering to said patient an amount of the agent of embodiment 32 effective to reduce or inhibit growth or survival of said *Staphylococcus aureus*.

36. A method of protecting a patient against a *Staphylococcus aureus* infection, comprising administering to said patient an amount of the agent of embodiment 32 effective to prevent said patient from acquiring a *Staphylococcus aureus* infection.

37. The isolated nucleic acid molecule of embodiment 2, wherein said nucleic acid contains an essential gene.

38. The nucleic acid library of embodiment 20, wherein said map is in electronic form.

39. The library of embodiment 39, wherein said electronic form is selected from the group consisting of magnetic storage media, such as a floppy disc, a hard disc storage medium, and a magnetic tape; optical storage media such as CD-ROM; electrical storage media such as RAM and ROM; hybrids of these categories such as magnetic/optical storage media; computer readable forms such as a word processing text file, database format, searchable files, executable files and search program software.

40. The transposon insertion map of embodiment 21, wherein said map is in electronic form.

41. The map of embodiment 38, wherein said electronic form is selected from the group consisting of magnetic storage media, such as a floppy disc, a hard disc storage medium, and a magnetic tape; optical storage media such as CD-ROM; electrical storage media such as RAM and ROM; hybrids of these categories such as magnetic/optical storage media; computer readable forms such as a word processing text file, database format, searchable files, executable files and search program software.

42. A method for identifying a library of putative essential or important genes using a High Throughput Transposon Insertion Database (HTTIM), comprising:
    (a) mutagenizing a *Staphylococcus* genome with a transposon such that individual cells containing at least one transposon insertion are isolated;
    (b) collecting and mapping said at least one transposon insertion in each individual cell so as to form a database of transposon insertion sites, or an HTTIM;
    (c) comparing said database of transposon insertion sites with a database comprising the genomic sequence of the bacterium to identify open reading frames in said genomic sequence database that are not disrupted by a transposon insertion;
    (d) forming a library from said putative essential or important genes that are not disrupted by a transposon.

43. The method of embodiment 42, wherein said bacteria is *S. aureus*.

44. The method of embodiment 42, wherein said transposon inserts randomly into the target genome.

45. The method of embodiment 42, wherein said transposon is 3,000 to 6,000.

46. The method of embodiment 42, wherein said HTTIM comprises at least about 4,000 to 5,000 transposon insertion sites.

47. The library of putative essential or important genes identified by the method of embodiment 42, wherein said library comprises at most about 500 to 1850 genes.

48. The library of putative essential or important genes identified by the method of embodiment 42, wherein said library comprises at most about 1000 to 1400 genes.

49. The library of putative essential or important genes identified by the method of embodiments 42, wherein said library comprises at most about 600-625 genes.

50. The library of putative essential or important genes identified by the method of embodiments 42, wherein said library comprises at most about 530-543 genes.

51. The method of embodiment 42, further comprising a statistical calculation for identifying putative essential or important genes.

52. The method of embodiment 51, further comprising the statistical method applied herein.

53. The method of embodiment 42, further comprising a physical mutagenesis experiment in order to verify essential or important genes.

54. The method of embodiment 53, wherein said physical mutagenesis comprises knocking out a putative essential or important gene or creating a promoter swap mutant.

55. An essential or important gene identified by the method of embodiment 53.

56. An antibacterial agent that targets the gene of embodiment 55, or the gene product encoded by said gene.

57. A pharmaceutical composition comprising said antibacterial agent of embodiment 56.

EXAMPLES

Essential Genes Identified

Example 1

A Bayesian Statistical Model for Increasing Statistical Confidence of Essentiality A Bayesian statistical model for truncated counting data was applied to the candidate essential gene set, and permitted a determination that about 37% percent of *S. aureus* genes are essential. This model may therefore be utilized to increase the statistical confidence that a given gene in the candidate subset is essential, by the following rationale. For a given set of genes, the percentage of nonessential genes is independent of gene size. For a fixed gene size $\delta$, the observations $X_1, X_2, \ldots, X_N$ are Poisson($\lambda \cdot \delta$), of which all observations of value zero are missing. Let $\{x_1^*, x_2^*, \ldots, x_n^*\} \subseteq \{x_1^*, x_2^*, \ldots, x_N^*\}$ be the subset of all nonzero observations. Then the subset $\{x_1^*, x_2^*, \ldots, x_n^*\}$ composes a random sample of size n from a truncated Poisson distribution and the likelihood function of the joint distribution of $\{n, x_1^*, x_2^*, \ldots, x_n^*\}$, conditional on the total number of nonessential genes, N, can be obtained as follows $$L(\lambda \mid N) = \binom{N}{n} \cdot q^n \cdot p^{N-n} (\lambda \cdot \delta)^S \cdot \left(\frac{p}{q}\right)^n \left(\prod_{i=1}^{n} x_i^*!\right)^{-1} \propto \binom{N}{n} \cdot \lambda^S \cdot e^{-\lambda \cdot \delta \cdot N},$$

where $s = x_1^* + x_2^* + \ldots + x_n^*$ and N is the number of nonessential genes of size $\delta$.

The Bayesian model consists of the conditional model and a prior distribution on the parameter N. Assume N, the number of nonessential genes, is distributed as binomial $B(M, \gamma)$ with M being the total number of genes of size $\delta$, and $\gamma$ is the proportion of nonessential genes which is an unknown constant and is independent of gene size. The likelihood function of the joint distribution of $\{N, n, \gamma, X_1^*, X_2^*, \ldots, X_n^*\}$ can be written as $$L(\gamma, \lambda, N \mid n, S) \propto \binom{M}{N} \cdot \binom{N}{n} \cdot \gamma^N (1-\gamma)^{M-N} \cdot \lambda^S \cdot e^{-\lambda \cdot \delta \cdot N}$$

Let $\bar{\delta} = (\delta_1, \delta_2, \ldots \delta_g)^T$ be a vector of g different gene sizes and $\bar{M} = (M_1, M_2, \ldots, M_g)^T$ be the vector of known numbers of total genes, $\bar{N} = (N_1, N_2, \ldots, N_g)^T$ be the unknown numbers of nonessential genes, $\bar{n} = (n_1, n_2, \ldots, n_g)^T$ be the vector of nonzero observations from the nonessential genes, and $\bar{S} = (S_1, S_2, \ldots, S_g)^T$ be the sums of nonzero observations. The likelihood function of the joint distribution of $\{\bar{N}, \bar{n}, \gamma, \bar{S}\}$ can be written as $$L(\gamma, \lambda, \bar{N}) \propto \gamma^{\|\bar{N}\|_1} (1-\gamma)^{\|\bar{M}\|_1 - \|\bar{N}\|_1} \cdot \lambda^{\|\bar{S}\|_1} \cdot e^{-\lambda \cdot (\bar{\delta}^1 \cdot \bar{N})} \prod_{i=1}^{g} \binom{M_i}{N_i}\binom{N_i}{n_i}.$$

Where $\|*\|_1$ is the $L_1$ norm of a vector, and $$\left(\bar{\delta}^T \cdot \bar{N}\right) = \sum_{i=1}^{g} \delta_i \cdot N_i.$$

Up to an additive constant, the log-likelihood function of the joint distribution of $\{\bar{N}, \bar{n}, \gamma, \bar{S}\}$ can be written as $$\mathcal{J}(\gamma, \lambda, \bar{N}) = \|\bar{N}\|_1 \cdot \ln(\gamma) + (\|\bar{M}\|_1 - \|\bar{N}\|_1) \cdot \ln(1-\gamma) + \|\bar{S}\|_1 \cdot \ln(\lambda) - \lambda \cdot \left(\bar{\delta}^T \cdot \bar{N}\right) - \sum_{i=1}^{g} \ln((M_i - N_i)!) - \sum_{i=1}^{g} \ln((N_i - n_i)!).$$

and the maximum likelihood (ML) estimators of the parameters $\gamma$ and $\lambda$ are $$\hat{\gamma} = \|\bar{N}\|_1 / \|\bar{M}\|_1 \text{ and } \hat{\lambda} = \|\bar{S}\|_1 / (\bar{\delta}^T \cdot \bar{N})$$

However, when g is large, say, in the order of hundreds, as in the present disclosure, obtaining the ML estimator of the parameter vector $\bar{N} = (N_1, N_2, \ldots, N_g)^T$ in a high dimensional parameter space is a challenging problem. A searching algorithm was developed to find the maximum likelihood estimator as $\bar{N} = \bar{n} \oplus K^*$. Where $\oplus$, an operator between the observed vector $\bar{n}$ and any integer $0 \leq k \leq \|\bar{M}\|_1 - \|\bar{n}\|_1$ defined as follows:

$$\bar{n} \oplus 0 = \bar{n},$$

$$\bar{n} \oplus 1 = \{\bar{n} + \bar{1}_j : \Delta_j \mathfrak{J}^*(\bar{n}) > \Delta_i \mathfrak{J}^*(\bar{n}) \text{ for all } i \neq j\},$$

$$\bar{n} \oplus k = (\bar{n} \oplus (k-1)) \oplus 1 \text{ for } k \geq 2.$$

and $K^* = \max\{k^* \geq 0 : G(k) \geq 0 \text{ for all } 0 \leq k \leq k^*\}$.

As a result of this modeling, we were able to estimate that 16 to 17 percent of the genes are essential.

Alternatively, a stepwise maximum likelihood (ML) gain method may be used to find the estimator as follows. For any $\bar{N} = (N_1, N_2, \ldots, N_g)^T$, it is easy to verify using (2.7) that the ML estimators of the parameters $\gamma$ and $\lambda$ are $$\hat{\gamma} = \|\bar{N}\|_1 / \|\bar{M}\|_1 \quad (3.1)$$

and $$\hat{\lambda} = \|\bar{S}\|_1 / (\bar{\delta}^T \cdot \bar{N}) \quad (3.2)$$

respectively. Substituting (3.1) and (3.2) for $\gamma$ and $\lambda$, respectively, in (2.6), we have $$\mathcal{J}^*(\bar{N}) \propto \|\bar{N}\|_1 \cdot \ln(\|\bar{N}\|_1) + (\|\bar{M}\|_1 - \|\bar{N}\|_1) \cdot \ln(\|\bar{M}\|_1 - \|\bar{N}\|_1) - \|\bar{S}\|_1 \cdot \ln(\bar{\delta}^T \cdot \bar{N}) - \sum_{i=1}^{g} (\ln((M_i - N_i)!) + \ln((N_i - n_i)!)). \quad (3.3)$$

Define $$\Delta_i \mathfrak{J}^*(\bar{N}) = \mathfrak{J}^*(\bar{N} + \bar{1}_i) - \mathfrak{J}^*(\bar{N}) \quad (3.4)$$

for any $i \in \{1, 2, \ldots, g\}$ and $\bar{N} \in \{n_i < N_i < M_i, n_j \leq N_j \leq M_j : j \neq i\}$. Where $\bar{1}_i = (0, \ldots, 0, 1, 0, \ldots 0)^T$ with 1 at the $i^{th}$ position. For notational purpose, let $$\eta(k) = k \cdot \ln(k) + (\|\bar{M}\|_1 - k) \cdot \ln(\|\bar{M}\|_1 - k) \quad (3.5)$$

for $\|\bar{n}\|_1 \leq k < \|\bar{M}\|_1$, Then, (3.4) can be written as $$\Delta_i \mathcal{J}^*(\bar{N}) = \quad (3.6)$$
$$\eta(\|\bar{N}\|_1 + 1) - \eta(\|\bar{N}\|_1) - \|\bar{S}\|_1 \cdot \ln\left(1 + \delta_i / \left(\bar{\delta}^T \cdot \bar{N}\right)\right) + \ln\left(\frac{M_i - N_i}{N_i - n_i + 1}\right)$$

To obtain ML estimator of $\bar{N}$, we define an operator, denoted as $\oplus$, between the observed vector n and any integer $0 \leq k \leq \|\bar{M}\|_1 - \|\bar{n}\|_1$ as follows:

$$\bar{n} \oplus 0 = \bar{n},$$

$$\bar{n} \oplus 1 = \{\bar{n} + \bar{1}_j : \Delta_j \mathfrak{J}^*(\bar{n}) > \Delta_i \mathfrak{J}^*(\bar{n}) \text{ for all } i \neq j\}, \text{ and}$$

$$\bar{n} \oplus k = (\bar{n} \oplus (k-1)) \oplus 1 \text{ for } k \geq 2. \quad (3.7)$$

We also define a likelihood-gain function G as $$G(0) = 0$$

$$G(k) = \mathfrak{J}^*(\bar{n} \oplus k) - \mathfrak{J}^*(\bar{n} \oplus (k-1)), \text{ for } 1 \leq k \leq \|\bar{M}\|_1 - \|\bar{n}\|_1 \quad (3.8)$$

THEOREM 1: if $$\sum_{i=1}^{g} \left(n_i - \exp\left(\frac{\delta_i \|\bar{S}\|_1}{\bar{\delta}^T \cdot \bar{n}}\right)\right) > 0 \quad (3.9)$$

then $G(1) > 0$.

Proof: If $G(1) \leq 0$, then by (3.5), $$\Delta_i \mathcal{J}^*(\bar{n}) \leq 0 \text{ for all } 1 \leq i \leq g \Rightarrow$$
$$\eta(\|\bar{n}\|_1 + 1) - \eta(\|\bar{n}\|_1) - \|\bar{S}\|_1 \cdot \ln\left(1 + \delta_i / \left(\bar{\delta}^T \cdot \bar{n}\right)\right) + \ln(M_i - n_i) \leq 0 \Rightarrow$$
$$\|\bar{S}\|_1 \cdot \ln\left(1 + \delta_i / \left(\bar{\delta}^T \cdot \bar{n}\right)\right) - \ln(M_i - n_i) \geq \eta(\|\bar{n}\|_1 + 1) - \eta(\|\bar{n}\|_1) \Rightarrow$$
$$\frac{\left(1 + \delta_i / \bar{\delta}^T \bar{n}\right)^{\|\bar{S}\|_1}}{(M_i - n_i)} \geq \frac{(\|\bar{n}\|_1 + 1)^{\|\bar{n}\|_1 + 1} \cdot (\|\bar{M}\|_1 - \|\bar{n}\|_1 - 1)^{\|\bar{M}\|_1 - \|\bar{n}\|_1 - 1}}{(\|\bar{n}\|_1)^{\|\bar{n}\|_1} \cdot (\|\bar{M}\|_1 - \|\bar{n}\|_1)^{\|\bar{M}\|_1 - \|\bar{n}\|_1}}$$

Add the 2 sites up over i, we have $$\sum_{i=1}^{g} \left(1 + \delta_i / \bar{\delta}^T \bar{n}\right)^{\|\bar{S}\|_1} \geq$$
$$\|\bar{n}\|_1 \cdot \left(1 + \frac{1}{\|\bar{n}\|_1}\right)^{\|\bar{n}\|_1 + 1} \cdot \left(1 - \frac{1}{\|\bar{M}\|_1 - \|\bar{n}\|_1}\right)^{\|\bar{M}\|_1 - \|\bar{n}\|_1 - 1}$$

Using the factors that, for any $x > 0$, $(1+1/x)^x < e$, $(1+1/x)^{x+1} > e$, and $(1-1/x)^{x-1} > e^{-1}$, we obtain $$\sum_{i=1}^{g} \exp\left(\frac{\delta_i \cdot \|\bar{S}\|_1}{\bar{\delta}^T \bar{n}}\right) \geq \|\bar{n}\|_1 \cdot e \cdot e^{-1} = \|\bar{n}\|_1 \Rightarrow \sum_{i=1}^{g} \left(n_i - \exp\left(\frac{\delta_i \cdot \|\bar{S}\|_1}{\bar{\delta}^T \cdot \bar{n}}\right)\right) \leq 0$$

which is contradiction to the condition (3.9).

When $g=1$, the condition (3.9) becomes $\ln(n) > (X_1 + \ldots + X_n)/n$. Hence, this theorem says, on average, when the mean count is less than the natural logarithms of the number of nonzero observations, the vector $\bar{n}$ can not be the ML estimator of $\bar{N}$. In another word, when the mean count is not too large, there must have some missing observations from non-essential genes.

THEOREM 2:

$$\Delta_i \Im^*(\overline{N}) > \Delta_i \Im^*(\overline{N} - \overline{1}_j) \text{ for all } i \neq j \quad (3.10)$$

Proof: By definition in (3.5), $$\frac{d[\eta(x+1) - \eta(x)]}{dx} = \ln\left(\frac{x+1}{x} \cdot \frac{\|\overline{M}\|_1 - x}{\|\overline{M}\|_1 - x - 1}\right) > 0$$

for any $0 < x < \|\overline{M}\|_1$. Hence $\eta(\|\overline{N}\|_1 + 1) - \eta(\|\overline{N}\|_1))$ is an increase function of $\|\overline{N}\|_1$. Using this result, we have $$\Delta_i \Im^*(\overline{N}) - \Delta_i \Im^*(\overline{N} - \overline{1}_j) =$$
$$(\eta(\|\overline{N}\|_1 + 1) - \eta(\|\overline{N}\|_1)) - (\eta(\|\overline{N}\|_1) - \eta(\|\overline{N}\|_1 - 1)) -$$
$$\|\overline{S}\|_1 \cdot \ln(1 + \delta_i / (\overline{\delta}^T \cdot \overline{N})) + \|\overline{S}\|_1 \cdot \ln(1 + \delta_i / (\overline{\delta}^T \cdot \overline{N} - \delta_j)) >$$
$$\|\overline{S}\|_1 \cdot [\ln(1 + \delta_i / (\overline{\delta}^T \cdot \overline{N} - \delta_j)) - \ln(1 + \delta_i / (\overline{\delta}^T \cdot \overline{N}))] > 0.$$

Define $$K^* = \max\{k^* \geq 0 : G(k) \geq 0 \text{ for all } 0 \leq k \leq k^*\}. \quad (3.11)$$

THEOREM 3: Under (3.9), for any $1 \leq j \leq g$ and $1 \leq k \leq K^*$, if $\overline{N} = \overline{n} \oplus k - \overline{1}_j \in \{n_j \leq N_j \leq M_j\}$, then $$\Im^*(\overline{n} \oplus k) > \Im^*(\overline{n} \oplus k - \overline{1}_j) \quad (3.12)$$

Proof: This is obviously true when k=1. Assume (3.12) is right for integers $1, 2, \ldots, k$. For integer k+1, we have $$\Im^*(\overline{n} \oplus (k+1) - \overline{1}_j) -$$
$$\Im^*(\overline{n} \oplus k) = [\Im^*(\overline{n} \oplus (k+1) - \overline{1}_j) - \Im^*(\overline{n} \oplus k - \overline{1}_j)] + [$$
$$\Im^*(\overline{n} \oplus k - \overline{1}_j) - \Im^*(\overline{n} \oplus k)] < [\Im^*(\overline{n} \oplus (k+1) - \overline{1}_j) - \Im^*(\overline{n} \oplus k - \overline{1}_j)]$$

By Theorem 2, $$\Im^*(\overline{n} \oplus (k+1) - \overline{1}_j) - \Im^*(\overline{n} \oplus k - \overline{1}_j) < \Im^*(\overline{n} \oplus (k+1)) - \Im^*(\overline{n} \oplus k)$$

Therefore $$\Im^*(\overline{n} \oplus (k+1)) < \Im^*(\overline{n} \oplus (k+1) - \overline{1}_j)$$

Combine Theorems 1-3, we obtain ML estimator of $\overline{N}$ as:

$$\overline{N} = \overline{n} \oplus K^* \quad (3.13)$$

Example 2

TABLE I

| SANUMBER | GENE_NAME | SIZE | PROBABILITY | LOWER | UPPER |
|---|---|---|---|---|---|
| SA0001 | dnaA | 1358 | 0.984672 | 0.9807534 | 0.9877383 |
| SA0002 | dnaN | 1130 | 0.9690877 | 0.9626406 | 0.9743274 |
| SA0003 |  | 242 | 0.5250502 | 0.5053862 | 0.5435709 |
| SA0005 | gyrB | 1931 | 0.9973706 | 0.9963655 | 0.9980856 |
| SA0016 | dnaB | 1397 | 0.9864051 | 0.9828177 | 0.9891943 |
| SA0017 |  | 89 | 0.2395316 | 0.2281006 | 0.250575 |
| SA0019 | yycF | 698 | 0.8832234 | 0.8687278 | 0.8958807 |
| SA0026 |  | 1253 | 0.978827 | 0.973878 | 0.9827678 |
| SA0027 |  | 236 | 0.5162013 | 0.4966774 | 0.5346084 |
| SA0028 |  | 671 | 0.8731086 | 0.8580015 | 0.886359 |
| SA0029 |  | 164 | 0.3962339 | 0.3794046 | 0.4122914 |
| SA0030 |  | 227 | 0.5026178 | 0.4833259 | 0.5208334 |
| SA0031 |  | 740 | 0.8973789 | 0.8838253 | 0.9091313 |
| SA0032 | maoC | 425 | 0.7295237 | 0.7095503 | 0.7477728 |
| SA0033 | pbp2 | 2003 | 0.997893 | 0.9970523 | 0.9984841 |
| SA0034 | mecR | 983 | 0.9514098 | 0.9427053 | 0.9586591 |
| SA0035 |  | 257 | 0.5464708 | 0.5265046 | 0.5652295 |
| SA0036 |  | 1520 | 0.9906883 | 0.987986 | 0.9927469 |
| SA0037 |  | 503 | 0.787231 | 0.7685119 | 0.8041141 |
| SA0038 |  | 308 | 0.6123313 | 0.5917894 | 0.6314681 |
| SA0039 |  | 89 | 0.2395316 | 0.2281006 | 0.250575 |
| SA0040 |  | 347 | 0.6561649 | 0.6355708 | 0.6752264 |
| SA0041 | ccrB | 1621 | 0.9931754 | 0.9910445 | 0.9947717 |
| SA0042 | ccrA1 | 1346 | 0.9840955 | 0.9800697 | 0.9872521 |
| SA0043 |  | 1766 | 0.9956315 | 0.9941264 | 0.9967321 |
| SA0044 |  | 293 | 0.5940213 | 0.5735828 | 0.6131093 |
| SA0045 |  | 1574 | 0.9921137 | 0.9897324 | 0.9939114 |
| SA0046 |  | 1325 | 0.983034 | 0.9788142 | 0.9863542 |
| SA0047 |  | 1064 | 0.9621279 | 0.954733 | 0.9682043 |
| SA0048 |  | 257 | 0.5464708 | 0.5265046 | 0.5652295 |
| SA0049 |  | 728 | 0.8935193 | 0.8796982 | 0.9055276 |
| SA0051 |  | 1613 | 0.9930054 | 0.9908337 | 0.9946343 |
| SA0052 |  | 1508 | 0.9903381 | 0.9875592 | 0.9924592 |
| SA0053 |  | 1034 | 0.958466 | 0.950605 | 0.9649575 |
| SA0054 |  | 1049 | 0.9603392 | 0.952714 | 0.9666204 |
| SA0055 |  | 119 | 0.3065803 | 0.2926085 | 0.3200112 |
| SA0056 |  | 125 | 0.3192633 | 0.3048482 | 0.3331066 |
| SA0057 |  | 89 | 0.2395316 | 0.2281006 | 0.250575 |
| SA0059 |  | 449 | 0.7487759 | 0.7291367 | 0.7666484 |
| SA0060 |  | 98 | 0.2602999 | 0.2480474 | 0.2721192 |
| SA0066 |  | 98 | 0.2602999 | 0.2480474 | 0.2721192 |
| SA0069 |  | 293 | 0.5940213 | 0.5735828 | 0.6131093 |
| SA0077 |  | 479 | 0.7709258 | 0.7517728 | 0.7882691 |
| SA0081 |  | 161 | 0.3906354 | 0.373965 | 0.4065492 |
| SA0087 |  | 104 | 0.2738294 | 0.2610581 | 0.2861368 |
| SA0109 |  | 404 | 0.7114715 | 0.6912539 | 0.7300083 |

TABLE I-continued

| SANUMBER | GENE_NAME | SIZE | PROBABILITY | LOWER | UPPER |
|---|---|---|---|---|---|
| SA0110 | | 623 | 0.852915 | 0.836723 | 0.8672308 |
| SA0131 | | 200 | 0.4595361 | 0.4411085 | 0.4770137 |
| SA0133 | | 101 | 0.2670958 | 0.2545811 | 0.2791621 |
| SA0134 | | 481 | 0.772331 | 0.7532128 | 0.7896371 |
| SA0137 | cap5B | 683 | 0.8777079 | 0.8628729 | 0.8906939 |
| SA0146 | cap5K | 1202 | 0.9752299 | 0.9697003 | 0.9796705 |
| SA0147 | cap5L | 1202 | 0.9752299 | 0.9697003 | 0.9796705 |
| SA0149 | cap5N | 884 | 0.9341086 | 0.9235835 | 0.9430194 |
| SA0150 | cap5O | 1259 | 0.9792142 | 0.97433 | 0.9830996 |
| SA0152 | | 323 | 0.6298155 | 0.6092186 | 0.6489558 |
| SA0166 | | 491 | 0.7792289 | 0.7602885 | 0.7963456 |
| SA0172 | entB | 494 | 0.7812572 | 0.7623713 | 0.7983162 |
| SA0188 | ggt | 2003 | 0.997893 | 0.9970523 | 0.9984841 |
| SA0189 | | 770 | 0.9064267 | 0.893534 | 0.9175506 |
| SA0206 | | 191 | 0.4443617 | 0.426283 | 0.461534 |
| SA0208 | | 341 | 0.6497588 | 0.6291542 | 0.6688491 |
| SA0214 | | 1502 | 0.9901581 | 0.9873401 | 0.9923111 |
| SA0219 | | 170 | 0.4072771 | 0.3901425 | 0.4236096 |
| SA0223 | | 122 | 0.312951 | 0.298755 | 0.3265907 |
| SA0226 | | 95 | 0.2534409 | 0.2414564 | 0.2650075 |
| SA0229 | | 464 | 0.7601063 | 0.7407017 | 0.7777215 |
| SA0230 | | 275 | 0.5709042 | 0.5506598 | 0.5898675 |
| SA0231 | | 131 | 0.3317143 | 0.3168761 | 0.3459497 |
| SA0234 | | 143 | 0.3559372 | 0.3403112 | 0.3708987 |
| SA0239 | tagF | 1166 | 0.9723287 | 0.9663551 | 0.9771546 |
| SA0240 | | 713 | 0.8884901 | 0.8743327 | 0.9008214 |
| SA0241 | | 1022 | 0.9569039 | 0.9488503 | 0.9635678 |
| SA0246 | lytR | 737 | 0.8964273 | 0.882807 | 0.9082435 |
| SA0250 | | 788 | 0.9114679 | 0.8989654 | 0.9222229 |
| SA0252 | | 758 | 0.9029075 | 0.8897519 | 0.9142808 |
| SA0253 | rbsK | 911 | 0.939361 | 0.9293558 | 0.9477936 |
| SA0256 | | 107 | 0.280501 | 0.2674788 | 0.2930441 |
| SA0258 | | 176 | 0.4181183 | 0.4006946 | 0.4347098 |
| SA0260 | | 401 | 0.7087961 | 0.6885477 | 0.7273704 |
| SA0262 | | 989 | 0.9522986 | 0.9436966 | 0.9594553 |
| SA0264 | | 656 | 0.8671154 | 0.8516683 | 0.8806979 |
| SA0268 | | 650 | 0.8646395 | 0.8490565 | 0.8783552 |
| SA0273 | | 455 | 0.7533709 | 0.7338233 | 0.7711423 |
| SA0274 | | 239 | 0.5206462 | 0.5010508 | 0.5391114 |
| SA0275 | | 1331 | 0.9833443 | 0.9791808 | 0.986617 |
| SA0277 | | 389 | 0.697844 | 0.6774835 | 0.7165584 |
| SA0279 | | 671 | 0.8731086 | 0.8580015 | 0.886359 |
| SA0280 | | 314 | 0.619422 | 0.5988525 | 0.6385653 |
| SA0282 | | 428 | 0.7320087 | 0.7120741 | 0.7502133 |
| SA0283 | | 680 | 0.876574 | 0.8616709 | 0.8896259 |
| SA0285 | | 215 | 0.4839115 | 0.4649714 | 0.5018306 |
| SA0287 | | 437 | 0.7393275 | 0.7195144 | 0.7573941 |
| SA0288 | | 149 | 0.3677175 | 0.3517255 | 0.383014 |
| SA0289 | | 488 | 0.7771817 | 0.7581873 | 0.7943558 |
| SA0290 | | 680 | 0.876574 | 0.8616709 | 0.8896259 |
| SA0291 | | 497 | 0.7832669 | 0.7644361 | 0.8002676 |
| SA0292 | | 497 | 0.7832669 | 0.7644361 | 0.8002676 |
| SA0296 | | 497 | 0.7832669 | 0.7644361 | 0.8002676 |
| SA0297 | | 485 | 0.7751156 | 0.7560678 | 0.7923466 |
| SA0298 | | 110 | 0.2871114 | 0.2738437 | 0.2998845 |
| SA0300 | | 395 | 0.7033706 | 0.6830639 | 0.7220169 |
| SA0306 | | 674 | 0.8742744 | 0.8592354 | 0.8874586 |
| SA0309 | | 920 | 0.941017 | 0.9311813 | 0.9492945 |
| SA0318 | int | 1202 | 0.9752299 | 0.9697003 | 0.9796705 |
| SA0319 | | 710 | 0.8874561 | 0.8732312 | 0.8998524 |
| SA0320 | | 224 | 0.4980058 | 0.4787972 | 0.5161518 |
| SA0321 | | 716 | 0.8895146 | 0.8754246 | 0.901781 |
| SA0322 | | 215 | 0.4839115 | 0.4649714 | 0.5018306 |
| SA0323 | | 305 | 0.6087366 | 0.5882113 | 0.6278674 |
| SA0324 | | 149 | 0.3677175 | 0.3517255 | 0.383014 |
| SA0325 | | 788 | 0.9114679 | 0.8989654 | 0.9222229 |
| SA0326 | | 221 | 0.493351 | 0.4742287 | 0.5114244 |
| SA0327 | | 242 | 0.5250502 | 0.5053862 | 0.5435709 |
| SA0328 | | 362 | 0.6716721 | 0.6511307 | 0.6906376 |
| SA0329 | | 197 | 0.4545246 | 0.4362098 | 0.4719039 |
| SA0330 | | 377 | 0.68648 | 0.6660263 | 0.7053176 |
| SA0331 | | 188 | 0.4392094 | 0.4212542 | 0.456273 |
| SA0332 | | 248 | 0.5337373 | 0.5139443 | 0.5523609 |
| SA0333 | | 260 | 0.5506376 | 0.5306188 | 0.5694363 |
| SA0334 | | 158 | 0.384985 | 0.3684777 | 0.400751 |
| SA0335 | | 314 | 0.619422 | 0.5988525 | 0.6385653 |
| SA0336 | | 257 | 0.5464708 | 0.5265046 | 0.5652295 |
| SA0337 | | 218 | 0.488653 | 0.4696202 | 0.5066508 |

TABLE I-continued

| SANUMBER | GENE_NAME | SIZE | PROBABILITY | LOWER | UPPER |
|---|---|---|---|---|---|
| SA0338 | | 620 | 0.8515512 | 0.8352918 | 0.8659336 |
| SA0339 | | 416 | 0.7219296 | 0.7018457 | 0.7403072 |
| SA0340 | | 692 | 0.8810477 | 0.8664164 | 0.8938362 |
| SA0341 | | 797 | 0.9138857 | 0.9015762 | 0.9244588 |
| SA0342 | | 353 | 0.6624538 | 0.6418764 | 0.681481 |
| SA0343 | | 1238 | 0.9778269 | 0.9727129 | 0.9819093 |
| SA0344 | | 212 | 0.479126 | 0.4602817 | 0.4969632 |
| SA0345 | | 218 | 0.488653 | 0.4696202 | 0.5066508 |
| SA0346 | | 422 | 0.7270157 | 0.7070045 | 0.7453084 |
| SA0347 | | 401 | 0.7087961 | 0.6885477 | 0.7273704 |
| SA0348 | | 182 | 0.4287612 | 0.4110641 | 0.4455962 |
| SA0349 | | 254 | 0.5422654 | 0.5223543 | 0.5609816 |
| SA0350 | | 353 | 0.6624538 | 0.6418764 | 0.681481 |
| SA0351 | | 239 | 0.5206462 | 0.5010508 | 0.5391114 |
| SA0352 | | 203 | 0.4645016 | 0.4459648 | 0.482074 |
| SA0353 | | 398 | 0.7060958 | 0.6858177 | 0.7247066 |
| SA0354 | | 344 | 0.6529766 | 0.6323765 | 0.6720532 |
| SA0355 | | 305 | 0.6087366 | 0.5882113 | 0.6278674 |
| SA0356 | | 233 | 0.5117152 | 0.4922657 | 0.5300613 |
| SA0357 | cut | 539 | 0.8095389 | 0.7915281 | 0.8256863 |
| SA0358 | | 203 | 0.4645016 | 0.4459648 | 0.482074 |
| SA0359 | | 191 | 0.4443617 | 0.426283 | 0.461534 |
| SA0360 | | 200 | 0.4595361 | 0.4411085 | 0.4770137 |
| SA0361 | | 149 | 0.3677175 | 0.3517255 | 0.383014 |
| SA0362 | | 197 | 0.4545246 | 0.4362098 | 0.4719039 |
| SA0363 | | 272 | 0.5669254 | 0.5467212 | 0.5858603 |
| SA0364 | | 434 | 0.7369104 | 0.7170559 | 0.7550237 |
| SA0365 | | 311 | 0.615893 | 0.5953363 | 0.635034 |
| SA0366 | | 302 | 0.6051086 | 0.5846019 | 0.6242315 |
| SA0367 | | 1688 | 0.9944467 | 0.9926304 | 0.9957922 |
| SA0368 | | 1235 | 0.9776213 | 0.9724737 | 0.9817306 |
| SA0369 | clpP | 770 | 0.9064267 | 0.893534 | 0.9175506 |
| SA0370 | | 1160 | 0.9718131 | 0.9657627 | 0.976706 |
| SA0371 | | 275 | 0.5709042 | 0.5506598 | 0.5898675 |
| SA0372 | | 329 | 0.6365864 | 0.6159801 | 0.6557162 |
| SA0373 | | 398 | 0.7060958 | 0.6858177 | 0.7247066 |
| SA0374 | | 392 | 0.70062 | 0.6802859 | 0.7193009 |
| SA0375 | | 638 | 0.8595487 | 0.8436944 | 0.873531 |
| SA0376 | | 452 | 0.751084 | 0.7314902 | 0.7689063 |
| SA0377 | | 347 | 0.6561649 | 0.6355708 | 0.6752264 |
| SA0378 | | 155 | 0.3792822 | 0.3629423 | 0.394896 |
| SA0380 | | 821 | 0.9200152 | 0.9082134 | 0.930112 |
| SA0381 | | 1580 | 0.9922579 | 0.9899101 | 0.9940286 |
| SA0382 | | 287 | 0.5864574 | 0.5660748 | 0.6055122 |
| SA0383 | | 1907 | 0.9971691 | 0.9961027 | 0.9979308 |
| SA0384 | | 1463 | 0.9889034 | 0.9858192 | 0.9912752 |
| SA0385 | | 386 | 0.6950422 | 0.6746566 | 0.713789 |
| SA0386 | | 161 | 0.3906354 | 0.373965 | 0.4065492 |
| SA0387 | | 296 | 0.5977512 | 0.5772879 | 0.6168528 |
| SA0388 | | 299 | 0.6014469 | 0.5809609 | 0.6205601 |
| SA0389 | | 1451 | 0.9884861 | 0.9853154 | 0.9909292 |
| SA0390 | | 119 | 0.3065803 | 0.2926085 | 0.3200112 |
| SA0393 | | 89 | 0.2395316 | 0.2281006 | 0.250575 |
| SA0406 | | 437 | 0.7393275 | 0.7195144 | 0.7573941 |
| SA0414 | | 851 | 0.9270673 | 0.915884 | 0.9365873 |
| SA0417 | | 653 | 0.8658832 | 0.8503681 | 0.8795322 |
| SA0418 | | 227 | 0.5026178 | 0.4833259 | 0.5208334 |
| SA0420 | | 200 | 0.4595361 | 0.4411085 | 0.4770137 |
| SA0422 | | 128 | 0.3255175 | 0.3108884 | 0.3395593 |
| SA0424 | | 626 | 0.8542664 | 0.8381417 | 0.8685155 |
| SA0434 | | 200 | 0.4595361 | 0.4411085 | 0.4770137 |
| SA0436 | | 188 | 0.4392094 | 0.4212542 | 0.456273 |
| SA0437 | rpsF | 275 | 0.5709042 | 0.5506598 | 0.5898675 |
| SA0438 | | 500 | 0.7852581 | 0.7664829 | 0.8022002 |
| SA0439 | rpsR | 239 | 0.5206462 | 0.5010508 | 0.5391114 |
| SA0440 | | 935 | 0.9436772 | 0.9341196 | 0.9517005 |
| SA0444 | | 569 | 0.8263314 | 0.8089502 | 0.841837 |
| SA0445 | | 260 | 0.5506376 | 0.5306188 | 0.5694363 |
| SA0447 | | 578 | 0.8310743 | 0.8138871 | 0.8463838 |
| SA0450 | | 290 | 0.5902568 | 0.5698451 | 0.6093292 |
| SA0464 | | 269 | 0.5629096 | 0.5427482 | 0.581814 |
| SA0465 | | 149 | 0.3677175 | 0.3517255 | 0.383014 |
| SA0468 | | 677 | 0.8754295 | 0.8604585 | 0.8885475 |
| SA0471 | | 134 | 0.3378541 | 0.3228118 | 0.3522782 |
| SA0474 | | 680 | 0.876574 | 0.8616709 | 0.8896259 |
| SA0475 | | 98 | 0.2602999 | 0.2480474 | 0.2721192 |
| SA0480 | | 305 | 0.6087366 | 0.5882113 | 0.6278674 |
| SA0482 | | 788 | 0.9114679 | 0.8989654 | 0.9222229 |

TABLE I-continued

| SANUMBER | GENE_NAME | SIZE | PROBABILITY | LOWER | UPPER |
|---|---|---|---|---|---|
| SA0483 | | 773 | 0.9072864 | 0.8944591 | 0.9183483 |
| SA0485 | | 782 | 0.9098184 | 0.8971864 | 0.9206956 |
| SA0486 | | 734 | 0.8954669 | 0.8817798 | 0.907347 |
| SA0488 | | 320 | 0.6263829 | 0.6057933 | 0.6455259 |
| SA0492 | | 140 | 0.3499651 | 0.3345289 | 0.3647521 |
| SA0493 | | 125 | 0.3192633 | 0.3048482 | 0.3331066 |
| SA0498 | | 671 | 0.8731086 | 0.8580015 | 0.886359 |
| SA0500 | | 113 | 0.293661 | 0.2801533 | 0.3066588 |
| SA0504 | | 1022 | 0.9569039 | 0.9488503 | 0.9635678 |
| SA0508 | | 266 | 0.5588567 | 0.5387403 | 0.5777282 |
| SA0510 | | 482 | 0.7730304 | 0.7539297 | 0.7903178 |
| SA0511 | | 779 | 0.9089822 | 0.8962853 | 0.9199208 |
| SA0519 | | 521 | 0.7986937 | 0.7803212 | 0.8152148 |
| SA0520 | dnaX | 1694 | 0.9945483 | 0.9927579 | 0.9958732 |
| SA0524 | tmk | 614 | 0.8487854 | 0.8323918 | 0.863301 |
| SA0526 | holB | 923 | 0.9415589 | 0.9317793 | 0.9497851 |
| SA0528 | | 344 | 0.6529766 | 0.6323765 | 0.6720532 |
| SA0529 | | 722 | 0.8915355 | 0.8775801 | 0.9036726 |
| SA0530 | | 245 | 0.5294138 | 0.5096839 | 0.5479873 |
| SA0532 | | 152 | 0.3735265 | 0.3573583 | 0.3889839 |
| SA0533 | metS | 1970 | 0.9976679 | 0.9967553 | 0.9983129 |
| SA0535 | | 533 | 0.8059904 | 0.7878575 | 0.8222635 |
| SA0537 | | 260 | 0.5506376 | 0.5306188 | 0.5694363 |
| SA0538 | | 845 | 0.9257085 | 0.914403 | 0.9353421 |
| SA0539 | purR | 821 | 0.9200152 | 0.9082134 | 0.930112 |
| SA0541 | spoVG | 299 | 0.6014469 | 0.5809609 | 0.6205601 |
| SA0542 | | 128 | 0.3255175 | 0.3108884 | 0.3395593 |
| SA0543 | glmU | 1349 | 0.9842416 | 0.9802429 | 0.9873754 |
| SA0544 | prsA | 962 | 0.9481668 | 0.9390961 | 0.9557474 |
| SA0545 | rplY | 650 | 0.8646395 | 0.8490565 | 0.8783552 |
| SA0546 | pth | 569 | 0.8263314 | 0.8089502 | 0.841854 |
| SA0550 | | 260 | 0.5506376 | 0.5306188 | 0.5694363 |
| SA0551 | | 389 | 0.697844 | 0.6774835 | 0.7165584 |
| SA0552 | | 398 | 0.7060958 | 0.6858177 | 0.7247066 |
| SA0553 | | 1292 | 0.981221 | 0.9766796 | 0.9848139 |
| SA0558 | folP | 650 | 0.8646395 | 0.8490565 | 0.8783552 |
| SA0559 | folB | 362 | 0.6716721 | 0.6511307 | 0.6906376 |
| SA0560 | folK | 473 | 0.7666578 | 0.7474023 | 0.7841115 |
| SA0561 | | 89 | 0.2395316 | 0.2281006 | 0.250575 |
| SA0562 | lysS | 1484 | 0.9895977 | 0.9866596 | 0.9918492 |
| SA0567 | ctsR | 458 | 0.7556368 | 0.7361361 | 0.7733567 |
| SA0572 | radA | 1361 | 0.9848128 | 0.9809207 | 0.987857 |
| SA0574 | gltX | 1451 | 0.9884861 | 0.9853154 | 0.9909292 |
| SA0575 | cysE | 638 | 0.8595487 | 0.8436944 | 0.873531 |
| SA0577 | | 401 | 0.7087961 | 0.6885477 | 0.7273704 |
| SA0578 | | 743 | 0.8983217 | 0.8848347 | 0.9100106 |
| SA0581 | | 215 | 0.4839115 | 0.4649714 | 0.5018306 |
| SA0584 | rplA | 689 | 0.8799447 | 0.8652455 | 0.8927989 |
| SA0585 | rplJ | 497 | 0.7832669 | 0.7644361 | 0.8002676 |
| SA0586 | rplL | 365 | 0.6746886 | 0.6541621 | 0.693631 |
| SA0588 | rpoB | 3548 | 0.9999818 | 0.9999671 | 0.9999899 |
| SA0589 | rpoC | 3620 | 0.9999854 | 0.9999733 | 0.999992 |
| SA0590 | | 251 | 0.538021 | 0.5181676 | 0.5566922 |
| SA0591 | rpsL | 410 | 0.7167488 | 0.696596 | 0.7352078 |
| SA0592 | rpsG | 467 | 0.7623104 | 0.7429547 | 0.7798722 |
| SA0593 | fusA | 2078 | 0.9983272 | 0.9976301 | 0.9988112 |
| SA0594 | tuf | 1181 | 0.9735767 | 0.9677916 | 0.9782387 |
| SA0600 | ilvE | 1073 | 0.9631622 | 0.9559027 | 0.9691183 |
| SA0601 | | 170 | 0.4072771 | 0.3901425 | 0.4236096 |
| SA0604 | | 614 | 0.8487854 | 0.8323918 | 0.863301 |
| SA0607 | | 563 | 0.8230957 | 0.8055863 | 0.8387312 |
| SA0610 | sdrE | 3497 | 0.9999787 | 0.9999618 | 0.999988 |
| SA0617 | | 629 | 0.8556053 | 0.8395481 | 0.8697877 |
| SA0618 | | 500 | 0.7852581 | 0.7664829 | 0.8022002 |
| SA0622 | atoB | 1136 | 0.9696531 | 0.963287 | 0.9748218 |
| SA0624 | | 266 | 0.5588567 | 0.5387403 | 0.5777282 |
| SA0625 | | 164 | 0.3962339 | 0.3794046 | 0.4122914 |
| SA0628 | | 377 | 0.68648 | 0.6660263 | 0.7053176 |
| SA0629 | | 365 | 0.6746886 | 0.6541621 | 0.693631 |
| SA0634 | | 983 | 0.9514098 | 0.9427053 | 0.9586591 |
| SA0636 | mvk | 917 | 0.9404701 | 0.9305781 | 0.948799 |
| SA0637 | | 980 | 0.9509593 | 0.9422031 | 0.9582552 |
| SA0638 | | 1073 | 0.9631622 | 0.9559027 | 0.9691183 |
| SA0639 | | 338 | 0.6465111 | 0.6259037 | 0.6656136 |
| SA0641 | | 437 | 0.7393275 | 0.7195144 | 0.7573941 |
| SA0642 | | 98 | 0.2602999 | 0.2480474 | 0.2721192 |
| SA0644 | | 623 | 0.852915 | 0.836723 | 0.8672308 |
| SA0645 | | 638 | 0.8595487 | 0.8436944 | 0.873531 |

TABLE I-continued

| SANUMBER | GENE_NAME | SIZE | PROBABILITY | LOWER | UPPER |
|---|---|---|---|---|---|
| SA0647 | | 626 | 0.8542664 | 0.8381417 | 0.8685155 |
| SA0648 | | 617 | 0.8501747 | 0.8338481 | 0.8646237 |
| SA0649 | | 638 | 0.8595487 | 0.8436944 | 0.873531 |
| SA0650 | | 626 | 0.8542664 | 0.8381417 | 0.8685155 |
| SA0651 | | 626 | 0.8542664 | 0.8381417 | 0.8685155 |
| SA0652 | | 647 | 0.8633844 | 0.8477335 | 0.8771667 |
| SA0653 | | 632 | 0.8569319 | 0.8409423 | 0.8710476 |
| SA0654 | | 623 | 0.852915 | 0.836723 | 0.8672308 |
| SA0656 | | 533 | 0.8059904 | 0.7878575 | 0.8222635 |
| SA0657 | | 473 | 0.7666578 | 0.7474023 | 0.7841115 |
| SA0658 | | 1292 | 0.981221 | 0.9766796 | 0.9848139 |
| SA0659 | | 518 | 0.7968271 | 0.7783957 | 0.8134093 |
| SA0660 | adh | 1007 | 0.9548684 | 0.9465689 | 0.9617529 |
| SA0662 | | 425 | 0.7295237 | 0.7095503 | 0.7477728 |
| SA0663 | argS | 1658 | 0.9939097 | 0.9919584 | 0.9953625 |
| SA0664 | | 632 | 0.8569319 | 0.8409423 | 0.8710476 |
| SA0666 | | 947 | 0.9457187 | 0.9363797 | 0.9535429 |
| SA0667 | | 716 | 0.8895146 | 0.8754246 | 0.901781 |
| SA0670 | | 713 | 0.8884901 | 0.8743327 | 0.9008214 |
| SA0671 | | 785 | 0.910647 | 0.8980798 | 0.921463 |
| SA0672 | sarA | 371 | 0.6806387 | 0.6601459 | 0.6995311 |
| SA0673 | | 116 | 0.3001504 | 0.2864081 | 0.3133675 |
| SA0674 | | 146 | 0.3618545 | 0.3460432 | 0.3769858 |
| SA0676 | | 221 | 0.493351 | 0.4742287 | 0.5114244 |
| SA0680 | | 422 | 0.7270157 | 0.7070045 | 0.7453084 |
| SA0683 | | 190 | 0.4426495 | 0.4246116 | 0.459786 |
| SA0685 | | 299 | 0.6014469 | 0.5809609 | 0.6205601 |
| SA0686 | | 434 | 0.7369104 | 0.7170559 | 0.7550237 |
| SA0688 | | 926 | 0.9420958 | 0.9323721 | 0.9502709 |
| SA0689 | | 833 | 0.9229144 | 0.9113622 | 0.9327779 |
| SA0690 | | 740 | 0.8973789 | 0.8838253 | 0.9091313 |
| SA0694 | | 791 | 0.9122813 | 0.8998433 | 0.9229754 |
| SA0695 | | 830 | 0.9221996 | 0.9105853 | 0.9321211 |
| SA0696 | tagB | 1100 | 0.9660987 | 0.9592337 | 0.9717058 |
| SA0698 | tagD | 395 | 0.7033706 | 0.6830639 | 0.7220169 |
| SA0702 | | 89 | 0.2395316 | 0.2281006 | 0.250575 |
| SA0703 | | 830 | 0.9221996 | 0.9105853 | 0.9321211 |
| SA0707 | | 965 | 0.948643 | 0.9396253 | 0.9561756 |
| SA0708 | | 581 | 0.8326263 | 0.8155043 | 0.8478702 |
| SA0709 | | 359 | 0.6686277 | 0.6480728 | 0.687615 |
| SA0710 | | 494 | 0.7812572 | 0.7623713 | 0.7983162 |
| SA0711 | | 1064 | 0.9621279 | 0.954733 | 0.9682043 |
| SA0713 | | 425 | 0.7295237 | 0.7095503 | 0.7477728 |
| SA0714 | | 503 | 0.787231 | 0.7685119 | 0.8041141 |
| SA0716 | | 680 | 0.876574 | 0.8616709 | 0.8896259 |
| SA0717 | | 1037 | 0.9588476 | 0.9510342 | 0.9652966 |
| SA0721 | | 614 | 0.8487854 | 0.8323918 | 0.863301 |
| SA0722 | | 1004 | 0.9544499 | 0.9461006 | 0.9613792 |
| SA0728 | | 470 | 0.7644941 | 0.7451882 | 0.7820021 |
| SA0729 | | 116 | 0.3001504 | 0.2864081 | 0.3133675 |
| SA0730 | | 641 | 0.8608391 | 0.8450525 | 0.8747547 |
| SA0731 | | 863 | 0.9297108 | 0.9187697 | 0.9390062 |
| SA0732 | | 221 | 0.493351 | 0.4742287 | 0.5114244 |
| SA0736 | | 440 | 0.7417224 | 0.7219516 | 0.7597415 |
| SA0737 | | 392 | 0.70062 | 0.6802859 | 0.7193009 |
| SA0738 | | 296 | 0.5977512 | 0.5772879 | 0.6168528 |
| SA0739 | | 539 | 0.8095389 | 0.7915281 | 0.8256863 |
| SA0741 | | 455 | 0.7533709 | 0.7338233 | 0.7711423 |
| SA0742 | | 680 | 0.876574 | 0.8616709 | 0.8896259 |
| SA0746 | | 440 | 0.7417224 | 0.7219516 | 0.7597415 |
| SA0755 | | 461 | 0.7578819 | 0.7384289 | 0.7755497 |
| SA0771 | | 416 | 0.7219296 | 0.7018457 | 0.7403072 |
| SA0778 | | 1937 | 0.9974187 | 0.9964284 | 0.9981225 |
| SA0783 | opuBB | 1511 | 0.9904269 | 0.9876673 | 0.9925322 |
| SA0784 | hisC | 1055 | 0.9610646 | 0.9535322 | 0.9672632 |
| SA0786 | | 158 | 0.384985 | 0.3684777 | 0.400751 |
| SA0787 | | 914 | 0.9399181 | 0.9299696 | 0.9482988 |
| SA0791 | nrdI | 395 | 0.7033706 | 0.6830639 | 0.7220169 |
| SA0793 | nrdF | 968 | 0.9491149 | 0.9401499 | 0.9565997 |
| SA0795 | | 152 | 0.3735265 | 0.3573583 | 0.3889839 |
| SA0797 | | 953 | 0.9467115 | 0.9374805 | 0.9544376 |
| SA0799 | | 1025 | 0.9572999 | 0.9492947 | 0.9639203 |
| SA0801 | murB | 920 | 0.941017 | 0.9311813 | 0.9492945 |
| SA0804 | | 317 | 0.6229185 | 0.602338 | 0.6420625 |
| SA0805 | | 1121 | 0.9682197 | 0.9616495 | 0.9735675 |
| SA0814 | | 671 | 0.8731086 | 0.8580015 | 0.886359 |
| SA0816 | secA | 2528 | 0.999581 | 0.9993599 | 0.9997235 |
| SA0819 | | 104 | 0.2738294 | 0.2610581 | 0.2861368 |

TABLE I-continued

| SANUMBER | GENE_NAME | SIZE | PROBABILITY | LOWER | UPPER |
|---|---|---|---|---|---|
| SA0822 | | 233 | 0.5117152 | 0.4922657 | 0.5300613 |
| SA0826 | lgt | 836 | 0.9236226 | 0.9121324 | 0.9334283 |
| SA0829 | | 932 | 0.9431549 | 0.9335422 | 0.9512286 |
| SA0831 | | 992 | 0.9527368 | 0.9441859 | 0.9598476 |
| SA0832 | | 941 | 0.9447074 | 0.9352595 | 0.9526307 |
| SA0836 | | 143 | 0.3559372 | 0.3403112 | 0.3708987 |
| SA0838 | gap | 1007 | 0.9548684 | 0.9465689 | 0.9617529 |
| SA0840 | tpiA | 758 | 0.9029075 | 0.8897519 | 0.9142808 |
| SA0842 | eno | 1301 | 0.9817338 | 0.9772823 | 0.9852504 |
| SA0843 | | 455 | 0.7533709 | 0.7338233 | 0.7711423 |
| SA0844 | secG | 272 | 0.5669254 | 0.5467212 | 0.5858603 |
| SA0847 | smpB | 461 | 0.7578819 | 0.7384289 | 0.7755497 |
| SA0848 | | 278 | 0.5748465 | 0.5545641 | 0.5938359 |
| SA0849 | | 320 | 0.6263829 | 0.6057933 | 0.6455259 |
| SA0850 | | 143 | 0.3559372 | 0.3403112 | 0.3708987 |
| SA0851 | | 725 | 0.892532 | 0.8786438 | 0.9046046 |
| SA0852 | | 89 | 0.2395316 | 0.2281006 | 0.250575 |
| SA0853 | | 152 | 0.3735265 | 0.3573583 | 0.3889839 |
| SA0855 | | 527 | 0.8023757 | 0.7841222 | 0.8187734 |
| SA0859 | | 467 | 0.7623104 | 0.7429547 | 0.7798722 |
| SA0861 | cspC | 197 | 0.4545246 | 0.4362098 | 0.4719039 |
| SA0862 | | 215 | 0.4839115 | 0.4649714 | 0.5018306 |
| SA0863 | | 281 | 0.5787526 | 0.5584345 | 0.5977659 |
| SA0864 | | 566 | 0.824721 | 0.8072756 | 0.8402917 |
| SA0866 | | 101 | 0.2670958 | 0.2545811 | 0.2791621 |
| SA0867 | | 143 | 0.3559372 | 0.3403112 | 0.3708987 |
| SA0868 | | 233 | 0.5117152 | 0.4922657 | 0.5300613 |
| SA0869 | | 587 | 0.8356876 | 0.8186965 | 0.8507999 |
| SA0873 | aroD | 713 | 0.8884901 | 0.8743327 | 0.9008214 |
| SA0874 | | 536 | 0.8077728 | 0.7897008 | 0.8239832 |
| SA0875 | | 317 | 0.6229185 | 0.602338 | 0.6420625 |
| SA0876 | | 353 | 0.6624538 | 0.6418764 | 0.681481 |
| SA0878 | | 110 | 0.2871114 | 0.2738437 | 0.2998845 |
| SA0880 | | 383 | 0.6922144 | 0.6718049 | 0.7109926 |
| SA0881 | | 293 | 0.5940213 | 0.5735828 | 0.6131093 |
| SA0884 | | 818 | 0.9192736 | 0.9074089 | 0.9294291 |
| SA0885 | | 1217 | 0.976347 | 0.970994 | 0.9806352 |
| SA0886 | ent | 725 | 0.892532 | 0.8786438 | 0.9046046 |
| SA0887 | sei | 725 | 0.892532 | 0.8786438 | 0.9046046 |
| SA0888 | | 428 | 0.7320087 | 0.7120741 | 0.7502133 |
| SA0889 | | 455 | 0.7533709 | 0.7338233 | 0.7711423 |
| SA0890 | | 329 | 0.6365864 | 0.6159801 | 0.6557162 |
| SA0891 | | 260 | 0.5506376 | 0.5306188 | 0.5694363 |
| SA0892 | | 269 | 0.5629096 | 0.5427482 | 0.581814 |
| SA0893 | | 143 | 0.3559372 | 0.3403112 | 0.3708987 |
| SA0894 | | 206 | 0.4694214 | 0.4507788 | 0.4870854 |
| SA0895 | | 317 | 0.6229185 | 0.602338 | 0.6420625 |
| SA0896 | | 779 | 0.9089822 | 0.8962853 | 0.9199208 |
| SA0897 | | 1454 | 0.9885919 | 0.985443 | 0.9910169 |
| SA0898 | | 359 | 0.6686277 | 0.6480728 | 0.687615 |
| SA0899 | | 281 | 0.5787526 | 0.5584345 | 0.5977659 |
| SA0900 | | 638 | 0.8595487 | 0.8436944 | 0.873531 |
| SA0901 | | 338 | 0.6465111 | 0.6259037 | 0.6656136 |
| SA0902 | | 575 | 0.8295079 | 0.8122558 | 0.8448829 |
| SA0903 | | 215 | 0.4839115 | 0.4649714 | 0.5018306 |
| SA0904 | | 524 | 0.8005432 | 0.78223 | 0.8170027 |
| SA0905 | | 338 | 0.6465111 | 0.6259037 | 0.6656136 |
| SA0906 | | 566 | 0.824721 | 0.8072756 | 0.8402917 |
| SA0907 | seb | 797 | 0.9138857 | 0.9015762 | 0.9244588 |
| SA0908 | | 554 | 0.8181289 | 0.8004292 | 0.8339579 |
| SA0909 | | 149 | 0.3677175 | 0.3517255 | 0.383014 |
| SA0910 | | 107 | 0.280501 | 0.2674788 | 0.2930441 |
| SA0911 | | 197 | 0.4545246 | 0.4362098 | 0.4719039 |
| SA0912 | | 191 | 0.4443617 | 0.426283 | 0.461534 |
| SA0914 | | 758 | 0.9029075 | 0.8897519 | 0.9142808 |
| SA0916 | | 1238 | 0.9778269 | 0.9727129 | 0.9819093 |
| SA0918 | | 1394 | 0.9862791 | 0.9826671 | 0.9890887 |
| SA0919 | | 134 | 0.3378541 | 0.3228118 | 0.3522782 |
| SA0920 | | 311 | 0.615893 | 0.5953363 | 0.635034 |
| SA0922 | | 1064 | 0.9621279 | 0.954733 | 0.9682043 |
| SA0923 | | 95 | 0.2534409 | 0.2414564 | 0.2650075 |
| SA0925 | | 824 | 0.9207501 | 0.9090109 | 0.9307882 |
| SA0928 | | 389 | 0.697844 | 0.6774835 | 0.7165584 |
| SA0929 | | 254 | 0.5422654 | 0.5223543 | 0.5609816 |
| SA0933 | | 107 | 0.280501 | 0.2674788 | 0.2930441 |
| SA0934 | | 200 | 0.4595361 | 0.4411085 | 0.4770137 |
| SA0935 | dltA | 1454 | 0.9885919 | 0.985443 | 0.9910169 |
| SA0936 | dltB | 1211 | 0.9759064 | 0.9704833 | 0.9802549 |

TABLE I-continued

| SANUMBER | GENE_NAME | SIZE | PROBABILITY | LOWER | UPPER |
|---|---|---|---|---|---|
| SA0937 | dltC | 233 | 0.5117152 | 0.4922657 | 0.5300613 |
| SA0938 | dltD | 1172 | 0.9728348 | 0.9669372 | 0.9775946 |
| SA0939 | nifU-3 | 239 | 0.5206462 | 0.5010508 | 0.5391114 |
| SA0940 | | 320 | 0.6263829 | 0.6057933 | 0.6455259 |
| SA0942 | | 233 | 0.5117152 | 0.4922657 | 0.5300613 |
| SA0943 | | 356 | 0.665555 | 0.6449881 | 0.6845629 |
| SA0947 | yuxO | 371 | 0.6806387 | 0.6601459 | 0.6995311 |
| SA0949 | mnhG | 353 | 0.6624538 | 0.6418764 | 0.681481 |
| SA0950 | mnhF | 290 | 0.5902568 | 0.5698451 | 0.6093292 |
| SA0952 | mnhD | 1493 | 0.9898818 | 0.9870043 | 0.9920836 |
| SA0953 | mnhC | 338 | 0.6465111 | 0.6259037 | 0.6656136 |
| SA0954 | mnhB | 425 | 0.7295237 | 0.7095503 | 0.7477728 |
| SA0955 | mnhA | 2402 | 0.9993827 | 0.9990766 | 0.999584 |
| SA0961 | gluD | 1241 | 0.9780306 | 0.97295 | 0.9820844 |
| SA0965 | | 131 | 0.3317143 | 0.3168761 | 0.3459497 |
| SA0969 | | 581 | 0.8326263 | 0.8155043 | 0.8478702 |
| SA0972 | | 104 | 0.2738294 | 0.2610581 | 0.2861368 |
| SA0976 | | 821 | 0.9200152 | 0.9082134 | 0.930112 |
| SA0977 | | 263 | 0.5547661 | 0.5346972 | 0.5736024 |
| SA0982 | | 638 | 0.8595487 | 0.8436944 | 0.873531 |
| SA0983 | | 1115 | 0.9676276 | 0.9609743 | 0.9730485 |
| SA0984 | | 512 | 0.7930417 | 0.7744939 | 0.8097454 |
| SA0985 | | 431 | 0.7344708 | 0.7145759 | 0.7526302 |
| SA0986 | | 182 | 0.4287612 | 0.4110641 | 0.4455962 |
| SA0987 | fabH | 938 | 0.9441946 | 0.9346921 | 0.9521679 |
| SA0988 | fabF | 1241 | 0.9780306 | 0.97295 | 0.9820844 |
| SA0989 | | 368 | 0.6776774 | 0.6571671 | 0.6965954 |
| SA0990 | | 95 | 0.2534409 | 0.2414564 | 0.2650075 |
| SA0996 | | 1712 | 0.994842 | 0.9931274 | 0.9961071 |
| SA0997 | | 983 | 0.9514098 | 0.9427053 | 0.9586591 |
| SA0998 | | 977 | 0.9505045 | 0.9416965 | 0.9578473 |
| SA0999 | | 959 | 0.9476862 | 0.9385623 | 0.9553151 |
| SA1000 | oppC | 878 | 0.9328809 | 0.922238 | 0.9419005 |
| SA1001 | trpS | 986 | 0.9518563 | 0.9432031 | 0.9590591 |
| SA1002 | | 392 | 0.70062 | 0.6802859 | 0.7193009 |
| SA1004 | | 983 | 0.9514098 | 0.9427053 | 0.9586591 |
| SA1009 | | 344 | 0.6529766 | 0.6323765 | 0.6720532 |
| SA1010 | relA | 632 | 0.8569319 | 0.8409423 | 0.8710476 |
| SA1011 | | 806 | 0.9162375 | 0.9041196 | 0.9266304 |
| SA1012 | | 851 | 0.9270673 | 0.915884 | 0.9365873 |
| SA1016 | fabI | 767 | 0.9055591 | 0.8926008 | 0.916745 |
| SA1019 | | 755 | 0.9020072 | 0.8887856 | 0.9134432 |
| SA1023 | | 1478 | 0.9894039 | 0.9864247 | 0.9916892 |
| SA1024 | | 257 | 0.5464708 | 0.5265046 | 0.5652295 |
| SA1027 | | 92 | 0.2465183 | 0.2348076 | 0.2578263 |
| SA1028 | | 1439 | 0.9880531 | 0.9847938 | 0.9905694 |
| SA1029 | | 857 | 0.9284013 | 0.9173395 | 0.9378085 |
| SA1030 | | 1355 | 0.9845299 | 0.9805847 | 0.9876185 |
| SA1031 | | 1508 | 0.9903381 | 0.9875592 | 0.9924592 |
| SA1032 | | 527 | 0.8023757 | 0.7841222 | 0.8187734 |
| SA1033 | | 215 | 0.4839115 | 0.4649714 | 0.5018306 |
| SA1034 | | 983 | 0.9514098 | 0.9427053 | 0.9586591 |
| SA1035 | | 173 | 0.4127227 | 0.3954416 | 0.4291866 |
| SA1037 | | 104 | 0.2738294 | 0.2610581 | 0.2861368 |
| SA1039 | | 317 | 0.6229185 | 0.602338 | 0.6420625 |
| SA1041 | | 287 | 0.5864574 | 0.5660748 | 0.6055122 |
| SA1042 | | 284 | 0.5826228 | 0.5622713 | 0.6016579 |
| SA1045 | | 956 | 0.9472011 | 0.9380237 | 0.9548785 |
| SA1046 | | 128 | 0.3255175 | 0.3108884 | 0.3395593 |
| SA1047 | | 287 | 0.5864574 | 0.5660748 | 0.6055122 |
| SA1050 | | 101 | 0.2670958 | 0.2545811 | 0.2791621 |
| SA1051 | | 1208 | 0.9756829 | 0.9702246 | 0.980062 |
| SA1054 | | 818 | 0.9192736 | 0.9074089 | 0.9294291 |
| SA1055 | | 326 | 0.6332166 | 0.6126141 | 0.6523524 |
| SA1060 | | 416 | 0.7219296 | 0.7018457 | 0.7403072 |
| SA1061 | | 107 | 0.280501 | 0.2674788 | 0.2930441 |
| SA1065 | | 1214 | 0.9761277 | 0.9707398 | 0.980446 |
| SA1067 | | 275 | 0.5709042 | 0.5506598 | 0.5898675 |
| SA1072 | folD | 857 | 0.9284013 | 0.9173395 | 0.9378085 |
| SA1073 | purE | 416 | 0.7219296 | 0.7018457 | 0.7403072 |
| SA1074 | purK | 1121 | 0.9682197 | 0.9616495 | 0.9735675 |
| SA1075 | purC | 701 | 0.8842963 | 0.8698684 | 0.8968882 |
| SA1077 | purQ | 668 | 0.871932 | 0.8567569 | 0.8852487 |
| SA1081 | purN | 563 | 0.8230957 | 0.8055863 | 0.8387312 |
| SA1084 | | 803 | 0.9154608 | 0.9032792 | 0.9259136 |
| SA1086 | | 572 | 0.827927 | 0.8106102 | 0.8433673 |
| SA1090 | | 539 | 0.8095389 | 0.7915281 | 0.8256863 |
| SA1091 | | 263 | 0.5547661 | 0.5346972 | 0.5736024 |

TABLE I-continued

| SANUMBER | GENE_NAME | SIZE | PROBABILITY | LOWER | UPPER |
|---|---|---|---|---|---|
| SA1093 | | 230 | 0.5071875 | 0.4878153 | 0.5254698 |
| SA1097 | | 176 | 0.4181183 | 0.4006946 | 0.4347098 |
| SA1098 | | 1694 | 0.9945483 | 0.9927579 | 0.9958732 |
| SA1099 | | 215 | 0.4839115 | 0.4649714 | 0.5018306 |
| SA1100 | def | 548 | 0.8147404 | 0.7969153 | 0.8306975 |
| SA1101 | | 623 | 0.852915 | 0.836723 | 0.8672308 |
| SA1102 | pdhA | 1109 | 0.9670245 | 0.9602872 | 0.9725192 |
| SA1103 | pdhB | 974 | 0.9500456 | 0.9411854 | 0.9574355 |
| SA1104 | pdhC | 1289 | 0.9810468 | 0.9764752 | 0.9846655 |
| SA1107 | | 536 | 0.8077728 | 0.7897008 | 0.8239832 |
| SA1108 | | 1091 | 0.9651468 | 0.9581523 | 0.9708684 |
| SA1109 | | 794 | 0.9130872 | 0.9007135 | 0.9237207 |
| SA1110 | | 806 | 0.9162375 | 0.9041196 | 0.9266304 |
| SA1117 | | 188 | 0.4392094 | 0.4212542 | 0.456273 |
| SA1119 | | 164 | 0.3962339 | 0.3794046 | 0.4122914 |
| SA1120 | | 479 | 0.7709258 | 0.7517728 | 0.7882691 |
| SA1122 | | 1223 | 0.9767797 | 0.9714959 | 0.9810081 |
| SA1126 | | 458 | 0.7556368 | 0.7361361 | 0.7733567 |
| SA1127 | | 200 | 0.4595361 | 0.4411085 | 0.4770137 |
| SA1129 | | 431 | 0.7344708 | 0.7145759 | 0.7526302 |
| SA1131 | | 251 | 0.538021 | 0.5181676 | 0.5566922 |
| SA1132 | | 386 | 0.6950422 | 0.6746566 | 0.713789 |
| SA1133 | | 539 | 0.8095389 | 0.7915281 | 0.8256863 |
| SA1134 | kdtB | 479 | 0.7709258 | 0.7517728 | 0.7882691 |
| SA1137 | rpmF | 170 | 0.4072771 | 0.3901425 | 0.4236096 |
| SA1140 | | 205 | 0.4677865 | 0.4491788 | 0.4854204 |
| SA1141 | | 680 | 0.876574 | 0.8616709 | 0.8896259 |
| SA1144 | | 962 | 0.9481668 | 0.9390961 | 0.9557474 |
| SA1145 | | 731 | 0.8944976 | 0.8807435 | 0.9064417 |
| SA1146 | | 320 | 0.6263829 | 0.6057933 | 0.6455259 |
| SA1147 | | 737 | 0.8964273 | 0.882807 | 0.9082435 |
| SA1148 | pheS | 1055 | 0.9610646 | 0.9535322 | 0.9672632 |
| SA1149 | pheT | 2399 | 0.9993769 | 0.9990685 | 0.99958 |
| SA1150 | rnhC | 935 | 0.9436772 | 0.9341196 | 0.9517005 |
| SA1151 | | 263 | 0.5547661 | 0.5346972 | 0.5736024 |
| SA1156 | | 92 | 0.2465183 | 0.2348076 | 0.2578263 |
| SA1161 | murI | 797 | 0.9138857 | 0.9015762 | 0.9244588 |
| SA1163 | | 500 | 0.7852581 | 0.7664829 | 0.8022002 |
| SA1164 | | 326 | 0.6332166 | 0.6126141 | 0.6523524 |
| SA1165 | | 104 | 0.2738294 | 0.2610581 | 0.2861368 |
| SA1166 | | 398 | 0.7060958 | 0.6858177 | 0.7247066 |
| SA1168 | fib | 494 | 0.7812572 | 0.7623713 | 0.7983162 |
| SA1169 | fib | 347 | 0.6561649 | 0.6355708 | 0.6752264 |
| SA1170 | | 242 | 0.5250502 | 0.5053862 | 0.5435709 |
| SA1171 | | 182 | 0.4287612 | 0.4110641 | 0.4455962 |
| SA1173 | | 956 | 0.9472011 | 0.9380237 | 0.9548785 |
| SA1174 | | 143 | 0.3559372 | 0.3403112 | 0.3708987 |
| SA1175 | | 194 | 0.4494666 | 0.431268 | 0.4667442 |
| SA1176 | | 245 | 0.5294138 | 0.5096839 | 0.5479873 |
| SA1177 | | 128 | 0.3255175 | 0.3108884 | 0.3395593 |
| SA1179 | | 722 | 0.8915355 | 0.8775801 | 0.9036726 |
| SA1181 | arcB | 998 | 0.9536013 | 0.9451516 | 0.9606208 |
| SA1185 | | 185 | 0.4340094 | 0.4161814 | 0.4509606 |
| SA1186 | | 131 | 0.3317143 | 0.3168761 | 0.3459497 |
| SA1187 | | 131 | 0.3317143 | 0.3168761 | 0.3459497 |
| SA1188 | | 692 | 0.8810477 | 0.8664164 | 0.8938362 |
| SA1189 | | 437 | 0.7393275 | 0.7195144 | 0.7573941 |
| SA1193 | | 398 | 0.7060958 | 0.6858177 | 0.7247066 |
| SA1194 | pbp1 | 2231 | 9.9989552 | 0.9984814 | 0.999276 |
| SA1195 | mraY | 962 | 0.9481668 | 0.9390961 | 0.9557474 |
| SA1196 | murD | 1346 | 0.9840955 | 0.9800697 | 0.9872521 |
| SA1197 | divIB | 1316 | 0.9825577 | 0.9782522 | 0.9859503 |
| SA1198 | ftsA | 1409 | 0.9868979 | 0.9834071 | 0.9896064 |
| SA1199 | ftsZ | 1169 | 0.9725829 | 0.9666474 | 0.9773757 |
| SA1200 | | 662 | 0.8695459 | 0.8542348 | 0.8829954 |
| SA1201 | | 671 | 0.8731086 | 0.8580015 | 0.886359 |
| SA1202 | ylmF | 560 | 0.8214554 | 0.8038822 | 0.8371556 |
| SA1204 | ylmH | 803 | 0.9154608 | 0.9032792 | 0.9259136 |
| SA1205 | | 614 | 0.8487854 | 0.8323918 | 0.863301 |
| SA1206 | ileS | 2750 | 0.9997884 | 0.9996645 | 0.9998653 |
| SA1209 | | 914 | 0.9399181 | 0.9299696 | 0.9482988 |
| SA1212 | pyrB | 878 | 0.9328809 | 0.922238 | 0.9419005 |
| SA1218 | | 209 | 0.4742961 | 0.455551 | 0.4920483 |
| SA1219 | | 398 | 0.7060958 | 0.6858177 | 0.7247066 |
| SA1222 | rpoZ | 215 | 0.4839115 | 0.4649714 | 0.5018306 |
| SA1225 | | 950 | 0.9462174 | 0.9369325 | 0.9539925 |
| SA1226 | | 275 | 0.5709042 | 0.5506598 | 0.5898675 |
| SA1234 | | 872 | 0.9316304 | 0.9208688 | 0.9407596 |

TABLE I-continued

| SANUMBER | GENE_NAME | SIZE | PROBABILITY | LOWER | UPPER |
|---|---|---|---|---|---|
| SA1235 | rpe | 641 | 0.8608391 | 0.8450525 | 0.8747547 |
| SA1236 | | 644 | 0.8621176 | 0.8463989 | 0.8759666 |
| SA1237 | | 92 | 0.2465183 | 0.2348076 | 0.2578263 |
| SA1238 | rpmB | 185 | 0.4340094 | 0.4161814 | 0.4509606 |
| SA1240 | | 1643 | 0.9936221 | 0.9915997 | 0.9951315 |
| SA1242 | | 569 | 0.8263314 | 0.8089502 | 0.841837 |
| SA1243 | plsX | 983 | 0.9514098 | 0.9427053 | 0.9586591 |
| SA1244 | fabD | 932 | 0.9431549 | 0.9335422 | 0.9512286 |
| SA1245 | fabG | 731 | 0.8944976 | 0.8807435 | 0.9064417 |
| SA1246 | | 95 | 0.2534409 | 0.2414564 | 0.2650075 |
| SA1247 | acpP | 230 | 0.5071875 | 0.4878153 | 0.5254698 |
| SA1248 | rnc | 728 | 0.8935193 | 0.8796982 | 0.9055276 |
| SA1251 | ftsY | 1247 | 0.9784325 | 0.9734181 | 0.9824294 |
| SA1252 | | 329 | 0.6365864 | 0.6159801 | 0.6557162 |
| SA1253 | ffh | 1364 | 0.9849523 | 0.9810864 | 0.9879745 |
| SA1254 | rpsP | 272 | 0.5669254 | 0.5467212 | 0.5858603 |
| SA1255 | rimM | 500 | 0.7852581 | 0.7664829 | 0.8022002 |
| SA1256 | trmD | 734 | 0.8954669 | 0.8817798 | 0.907347 |
| SA1257 | rplS | 347 | 0.6561649 | 0.6355708 | 0.6752264 |
| SA1260 | | 881 | 0.9334976 | 0.9229136 | 0.9424627 |
| SA1261 | rnhB | 764 | 0.9046833 | 0.8916595 | 0.9159316 |
| SA1263 | sucD | 905 | 0.9382312 | 0.9281119 | 0.9467685 |
| SA1264 | lytN | 1148 | 0.970753 | 0.9645465 | 0.9757822 |
| SA1269 | xerC | 893 | 0.9359081 | 0.9255582 | 0.9446574 |
| SA1270 | hsIV | 542 | 0.8112888 | 0.7933395 | 0.827373 |
| SA1273 | | 89 | 0.2395316 | 0.2281006 | 0.250575 |
| SA1274 | rpsB | 773 | 0.9072864 | 0.8944591 | 0.9183483 |
| SA1275 | | 110 | 0.2871114 | 0.2738437 | 0.2998845 |
| SA1276 | tsf | 878 | 0.9328809 | 0.922238 | 0.9419005 |
| SA1277 | pyrH | 719 | 0.8905297 | 0.876507 | 0.9027314 |
| SA1278 | frr | 551 | 0.8164424 | 0.7986799 | 0.8323356 |
| SA1279 | uppS | 767 | 0.9055591 | 0.8926008 | 0.916745 |
| SA1280 | cdsA | 779 | 0.9089822 | 0.8962853 | 0.9199208 |
| SA1282 | proS | 1700 | 0.994648 | 0.9928832 | 0.9959527 |
| SA1286 | | 281 | 0.5787526 | 0.5584345 | 0.5977659 |
| SA1287 | | 314 | 0.619422 | 0.5988525 | 0.6385653 |
| SA1291 | ribF | 968 | 0.9491149 | 0.9401499 | 0.9565997 |
| SA1292 | rpsO | 266 | 0.5588567 | 0.5387403 | 0.5777282 |
| SA1295 | | 2375 | 0.9993292 | 0.9990011 | 0.999546 |
| SA1296 | | 710 | 0.8874561 | 0.8732312 | 0.8998524 |
| SA1297 | | 1262 | 0.9794052 | 0.974553 | 0.9832631 |
| SA1299 | | 701 | 0.8842963 | 0.8698684 | 0.8968882 |
| SA1300 | | 824 | 0.9207501 | 0.9090109 | 0.9307882 |
| SA1301 | | 389 | 0.697844 | 0.6774835 | 0.7165584 |
| SA1302 | pgsA | 575 | 0.8295079 | 0.8122558 | 0.8448829 |
| SA1304 | | 1040 | 0.9592257 | 0.9514597 | 0.9656324 |
| SA1305 | | 1556 | 0.9916646 | 0.9891805 | 0.9935456 |
| SA1306 | | 212 | 0.479126 | 0.4602817 | 0.4969632 |
| SA1308 | | 1757 | 0.9955089 | 0.9939706 | 0.9966354 |
| SA1310 | | 290 | 0.5902568 | 0.5698451 | 0.6093292 |
| SA1311 | | 134 | 0.3378541 | 0.3228118 | 0.3522782 |
| SA1313 | | 362 | 0.6716721 | 0.6511307 | 0.6906376 |
| SA1315 | hexA | 2519 | 0.9995693 | 0.999343 | 0.9997153 |
| SA1317 | glpP | 539 | 0.8095389 | 0.7915281 | 0.8256863 |
| SA1318 | | 158 | 0.384985 | 0.3684777 | 0.400751 |
| SA1322 | | 911 | 0.939361 | 0.9293558 | 0.9477936 |
| SA1323 | miaA | 932 | 0.9431549 | 0.9335422 | 0.9512286 |
| SA1324 | | 230 | 0.5071875 | 0.4878153 | 0.5254698 |
| SA1325 | gpxA | 473 | 0.7666578 | 0.7474023 | 0.7841115 |
| SA1327 | | 1235 | 0.9776213 | 0.9724737 | 0.9817326 |
| SA1328 | glnR | 365 | 0.6746886 | 0.6541621 | 0.693631 |
| SA1330 | | 110 | 0.2871114 | 0.2738437 | 0.2998845 |
| SA1331 | | 194 | 0.4494666 | 0.431268 | 0.4667442 |
| SA1332 | | 221 | 0.493351 | 0.4742287 | 0.5114244 |
| SA1333 | | 203 | 0.4645016 | 0.4459648 | 0.482074 |
| SA1334 | | 107 | 0.280501 | 0.2674788 | 0.2930441 |
| SA1335 | | 182 | 0.4287612 | 0.4110641 | 0.4455962 |
| SA1336 | | 101 | 0.2670958 | 0.2545811 | 0.2791621 |
| SA1337 | | 92 | 0.2465183 | 0.2348076 | 0.2578263 |
| SA1338 | | 248 | 0.5337373 | 0.5139443 | 0.5523609 |
| SA1339 | | 581 | 0.8326263 | 0.8155043 | 0.8478702 |
| SA1340 | | 245 | 0.5294138 | 0.5096839 | 0.5479873 |
| SA1341 | | 98 | 0.2602999 | 0.2480474 | 0.2721192 |
| SA1342 | | 263 | 0.5547661 | 0.5346972 | 0.5736024 |
| SA1343 | | 134 | 0.3378541 | 0.3228118 | 0.3522782 |
| SA1344 | | 131 | 0.3317143 | 0.3168761 | 0.3459497 |
| SA1345 | | 287 | 0.5864574 | 0.5660748 | 0.6055122 |
| SA1346 | | 191 | 0.4443617 | 0.426283 | 0.461534 |

TABLE I-continued

| SANUMBER | GENE_NAME | SIZE | PROBABILITY | LOWER | UPPER |
|---|---|---|---|---|---|
| SA1347 | | 338 | 0.6465111 | 0.6259037 | 0.6656136 |
| SA1348 | | 188 | 0.4392094 | 0.4212542 | 0.456273 |
| SA1349 | | 1022 | 0.9569039 | 0.9488503 | 0.9635678 |
| SA1350 | | 194 | 0.4494666 | 0.431268 | 0.4667442 |
| SA1353 | | 728 | 0.8935193 | 0.8796982 | 0.9055276 |
| SA1354 | | 1088 | 0.9648236 | 0.9577855 | 0.9705837 |
| SA1355 | | 599 | 0.8416434 | 0.8249163 | 0.8564912 |
| SA1358 | | 851 | 0.9270673 | 0.915884 | 0.9365873 |
| SA1361 | | 104 | 0.2738294 | 0.2610581 | 0.2861368 |
| SA1366 | | 311 | 0.615893 | 0.5953363 | 0.635034 |
| SA1367 | | 1451 | 0.9884861 | 0.9853154 | 0.9909292 |
| SA1368 | | 1418 | 0.9872557 | 0.9838359 | 0.9899052 |
| SA1369 | rpmG | 155 | 0.3792822 | 0.3629423 | 0.394896 |
| SA1370 | rpsN | 266 | 0.5588567 | 0.5387403 | 0.5777282 |
| SA1372 | | 101 | 0.2670958 | 0.2545811 | 0.2791621 |
| SA1374 | lexA | 620 | 0.8515512 | 0.8352918 | 0.8659336 |
| SA1375 | | 230 | 0.5071875 | 0.4878153 | 0.5254698 |
| SA1378 | | 284 | 0.5826228 | 0.5622713 | 0.6016579 |
| SA1379 | | 95 | 0.2534409 | 0.2414564 | 0.2650075 |
| SA1380 | | 464 | 0.7601063 | 0.7407017 | 0.7777215 |
| SA1383 | mscL | 434 | 0.7369104 | 0.7170559 | 0.7550237 |
| SA1386 | | 464 | 0.7601063 | 0.7407017 | 0.7777215 |
| SA1388 | | 605 | 0.8445398 | 0.8279457 | 0.8592597 |
| SA1389 | parE | 1994 | 0.9978339 | 0.9969741 | 0.9984392 |
| SA1390 | parC | 2399 | 0.9993769 | 0.9990685 | 0.99958 |
| SA1391 | | 95 | 0.2534409 | 0.2414564 | 0.2650075 |
| SA1393 | | 848 | 0.926391 | 0.9151468 | 0.9359677 |
| SA1394 | | 164 | 0.3962339 | 0.3794046 | 0.4122914 |
| SA1397 | msrA | 506 | 0.7891858 | 0.7705234 | 0.8060095 |
| SA1399 | dmpI | 182 | 0.4287612 | 0.4110641 | 0.4455962 |
| SA1400 | | 1259 | 0.9792142 | 0.97433 | 0.9830996 |
| SA1404 | trpG | 563 | 0.8230957 | 0.8055863 | 0.8387312 |
| SA1406 | trpC | 779 | 0.9089822 | 0.8962853 | 0.9199208 |
| SA1407 | trpF | 629 | 0.8556053 | 0.8395481 | 0.8697877 |
| SA1409 | trpA | 683 | 0.8777079 | 0.8628729 | 0.8906939 |
| SA1410 | femA | 1259 | 0.9792142 | 0.97433 | 0.9830996 |
| SA1411 | | 1256 | 0.9790215 | 0.974105 | 0.9829345 |
| SA1412 | | 764 | 0.9046833 | 0.8916595 | 0.9159316 |
| SA1413 | | 470 | 0.7644941 | 0.7451882 | 0.7820021 |
| SA1414 | | 698 | 0.8832234 | 0.8687278 | 0.8958807 |
| SA1418 | | 341 | 0.6497588 | 0.6291542 | 0.6688491 |
| SA1421 | | 848 | 0.926391 | 0.9151468 | 0.9359677 |
| SA1422 | | 914 | 0.9399181 | 0.9299696 | 0.9482988 |
| SA1425 | | 293 | 0.5940213 | 0.5735828 | 0.6131093 |
| SA1426 | | 899 | 0.9370803 | 0.9268462 | 0.9457232 |
| SA1427 | | 1598 | 0.992675 | 0.9904248 | 0.994367 |
| SA1428 | | 1202 | 0.9752299 | 0.9697003 | 0.9796705 |
| SA1431 | dapB | 719 | 0.8905297 | 0.876507 | 0.9027314 |
| SA1433 | | 1148 | 0.970753 | 0.9645465 | 0.9757822 |
| SA1435 | lysA | 1262 | 0.9794052 | 0.974553 | 0.9832631 |
| SA1436 | | 398 | 0.7060958 | 0.6858177 | 0.7247066 |
| SA1437 | cspD | 197 | 0.4545246 | 0.4362098 | 0.4719039 |
| SA1438 | | 305 | 0.6087366 | 0.5882113 | 0.6278674 |
| SA1440 | | 626 | 0.8542664 | 0.8381417 | 0.8685155 |
| SA1441 | | 1133 | 0.9693717 | 0.9629652 | 0.9745758 |
| SA1442 | | 389 | 0.697844 | 0.6774835 | 0.7165584 |
| SA1446 | | 200 | 0.4595361 | 0.4411085 | 0.4770137 |
| SA1450 | arlS | 1352 | 0.9843864 | 0.9804145 | 0.9874976 |
| SA1451 | arlR | 656 | 0.8671154 | 0.8516683 | 0.8806979 |
| SA1452 | | 611 | 0.8473832 | 0.8309227 | 0.8619654 |
| SA1453 | murG | 1067 | 0.9624759 | 0.9551263 | 0.9685119 |
| SA1454 | | 293 | 0.5940213 | 0.5735828 | 0.6131093 |
| SA1456 | | 218 | 0.488653 | 0.4696202 | 0.5066508 |
| SA1458 | | 425 | 0.7295237 | 0.7095503 | 0.7477728 |
| SA1460 | degV | 836 | 0.9236226 | 0.9121324 | 0.9334283 |
| SA1461 | folA | 476 | 0.7688016 | 0.7495971 | 0.7862004 |
| SA1462 | thyA | 953 | 0.9467115 | 0.9374805 | 0.9544376 |
| SA1463 | | 92 | 0.2465183 | 0.2348076 | 0.2578263 |
| SA1464 | | 434 | 0.7369104 | 0.7170559 | 0.7550237 |
| SA1466 | | 248 | 0.5337373 | 0.5139443 | 0.5523609 |
| SA1467 | | 218 | 0.488653 | 0.4696202 | 0.5066508 |
| SA1468 | | 701 | 0.8842963 | 0.8698684 | 0.8968882 |
| SA1473 | | 179 | 0.4234643 | 0.405902 | 0.4401795 |
| SA1474 | | 95 | 0.2534409 | 0.2414564 | 0.2650075 |
| SA1477 | ilvA | 1037 | 0.9588476 | 0.9510342 | 0.9652966 |
| SA1481 | | 1337 | 0.983649 | 0.979541 | 0.9868747 |
| SA1482 | | 329 | 0.6365864 | 0.6159801 | 0.6557162 |
| SA1484 | divIVA | 341 | 0.6497588 | 0.6291542 | 0.6688491 |

TABLE I-continued

| SANUMBER | GENE_NAME | SIZE | PROBABILITY | LOWER | UPPER |
|---|---|---|---|---|---|
| SA1485 |  | 560 | 0.8214554 | 0.8038822 | 0.8371556 |
| SA1486 |  | 347 | 0.6561649 | 0.6355708 | 0.6752264 |
| SA1487 |  | 161 | 0.3906354 | 0.373965 | 0.4065492 |
| SA1488 |  | 122 | 0.312951 | 0.298755 | 0.3265907 |
| SA1489 | recU | 623 | 0.852915 | 0.836723 | 0.8672308 |
| SA1490 | pbp2 | 2180 | 0.9987778 | 0.9982386 | 0.9991458 |
| SA1492 | nth | 656 | 0.8671154 | 0.8516683 | 0.8806979 |
| SA1493 |  | 683 | 0.8777079 | 0.8628729 | 0.8906939 |
| SA1496 |  | 968 | 0.9491149 | 0.9401499 | 0.9565997 |
| SA1497 |  | 1097 | 0.9657843 | 0.9588764 | 0.9714294 |
| SA1498 |  | 1139 | 0.9699319 | 0.963606 | 0.9750654 |
| SA1499 |  | 314 | 0.619422 | 0.5988525 | 0.6385653 |
| SA1500 |  | 704 | 0.8853593 | 0.8709991 | 0.8978859 |
| SA1502 |  | 572 | 0.827927 | 0.8106102 | 0.8433673 |
| SA1504 | aroA | 1295 | 0.9813935 | 0.9768823 | 0.9849608 |
| SA1505 | aroB | 1061 | 0.9617768 | 0.9543362 | 0.9678936 |
| SA1506 | aroC | 1163 | 0.9720721 | 0.9660602 | 0.9769314 |
| SA1507 |  | 197 | 0.4545246 | 0.4362098 | 0.4719039 |
| SA1508 |  | 122 | 0.312951 | 0.298755 | 0.3265907 |
| SA1509 |  | 446 | 0.7464464 | 0.7267625 | 0.7643685 |
| SA1510 |  | 956 | 0.9472011 | 0.9380237 | 0.9548785 |
| SA1511 |  | 599 | 0.8416434 | 0.8249163 | 0.8564912 |
| SA1512 |  | 569 | 0.8263314 | 0.8089502 | 0.841837 |
| SA1513 | hup | 269 | 0.5629096 | 0.5427482 | 0.581814 |
| SA1515 | b2511 | 1307 | 0.9820679 | 0.9776753 | 0.9855345 |
| SA1516 | rpsA | 1172 | 0.9728348 | 0.9669372 | 0.9775946 |
| SA1517 |  | 113 | 0.293661 | 0.2801533 | 0.3066588 |
| SA1518 | cmk | 548 | 0.8147404 | 0.7969153 | 0.8306975 |
| SA1521 |  | 113 | 0.293661 | 0.2801533 | 0.3066588 |
| SA1525 |  | 245 | 0.5294138 | 0.5096839 | 0.5479873 |
| SA1527 |  | 116 | 0.3001504 | 0.2864081 | 0.3133675 |
| SA1535 | srrA | 722 | 0.8915355 | 0.8775801 | 0.9036726 |
| SA1536 | rluB | 734 | 0.8954669 | 0.8817798 | 0.907347 |
| SA1537 |  | 539 | 0.8095389 | 0.7915281 | 0.8256863 |
| SA1541 |  | 446 | 0.7464464 | 0.7267625 | 0.7643685 |
| SA1542 |  | 539 | 0.8095389 | 0.7915281 | 0.8256863 |
| SA1544 |  | 245 | 0.5294138 | 0.5096839 | 0.5479873 |
| SA1547 |  | 140 | 0.3499651 | 0.3345289 | 0.3647521 |
| SA1548 |  | 917 | 0.9404701 | 0.9305781 | 0.948799 |
| SA1551 | malA | 1646 | 0.9936807 | 0.9916727 | 0.9951786 |
| SA1552 |  | 1016 | 0.956101 | 0.9479497 | 0.9628524 |
| SA1553 |  | 368 | 0.6776774 | 0.6571671 | 0.6965954 |
| SA1556 |  | 176 | 0.4181183 | 0.4006946 | 0.4347098 |
| SA1557 |  | 977 | 0.9505045 | 0.9416965 | 0.9578473 |
| SA1558 |  | 434 | 0.7369104 | 0.7170559 | 0.7550237 |
| SA1559 |  | 95 | 0.2534409 | 0.2414564 | 0.2650075 |
| SA1562 |  | 989 | 0.9522986 | 0.9436966 | 0.9594553 |
| SA1564 | recN | 1535 | 0.9911083 | 0.9884989 | 0.993091 |
| SA1565 |  | 449 | 0.7487759 | 0.7291367 | 0.7666484 |
| SA1566 | ispA | 878 | 0.9328809 | 0.922238 | 0.9419005 |
| SA1567 |  | 227 | 0.5026178 | 0.4833259 | 0.5208334 |
| SA1570 |  | 359 | 0.6686277 | 0.6480728 | 0.687615 |
| SA1571 | accC | 1352 | 0.9843864 | 0.9804145 | 0.9874976 |
| SA1572 | accB | 461 | 0.7578819 | 0.7384289 | 0.7755497 |
| SA1573 |  | 1017 | 0.9562358 | 0.9481009 | 0.9629726 |
| SA1574 |  | 338 | 0.6465111 | 0.6259037 | 0.6656136 |
| SA1575 |  | 587 | 0.8356876 | 0.8186965 | 0.8507999 |
| SA1576 |  | 1043 | 0.9596003 | 0.9518814 | 0.9659649 |
| SA1577 |  | 1844 | 0.9965636 | 0.9953188 | 0.9974621 |
| SA1578 |  | 1355 | 0.9845299 | 0.9805847 | 0.9876185 |
| SA1579 |  | 2492 | 0.999532 | 0.9992893 | 0.9996893 |
| SA1580 |  | 380 | 0.6893605 | 0.6689282 | 0.7081689 |
| SA1581 |  | 257 | 0.5464708 | 0.5265046 | 0.5652295 |
| SA1582 |  | 1052 | 0.9607036 | 0.9531249 | 0.9669433 |
| SA1583 |  | 1088 | 0.9648236 | 0.9577855 | 0.9705837 |
| SA1584 |  | 299 | 0.6014469 | 0.5809609 | 0.6205601 |
| SA1585 |  | 317 | 0.6229185 | 0.602338 | 0.6420625 |
| SA1586 |  | 281 | 0.5787526 | 0.5584345 | 0.5977659 |
| SA1587 | efp | 554 | 0.8181289 | 0.8004292 | 0.8339579 |
| SA1590 |  | 215 | 0.4839115 | 0.4649714 | 0.5018306 |
| SA1591 |  | 827 | 0.9214782 | 0.9098015 | 0.9314579 |
| SA1596 | aroK | 521 | 0.7986937 | 0.7803212 | 0.8152148 |
| SA1597 |  | 494 | 0.7812572 | 0.7623713 | 0.7983162 |
| SA1598 |  | 443 | 0.7440953 | 0.7243675 | 0.7620662 |
| SA1599 | comGC | 308 | 0.6123313 | 0.5917894 | 0.6314681 |
| SA1601 | gspE | 971 | 0.9495824 | 0.9406699 | 0.9570196 |
| SA1602 |  | 620 | 0.8515512 | 0.8352918 | 0.8659336 |
| SA1603 |  | 326 | 0.6332166 | 0.6126141 | 0.6523524 |

TABLE I-continued

| SANUMBER | GENE_NAME | SIZE | PROBABILITY | LOWER | UPPER |
|---|---|---|---|---|---|
| SA1604 | glkA | 983 | 0.9514098 | 0.9427053 | 0.9586591 |
| SA1605 | | 200 | 0.4595361 | 0.4411085 | 0.4770137 |
| SA1608 | rpmG | 146 | 0.3618545 | 0.3460432 | 0.3769858 |
| SA1610 | sodA | 596 | 0.840175 | 0.8233816 | 0.8550891 |
| SA1611 | | 407 | 0.7141223 | 0.6939366 | 0.7326207 |
| SA1613 | | 782 | 0.9098184 | 0.8971864 | 0.9206956 |
| SA1617 | | 674 | 0.8742744 | 0.8592354 | 0.8874586 |
| SA1618 | rpoD | 1103 | 0.9664101 | 0.9595879 | 0.9719796 |
| SA1619 | dnaG | 1796 | 0.9960167 | 0.9946173 | 0.9970349 |
| SA1620 | | 815 | 0.918525 | 0.9065973 | 0.9287396 |
| SA1622 | glyS | 1388 | 0.9860234 | 0.9823619 | 0.9888744 |
| SA1623 | | 749 | 0.9001814 | 0.8868274 | 0.9117436 |
| SA1625 | cdd | 401 | 0.7087961 | 0.6885477 | 0.7273704 |
| SA1626 | | 341 | 0.6497588 | 0.6291542 | 0.6688491 |
| SA1632 | rpsU | 173 | 0.4127227 | 0.3954416 | 0.4291866 |
| SA1634 | | 749 | 0.9001814 | 0.8868274 | 0.9117436 |
| SA1635 | prmA | 935 | 0.9436772 | 0.9341196 | 0.9517005 |
| SA1637 | dnaK | 1829 | 0.9964013 | 0.99511 | 0.9973356 |
| SA1639 | hrcA | 974 | 0.9500456 | 0.9411854 | 0.9574355 |
| SA1643 | | 971 | 0.9495824 | 0.9406699 | 0.9570196 |
| SA1644 | | 2144 | 0.9986346 | 0.9980441 | 0.9990401 |
| SA1645 | | 428 | 0.7320087 | 0.7120741 | 0.7502133 |
| SA1646 | comEA | 683 | 0.8777079 | 0.8628729 | 0.8906939 |
| SA1648 | | 350 | 0.6593238 | 0.6387373 | 0.6783689 |
| SA1649 | | 581 | 0.8326263 | 0.8155043 | 0.8478702 |
| SA1650 | | 566 | 0.824721 | 0.8072756 | 0.8402917 |
| SA1651 | | 287 | 0.5864574 | 0.5660748 | 0.6055122 |
| SA1653 | | 1097 | 0.9657843 | 0.9588764 | 0.9714294 |
| SA1654 | | 524 | 0.8005432 | 0.78223 | 0.8170027 |
| SA1655 | pfs | 683 | 0.8777079 | 0.8628729 | 0.8906939 |
| SA1656 | | 266 | 0.5588567 | 0.5387403 | 0.5777282 |
| SA1657 | | 701 | 0.8842963 | 0.8698684 | 0.8968882 |
| SA1658 | | 1217 | 0.976347 | 0.970994 | 0.9806352 |
| SA1664 | | 731 | 0.8944976 | 0.8807435 | 0.9064417 |
| SA1668 | | 920 | 0.941017 | 0.9311813 | 0.9492945 |
| SA1669 | | 635 | 0.8582463 | 0.8423243 | 0.8722953 |
| SA1670 | | 305 | 0.6087366 | 0.5882113 | 0.6278674 |
| SA1671 | | 425 | 0.7295237 | 0.7095503 | 0.7477728 |
| SA1672 | | 257 | 0.5464708 | 0.5265046 | 0.5652295 |
| SA1673 | alaS | 2627 | 0.999691 | 0.9995201 | 0.9997994 |
| SA1675 | | 665 | 0.8707444 | 0.8555013 | 0.8841275 |
| SA1676 | trmU | 1115 | 0.9676276 | 0.9609743 | 0.9730485 |
| SA1677 | | 1139 | 0.9699319 | 0.963606 | 0.9750654 |
| SA1679 | | 143 | 0.3559372 | 0.3403112 | 0.3708987 |
| SA1680 | | 179 | 0.4234643 | 0.405902 | 0.4401795 |
| SA1681 | | 419 | 0.7244844 | 0.7044363 | 0.74282 |
| SA1683 | moeB | 770 | 0.9064267 | 0.893534 | 0.9175506 |
| SA1684 | | 125 | 0.3192633 | 0.3048482 | 0.3331066 |
| SA1685 | aspS | 1763 | 0.995591 | 0.994075 | 0.9967002 |
| SA1686 | hisS | 1259 | 0.9792142 | 0.97433 | 0.9830996 |
| SA1693 | yajC | 257 | 0.5464708 | 0.5265046 | 0.5652295 |
| SA1694 | tgt | 1136 | 0.9696531 | 0.963287 | 0.9748218 |
| SA1699 | obg | 1289 | 0.9810468 | 0.9764752 | 0.9846655 |
| SA1700 | rpmA | 281 | 0.5787526 | 0.5584345 | 0.5977659 |
| SA1701 | | 317 | 0.6229185 | 0.602338 | 0.6420625 |
| SA1702 | rplU | 305 | 0.6087366 | 0.5882113 | 0.6278674 |
| SA1706 | | 281 | 0.5787526 | 0.5584345 | 0.5977659 |
| SA1707 | radC | 683 | 0.8777079 | 0.8628729 | 0.8906939 |
| SA1708 | | 704 | 0.8853593 | 0.8709991 | 0.8978859 |
| SA1709 | | 1268 | 0.9797819 | 0.9749933 | 0.9835855 |
| SA1710 | valS | 2627 | 0.999691 | 0.9995201 | 0.9997994 |
| SA1713 | | 98 | 0.2602999 | 0.2480474 | 0.2721192 |
| SA1715 | hemB | 971 | 0.9495824 | 0.9406699 | 0.9570196 |
| SA1716 | | 665 | 0.8707444 | 0.8555013 | 0.8841275 |
| SA1719 | hemA | 1343 | 0.983948 | 0.979895 | 0.9871275 |
| SA1720 | | 587 | 0.8356876 | 0.8186965 | 0.8507999 |
| SA1724 | | 605 | 0.8445398 | 0.8279457 | 0.8592549 |
| SA1725 | rplT | 353 | 0.6624538 | 0.6418764 | 0.681481 |
| SA1726 | rpmI | 197 | 0.4545246 | 0.4362098 | 0.4719039 |
| SA1727 | infC | 524 | 0.8005432 | 0.78223 | 0.8170027 |
| SA1729 | thrS | 1934 | 0.9973947 | 0.9963971 | 0.9981042 |
| SA1730 | | 119 | 0.3065803 | 0.2926085 | 0.3200112 |
| SA1731 | dnaI | 917 | 0.9404701 | 0.9305781 | 0.948799 |
| SA1732 | | 1397 | 0.9864051 | 0.9828177 | 0.9891943 |
| SA1734 | gap | 1022 | 0.9569039 | 0.9488503 | 0.9635678 |
| SA1735 | | 620 | 0.8515512 | 0.8352918 | 0.8659336 |
| SA1736 | fpg | 869 | 0.9309965 | 0.9201752 | 0.9401808 |
| SA1741 | icd | 1265 | 0.9795944 | 0.9747741 | 0.9834251 |

TABLE I-continued

| SANUMBER | GENE_NAME | SIZE | PROBABILITY | LOWER | UPPER |
|---|---|---|---|---|---|
| SA1747 | accA | 941 | 0.9447074 | 0.9352595 | 0.9526307 |
| SA1749 | | 1226 | 0.976993 | 0.9717436 | 0.9811919 |
| SA1750 | dnaE | 3194 | 0.999946 | 0.9999078 | 0.9999681 |
| SA1755 | | 140 | 0.3499651 | 0.3345289 | 0.3647521 |
| SA1757 | | 95 | 0.2534409 | 0.2414564 | 0.2650075 |
| SA1759 | | 497 | 0.7832669 | 0.7644361 | 0.8002676 |
| SA1761 | | 944 | 0.9452154 | 0.9358221 | 0.953089 |
| SA1762 | soi8 | 491 | 0.7792289 | 0.7602885 | 0.7963456 |
| SA1765 | | 1136 | 0.9696531 | 0.963287 | 0.9748218 |
| SA1766 | | 137 | 0.3439375 | 0.3286959 | 0.3585455 |
| SA1768 | | 461 | 0.7578819 | 0.7384289 | 0.7755497 |
| SA1769 | rpsD | 599 | 0.8416434 | 0.8249163 | 0.8564912 |
| SA1770 | | 740 | 0.8973789 | 0.8838253 | 0.9091313 |
| SA1776 | | 614 | 0.8487854 | 0.8323918 | 0.863301 |
| SA1778 | tyrS | 1259 | 0.9792142 | 0.97433 | 0.9830996 |
| SA1779 | | 902 | 0.9376584 | 0.9274818 | 0.9462484 |
| SA1780 | | 89 | 0.2395316 | 0.2281006 | 0.250575 |
| SA1783 | acs | 1703 | 0.9946972 | 0.9929451 | 0.9959918 |
| SA1789 | | 488 | 0.7771817 | 0.7581873 | 0.7943558 |
| SA1790 | murC | 1310 | 0.9822327 | 0.9778693 | 0.9856744 |
| SA1792 | | 593 | 0.838693 | 0.8218335 | 0.8536732 |
| SA1793 | | 854 | 0.9277374 | 0.9166149 | 0.9372009 |
| SA1794 | | 308 | 0.6123313 | 0.5917894 | 0.6314681 |
| SA1797 | | 839 | 0.9243243 | 0.9128959 | 0.9340725 |
| SA1798 | | 641 | 0.8608391 | 0.8450525 | 0.8747547 |
| SA1799 | | 722 | 0.8915355 | 0.8775801 | 0.9036726 |
| SA1802 | | 419 | 0.7244844 | 0.7044363 | 0.74282 |
| SA1804 | | 1658 | 0.9939097 | 0.9919584 | 0.9953625 |
| SA1807 | | 308 | 0.6123313 | 0.5917894 | 0.6314681 |
| SA1808 | leuS | 2414 | 0.999405 | 0.9991083 | 0.9995999 |
| SA1811 | | 560 | 0.8214554 | 0.8038822 | 0.8371556 |
| SA1812 | ret | 398 | 0.7060958 | 0.6858177 | 0.7247066 |
| SA1814 | | 824 | 0.9207501 | 0.9090109 | 0.9307882 |
| SA1815 | | 116 | 0.3001504 | 0.2864081 | 0.3133675 |
| SA1817 | ribH | 461 | 0.7578819 | 0.7384289 | 0.7755497 |
| SA1820 | ribD | 1001 | 0.9540276 | 0.9456282 | 0.9610018 |
| SA1824 | | 392 | 0.70062 | 0.6802859 | 0.7193009 |
| SA1826 | | 221 | 0.493351 | 0.4742287 | 0.5114244 |
| SA1827 | | 545 | 0.8130225 | 0.7951352 | 0.8290433 |
| SA1828 | | 440 | 0.7417224 | 0.7219516 | 0.7597415 |
| SA1830 | | 632 | 0.8569319 | 0.8409423 | 0.8710476 |
| SA1831 | | 710 | 0.8874561 | 0.8732312 | 0.8998524 |
| SA1832 | crcB | 362 | 0.6716721 | 0.6511307 | 0.6906376 |
| SA1834 | | 1606 | 0.9928531 | 0.9906451 | 0.9945112 |
| SA1836 | | 908 | 0.9387987 | 0.9287366 | 0.9472836 |
| SA1837 | metK | 1190 | 0.9742983 | 0.9686239 | 0.9788643 |
| SA1840 | | 767 | 0.9055591 | 0.8926008 | 0.916745 |
| SA1841 | | 530 | 0.8041914 | 0.785998 | 0.8205269 |
| SA1842 | | 254 | 0.5422654 | 0.5223543 | 0.5609816 |
| SA1843 | menC | 998 | 0.9536013 | 0.9451516 | 0.9606208 |
| SA1844 | menE | 1475 | 0.9893056 | 0.9863057 | 0.991608 |
| SA1848 | | 623 | 0.852915 | 0.836723 | 0.8672308 |
| SA1849 | | 341 | 0.6497588 | 0.6291542 | 0.6688491 |
| SA1852 | | 182 | 0.4287612 | 0.4110641 | 0.4455962 |
| SA1853 | | 173 | 0.4127227 | 0.3954416 | 0.4291866 |
| SA1856 | | 98 | 0.2602999 | 0.2480474 | 0.2721192 |
| SA1857 | | 374 | 0.6835729 | 0.6630989 | 0.7024384 |
| SA1858 | | 557 | 0.8197998 | 0.8021632 | 0.8355645 |
| SA1859 | | 3047 | 0.9999151 | 0.9998586 | 0.9999486 |
| SA1860 | | 227 | 0.5026178 | 0.4833259 | 0.5208334 |
| SA1861 | hsdS | 1196 | 0.9747684 | 0.9691668 | 0.9792713 |
| SA1863 | | 131 | 0.3317143 | 0.3168761 | 0.3459497 |
| SA1865 | | 713 | 0.8884901 | 0.8743327 | 0.9008214 |
| SA1866 | | 716 | 0.8895146 | 0.8754246 | 0.901781 |
| SA1869 | | 713 | 0.8884901 | 0.8743327 | 0.9008214 |
| SA1870 | | 563 | 0.8230957 | 0.8055863 | 0.8387312 |
| SA1871 | epiG | 695 | 0.8821406 | 0.8675771 | 0.8948634 |
| SA1873 | epiF | 689 | 0.8799447 | 0.8652455 | 0.8927989 |
| SA1876 | epiC | 1241 | 0.9780306 | 0.97295 | 0.9820844 |
| SA1879 | | 1316 | 0.9825577 | 0.9782522 | 0.9859503 |
| SA1884 | | 113 | 0.293661 | 0.2801533 | 0.3066588 |
| SA1885 | | 551 | 0.8164424 | 0.7986799 | 0.8323356 |
| SA1886 | | 224 | 0.4980058 | 0.4787972 | 0.5161518 |
| SA1887 | | 1397 | 0.9864051 | 0.9828177 | 0.9891943 |
| SA1889 | hemE | 1034 | 0.958466 | 0.950605 | 0.9649575 |
| SA1890 | | 107 | 0.280501 | 0.2674788 | 0.2930441 |
| SA1894 | | 419 | 0.7244844 | 0.7044363 | 0.74282 |
| SA1895 | | 362 | 0.6716721 | 0.6511307 | 0.6906376 |

TABLE I-continued

| SANUMBER | GENE_NAME | SIZE | PROBABILITY | LOWER | UPPER |
|---|---|---|---|---|---|
| SA1896 |  | 554 | 0.8181289 | 0.8004292 | 0.8339579 |
| SA1897 |  | 959 | 0.9476862 | 0.9385623 | 0.9553151 |
| SA1898 | cbf1 | 938 | 0.9441946 | 0.9346921 | 0.9521679 |
| SA1901 |  | 95 | 0.2534409 | 0.2414564 | 0.2650075 |
| SA1902 |  | 341 | 0.6497588 | 0.6291542 | 0.6688491 |
| SA1904 |  | 461 | 0.7578819 | 0.7384289 | 0.7755497 |
| SA1905 | vraR | 620 | 0.8515512 | 0.8352918 | 0.8659336 |
| SA1907 |  | 818 | 0.9192736 | 0.9074089 | 0.9294291 |
| SA1909 |  | 392 | 0.70062 | 0.6802859 | 0.7193009 |
| SA1910 |  | 359 | 0.6686277 | 0.6480728 | 0.687615 |
| SA1911 |  | 149 | 0.3677175 | 0.3517255 | 0.383014 |
| SA1912 |  | 596 | 0.840175 | 0.8233816 | 0.8550891 |
| SA1913 |  | 467 | 0.7623104 | 0.7429547 | 0.7798722 |
| SA1915 |  | 725 | 0.892532 | 0.8786438 | 0.9046046 |
| SA1918 |  | 1316 | 0.9825577 | 0.9782522 | 0.9859503 |
| SA1919 |  | 443 | 0.7440953 | 0.7243675 | 0.7620662 |
| SA1923 |  | 1091 | 0.9651468 | 0.9581523 | 0.9708684 |
| SA1925 |  | 539 | 0.8095389 | 0.7915281 | 0.8256863 |
| SA1928 |  | 833 | 0.9229144 | 0.9113622 | 0.9327779 |
| SA1930 |  | 287 | 0.5864574 | 0.5660748 | 0.6055122 |
| SA1934 |  | 158 | 0.384985 | 0.3684777 | 0.400751 |
| SA1938 |  | 203 | 0.4645016 | 0.4459648 | 0.482074 |
| SA1940 |  | 272 | 0.5669254 | 0.5467212 | 0.5858603 |
| SA1945 |  | 383 | 0.6922144 | 0.6718049 | 0.7109926 |
| SA1946 | map | 755 | 0.9020072 | 0.8887856 | 0.9134432 |
| SA1950 | cobQ | 728 | 0.8935193 | 0.8796982 | 0.9055276 |
| SA1952 |  | 497 | 0.7832669 | 0.7644361 | 0.8002676 |
| SA1953 |  | 89 | 0.2395316 | 0.2281006 | 0.250575 |
| SA1958 |  | 944 | 0.9452154 | 0.9358221 | 0.953089 |
| SA1959 |  | 143 | 0.3559372 | 0.3403112 | 0.3708987 |
| SA1961 | gatA | 1454 | 0.9885919 | 0.985443 | 0.9910169 |
| SA1962 | gatC | 299 | 0.6014469 | 0.5809609 | 0.6205601 |
| SA1964 |  | 1196 | 0.9747684 | 0.9691668 | 0.9792713 |
| SA1965 | ligA | 2000 | 0.9978735 | 0.9970265 | 0.9984693 |
| SA1971 |  | 323 | 0.6298155 | 0.6092186 | 0.6489558 |
| SA1972 |  | 170 | 0.4072771 | 0.3901425 | 0.4236096 |
| SA1974 | nadE | 818 | 0.9192736 | 0.9074089 | 0.9294291 |
| SA1975 |  | 1439 | 0.9880531 | 0.9847938 | 0.9905694 |
| SA1982 | ppaC | 926 | 0.9420958 | 0.9323721 | 0.9502709 |
| SA1983 |  | 170 | 0.4072771 | 0.3901425 | 0.4236096 |
| SA1987 | ccoS | 170 | 0.4072771 | 0.3901425 | 0.4236096 |
| SA1990 |  | 479 | 0.7709258 | 0.7517728 | 0.7882691 |
| SA1992 |  | 560 | 0.8214554 | 0.8038822 | 0.8371556 |
| SA1994 |  | 869 | 0.9309965 | 0.9201752 | 0.9401808 |
| SA1998 |  | 173 | 0.4127227 | 0.3954416 | 0.4291866 |
| SA1999 |  | 95 | 0.2534409 | 0.2414564 | 0.2650075 |
| SA2005 |  | 140 | 0.3499651 | 0.3345289 | 0.3647521 |
| SA2006 | lukM | 1052 | 0.9607036 | 0.9531249 | 0.9669433 |
| SA2010 |  | 908 | 0.9387987 | 0.9287366 | 0.9472836 |
| SA2011 |  | 1304 | 0.9819017 | 0.9774797 | 0.9853931 |
| SA2012 |  | 440 | 0.7417224 | 0.7219516 | 0.7597415 |
| SA2014 |  | 587 | 0.8356876 | 0.8186965 | 0.8507999 |
| SA2016 | groEL | 1613 | 0.9930054 | 0.9908337 | 0.9946343 |
| SA2017 | groES | 281 | 0.5787526 | 0.5584345 | 0.5977659 |
| SA2018 |  | 740 | 0.8973789 | 0.8838253 | 0.9091313 |
| SA2021 |  | 782 | 0.9098184 | 0.8971864 | 0.9206956 |
| SA2022 | hld | 131 | 0.3317143 | 0.3168761 | 0.3459497 |
| SA2024 | agrD | 137 | 0.3439375 | 0.3286959 | 0.3585455 |
| SA2030 | scrR | 947 | 0.9457187 | 0.9363797 | 0.9535429 |
| SA2031 | amt | 1247 | 0.9784325 | 0.9734181 | 0.9824294 |
| SA2032 |  | 122 | 0.312951 | 0.298755 | 0.3265907 |
| SA2033 |  | 221 | 0.493351 | 0.4742287 | 0.5114244 |
| SA2034 |  | 983 | 0.9514098 | 0.9427053 | 0.9586591 |
| SA2038 | gcp | 1022 | 0.9569039 | 0.9488503 | 0.9635678 |
| SA2040 |  | 659 | 0.8683362 | 0.8529571 | 0.8818522 |
| SA2041 |  | 431 | 0.7344708 | 0.7145759 | 0.7526302 |
| SA2044 | ilvN | 251 | 0.538021 | 0.5181676 | 0.5566922 |
| SA2047 | leuB | 1043 | 0.9596003 | 0.9518814 | 0.9659649 |
| SA2054 | sigB | 767 | 0.9055591 | 0.8926008 | 0.916745 |
| SA2055 | rsbW | 506 | 0.7891858 | 0.7705234 | 0.8060095 |
| SA2056 | rsbV | 323 | 0.6298155 | 0.6092186 | 0.6489558 |
| SA2057 | rsbU | 998 | 0.9536013 | 0.9451516 | 0.9606208 |
| SA2061 | acpS | 356 | 0.665555 | 0.6449881 | 0.6845629 |
| SA2069 |  | 107 | 0.280501 | 0.2674788 | 0.2930441 |
| SA2073 | murF | 1355 | 0.9845299 | 0.9805847 | 0.9876185 |
| SA2074 |  | 1067 | 0.9624759 | 0.9551263 | 0.9685119 |
| SA2076 |  | 134 | 0.3378541 | 0.3228118 | 0.3522782 |
| SA2077 |  | 206 | 0.4694214 | 0.4507788 | 0.4870854 |

TABLE I-continued

| SANUMBER | GENE_NAME | SIZE | PROBABILITY | LOWER | UPPER |
|---|---|---|---|---|---|
| SA2079 | cls | 1481 | 0.9895013 | 0.9865426 | 0.9917696 |
| SA2080 | | 644 | 0.8621176 | 0.8463989 | 0.8759666 |
| SA2081 | | 89 | 0.2395316 | 0.2281006 | 0.250575 |
| SA2082 | | 869 | 0.9309965 | 0.9201752 | 0.9401808 |
| SA2083 | thiE | 638 | 0.8595487 | 0.8436944 | 0.873531 |
| SA2087 | | 128 | 0.3255175 | 0.3108884 | 0.3395593 |
| SA2089 | | 392 | 0.70062 | 0.6802859 | 0.7193009 |
| SA2090 | ywpF | 437 | 0.7393275 | 0.7195144 | 0.7573941 |
| SA2091 | fabZ | 437 | 0.7393275 | 0.7195144 | 0.7573941 |
| SA2093 | | 230 | 0.5071875 | 0.4878153 | 0.5254698 |
| SA2098 | atpH | 536 | 0.8077728 | 0.7897008 | 0.8239832 |
| SA2100 | atpE | 209 | 0.4742961 | 0.455551 | 0.4920483 |
| SA2101 | atpB | 725 | 0.892532 | 0.8786438 | 0.9046046 |
| SA2102 | | 449 | 0.7487759 | 0.7291367 | 0.7666484 |
| SA2104 | upp | 626 | 0.8542664 | 0.8381417 | 0.8685155 |
| SA2108 | | 1094 | 0.965467 | 0.9585159 | 0.9711503 |
| SA2109 | | 833 | 0.9229144 | 0.9113622 | 0.9327779 |
| SA2110 | prfA | 1073 | 0.9631622 | 0.9559027 | 0.9691183 |
| SA2112 | rpmE | 251 | 0.538021 | 0.5181676 | 0.5566922 |
| SA2115 | | 332 | 0.6399252 | 0.6193169 | 0.6590475 |
| SA2117 | fba | 857 | 0.9284013 | 0.9173395 | 0.9378085 |
| SA2121 | | 857 | 0.9284013 | 0.9173395 | 0.9378085 |
| SA2122 | | 800 | 0.9146769 | 0.9024314 | 0.9251897 |
| SA2131 | | 440 | 0.7417224 | 0.7219516 | 0.7597415 |
| SA2132 | | 410 | 0.7167488 | 0.696596 | 0.7352078 |
| SA2134 | | 236 | 0.5162013 | 0.4966774 | 0.5346084 |
| SA2135 | manA | 935 | 0.9436772 | 0.9341196 | 0.9517005 |
| SA2137 | czrA | 317 | 0.6229185 | 0.602338 | 0.6420625 |
| SA2139 | | 104 | 0.2738294 | 0.2610581 | 0.2861368 |
| SA2143 | | 824 | 0.9207501 | 0.9090109 | 0.9307882 |
| SA2145 | glmS | 1802 | 0.9960895 | 0.9947104 | 0.997092 |
| SA2152 | | 929 | 0.9426278 | 0.9329597 | 0.9507521 |
| SA2153 | | 806 | 0.9162375 | 0.9041196 | 0.9266304 |
| SA2154 | arg | 905 | 0.9382312 | 0.9281119 | 0.9467685 |
| SA2155 | | 1199 | 0.9750002 | 0.9694347 | 0.9794719 |
| SA2161 | | 1184 | 0.9738194 | 0.9680715 | 0.9784492 |
| SA2166 | | 1028 | 0.9576922 | 0.9497353 | 0.9642694 |
| SA2167 | | 980 | 0.9509593 | 0.9422031 | 0.9582552 |
| SA2168 | | 1067 | 0.9624759 | 0.9551263 | 0.9685119 |
| SA2173 | | 506 | 0.7891858 | 0.7705234 | 0.8060095 |
| SA2175 | | 533 | 0.8059904 | 0.7878575 | 0.8222635 |
| SA2182 | | 308 | 0.6123313 | 0.5917894 | 0.6314681 |
| SA2183 | lacD | 977 | 0.9505045 | 0.9416965 | 0.9578473 |
| SA2184 | lacC | 929 | 0.9426278 | 0.9329597 | 0.9507521 |
| SA2185 | lacB | 512 | 0.7930417 | 0.7744939 | 0.8097454 |
| SA2187 | | 113 | 0.293661 | 0.2801533 | 0.3066588 |
| SA2190 | | 605 | 0.8445398 | 0.8279457 | 0.8592549 |
| SA2191 | | 122 | 0.312951 | 0.298755 | 0.3265907 |
| SA2193 | | 413 | 0.7193512 | 0.6992323 | 0.7377699 |
| SA2195 | | 851 | 0.9270673 | 0.915884 | 0.9365873 |
| SA2200 | | 92 | 0.2465183 | 0.2348076 | 0.2578263 |
| SA2201 | | 596 | 0.840175 | 0.8233816 | 0.8550891 |
| SA2203 | | 1133 | 0.9693717 | 0.9629652 | 0.9745758 |
| SA2207 | rplM | 434 | 0.7369104 | 0.7170559 | 0.7550237 |
| SA2209 | | 803 | 0.9154608 | 0.9032792 | 0.9259136 |
| SA2210 | | 857 | 0.9284013 | 0.9173395 | 0.9378085 |
| SA2212 | rplQ | 365 | 0.6746886 | 0.6541621 | 0.693631 |
| SA2213 | rpoA | 941 | 0.9447074 | 0.9352595 | 0.9526307 |
| SA2214 | rpsK | 386 | 0.6950422 | 0.6746566 | 0.713789 |
| SA2215 | rpsM | 362 | 0.6716721 | 0.6511307 | 0.6906376 |
| SA2216 | rpmJ | 110 | 0.2871114 | 0.2738437 | 0.2998845 |
| SA2217 | infA | 215 | 0.4839115 | 0.4649714 | 0.5018306 |
| SA2218 | adk | 644 | 0.8621176 | 0.8463989 | 0.8759666 |
| SA2219 | secY | 1289 | 0.9810468 | 0.9764752 | 0.9846655 |
| SA2220 | rplO | 437 | 0.7393275 | 0.7195144 | 0.7573941 |
| SA2221 | rpmD | 176 | 0.4181183 | 0.4006946 | 0.4347098 |
| SA2222 | rpsE | 497 | 0.7832669 | 0.7644361 | 0.8002676 |
| SA2223 | rplR | 356 | 0.665555 | 0.6449881 | 0.6845629 |
| SA2225 | rpsH | 395 | 0.7033706 | 0.6830639 | 0.7220169 |
| SA2226 | rpsN | 182 | 0.4287612 | 0.4110641 | 0.4455962 |
| SA2227 | rplE | 488 | 0.7771817 | 0.7581873 | 0.7943558 |
| SA2228 | rplX | 314 | 0.619422 | 0.5988525 | 0.6385653 |
| SA2229 | rplN | 365 | 0.6746886 | 0.6541621 | 0.693631 |
| SA2230 | rpsQ | 260 | 0.5506376 | 0.5306188 | 0.5694363 |
| SA2231 | rpmC | 206 | 0.4694214 | 0.4507788 | 0.4870854 |
| SA2232 | rplP | 431 | 0.7344708 | 0.7145759 | 0.7526302 |
| SA2233 | rpsC | 650 | 0.8646395 | 0.8490565 | 0.8783552 |
| SA2234 | rplV | 350 | 0.6593238 | 0.6387373 | 0.6783689 |

TABLE I-continued

| SANUMBER | GENE_NAME | SIZE | PROBABILITY | LOWER | UPPER |
|---|---|---|---|---|---|
| SA2235 | rpsS | 275 | 0.5709042 | 0.5506598 | 0.5898675 |
| SA2236 | rplB | 830 | 0.9221996 | 0.9105853 | 0.9321211 |
| SA2237 | rplW | 272 | 0.5669254 | 0.5467212 | 0.5858603 |
| SA2238 | rplD | 620 | 0.8515512 | 0.8352918 | 0.8659336 |
| SA2239 | rplC | 626 | 0.8542664 | 0.8381417 | 0.8685155 |
| SA2240 | rpsJ | 305 | 0.6087366 | 0.5882113 | 0.6278674 |
| SA2244 | | 92 | 0.2465183 | 0.2348076 | 0.2578263 |
| SA2247 | | 128 | 0.3255175 | 0.3108884 | 0.3395593 |
| SA2249 | | 89 | 0.2395316 | 0.2281006 | 0.250575 |
| SA2250 | | 161 | 0.3906354 | 0.373965 | 0.4065492 |
| SA2254 | | 116 | 0.3001504 | 0.2864081 | 0.3133675 |
| SA2258 | sarV | 347 | 0.6561649 | 0.6355708 | 0.6752264 |
| SA2259 | | 167 | 0.401781 | 0.384797 | 0.417978 |
| SA2260 | | 140 | 0.3499651 | 0.3345289 | 0.3647521 |
| SA2263 | | 230 | 0.5071875 | 0.4878153 | 0.5254698 |
| SA2268 | moaB | 503 | 0.787231 | 0.7685119 | 0.8041141 |
| SA2270 | | 602 | 0.8430983 | 0.8264376 | 0.8578798 |
| SA2274 | | 767 | 0.9055591 | 0.8926008 | 0.916745 |
| SA2275 | | 551 | 0.8164424 | 0.7986799 | 0.8323356 |
| SA2277 | | 905 | 0.9382312 | 0.9281119 | 0.9467685 |
| SA2279 | | 887 | 0.934714 | 0.9242474 | 0.9435707 |
| SA2281 | ureAB | 407 | 0.7141223 | 0.6939366 | 0.7326207 |
| SA2283 | ureE | 449 | 0.7487759 | 0.7291367 | 0.7666484 |
| SA2285 | ureG | 611 | 0.8473832 | 0.8309227 | 0.8619654 |
| SA2287 | sarR | 344 | 0.6529766 | 0.6323765 | 0.6720532 |
| SA2288 | | 323 | 0.6298155 | 0.6092186 | 0.6489558 |
| SA2294 | | 419 | 0.7244844 | 0.7044363 | 0.74282 |
| SA2298 | | 635 | 0.8582463 | 0.8423243 | 0.8722953 |
| SA2299 | | 248 | 0.5337373 | 0.5139443 | 0.5523609 |
| SA2302 | | 950 | 0.9462174 | 0.9369325 | 0.9539925 |
| SA2305 | | 311 | 0.615893 | 0.5953363 | 0.635034 |
| SA2307 | | 326 | 0.6332166 | 0.6126141 | 0.6523524 |
| SA2310 | | 353 | 0.6624538 | 0.6418764 | 0.681481 |
| SA2312 | | 188 | 0.4392094 | 0.4212542 | 0.456273 |
| SA2313 | | 632 | 0.8569319 | 0.8409423 | 0.8710476 |
| SA2314 | | 914 | 0.9399181 | 0.9299696 | 0.9482988 |
| SA2315 | | 527 | 0.8023757 | 0.7841222 | 0.8187734 |
| SA2318 | | 503 | 0.787231 | 0.7685119 | 0.8041141 |
| SA2320 | | 566 | 0.824721 | 0.8072756 | 0.8402917 |
| SA2328 | | 1256 | 0.9790215 | 0.974105 | 0.9829345 |
| SA2332 | galM | 1016 | 0.956101 | 0.9479497 | 0.9628524 |
| SA2333 | | 323 | 0.6298155 | 0.6092186 | 0.6489558 |
| SA2336 | | 95 | 0.2534409 | 0.2414564 | 0.2650075 |
| SA2337 | | 161 | 0.3906354 | 0.373965 | 0.4065492 |
| SA2341 | | 1046 | 0.9599714 | 0.9522995 | 0.9662942 |
| SA2343 | | 488 | 0.7771817 | 0.7581873 | 0.7943558 |
| SA2346 | | 635 | 0.8582463 | 0.8423243 | 0.8722953 |
| SA2350 | tcaB | 1205 | 0.9754575 | 0.9699636 | 0.9798672 |
| SA2351 | | 125 | 0.3192633 | 0.3048482 | 0.3331066 |
| SA2355 | | 353 | 0.6624538 | 0.6418764 | 0.681481 |
| SA2370 | | 113 | 0.293661 | 0.2801533 | 0.3066588 |
| SA2372 | | 89 | 0.2395316 | 0.2281006 | 0.250575 |
| SA2376 | | 1439 | 0.9880531 | 0.9847938 | 0.9905694 |
| SA2377 | | 380 | 0.6893605 | 0.6689282 | 0.7081689 |
| SA2379 | | 419 | 0.7244844 | 0.7044363 | 0.74282 |
| SA2380 | | 119 | 0.3065803 | 0.2926085 | 0.3200112 |
| SA2381 | | 353 | 0.6624538 | 0.6418764 | 0.681481 |
| SA2391 | | 449 | 0.7487759 | 0.7291367 | 0.7666484 |
| SA2393 | narJ | 587 | 0.8356876 | 0.8186965 | 0.8507999 |
| SA2394 | narH | 1556 | 0.9916646 | 0.9891805 | 0.9935456 |
| SA2397 | nirD | 311 | 0.615893 | 0.5953363 | 0.635034 |
| SA2402 | | 464 | 0.7601063 | 0.7407017 | 0.7777215 |
| SA2406 | | 95 | 0.2534409 | 0.2414564 | 0.2650075 |
| SA2408 | | 359 | 0.6686277 | 0.6480728 | 0.687615 |
| SA2414 | | 101 | 0.2670958 | 0.2545811 | 0.2791621 |
| SA2415 | gpm | 683 | 0.8777079 | 0.8628729 | 0.8906939 |
| SA2416 | | 863 | 0.9297108 | 0.9187697 | 0.9390062 |
| SA2417 | | 101 | 0.2670958 | 0.2545811 | 0.2791621 |
| SA2420 | | 122 | 0.312951 | 0.298755 | 0.3265907 |
| SA2424 | bioW | 689 | 0.8799447 | 0.8652455 | 0.8927989 |
| SA2432 | | 104 | 0.2738294 | 0.2610581 | 0.2861368 |
| SA2433 | | 104 | 0.2738294 | 0.2610581 | 0.2861368 |
| SA2440 | | 803 | 0.9154608 | 0.9032792 | 0.9259136 |
| SA2444 | | 101 | 0.2670958 | 0.2545811 | 0.2791621 |
| SA2447 | | 194 | 0.4494666 | 0.431268 | 0.4667442 |
| SA2454 | | 116 | 0.3001504 | 0.2864081 | 0.3133675 |
| SA2455 | | 137 | 0.3439375 | 0.3286959 | 0.3585455 |
| SA2457 | | 167 | 0.401781 | 0.384797 | 0.417978 |

TABLE I-continued

| SANUMBER | GENE_NAME | SIZE | PROBABILITY | LOWER | UPPER |
|---|---|---|---|---|---|
| SA2463 | | 1073 | 0.9631622 | 0.9559027 | 0.9691183 |
| SA2465 | | 254 | 0.5422654 | 0.5223543 | 0.5609816 |
| SA2468 | | 95 | 0.2534409 | 0.2414564 | 0.2650075 |
| SA2481 | | 362 | 0.6716721 | 0.6511307 | 0.6906376 |
| SA2484 | | 419 | 0.7244844 | 0.7044363 | 0.74282 |
| SA2485 | | 416 | 0.7219296 | 0.7018457 | 0.7403072 |
| SA2486 | | 416 | 0.7219296 | 0.7018457 | 0.7403072 |
| SA2492 | | 119 | 0.3065803 | 0.2926085 | 0.3200112 |
| SA2494 | | 284 | 0.5826228 | 0.5622713 | 0.6016579 |
| SA2495 | | 323 | 0.6298155 | 0.6092186 | 0.6489558 |
| SA2498 | | 698 | 0.8832234 | 0.8687278 | 0.8958807 |
| SA2500 | | 389 | 0.697844 | 0.6774835 | 0.7165584 |
| SA2502 | | 263 | 0.5547661 | 0.5346972 | 0.5736024 |
| SA2503 | | 305 | 0.6087366 | 0.5882113 | 0.6278674 |
| SA2506 | sarT | 356 | 0.665555 | 0.6449881 | 0.6845629 |
| SA2507 | sarU | 740 | 0.8973789 | 0.8838253 | 0.9091313 |
| SA2510 | | 119 | 0.3065803 | 0.2926085 | 0.3200112 |
| SA2512 | | 98 | 0.2602999 | 0.2480474 | 0.2721192 |
| SA2516 | gntR | 677 | 0.8754295 | 0.8604585 | 0.8885475 |
| SA2524 | | 461 | 0.7578819 | 0.7384289 | 0.7755497 |
| SA2526 | | 461 | 0.7578819 | 0.7384289 | 0.7755497 |
| SA2530 | | 869 | 0.9309965 | 0.9201752 | 0.9401808 |
| SA2542 | | 167 | 0.401781 | 0.384797 | 0.417978 |
| SA2543 | | 95 | 0.2534409 | 0.2414564 | 0.2650075 |
| SA2547 | | 200 | 0.4595361 | 0.4411085 | 0.4770137 |
| SA2549 | | 965 | 0.948643 | 0.9396253 | 0.9561756 |
| SA2551 | | 407 | 0.7141223 | 0.6939366 | 0.7326207 |
| SA2557 | | 428 | 0.7320087 | 0.7120741 | 0.7502133 |
| SA2558 | | 131 | 0.3317143 | 0.3168761 | 0.3459497 |
| SA2565 | | 224 | 0.4980058 | 0.4787972 | 0.5161518 |
| SA2568 | | 164 | 0.3962339 | 0.3794046 | 0.4122914 |
| SA2571 | | 188 | 0.4392094 | 0.4212542 | 0.456273 |
| SA2578 | | 1124 | 0.9685117 | 0.9619828 | 0.9738233 |
| SA2579 | | 1370 | 0.9852276 | 0.9814137 | 0.9882061 |
| SA2581 | | 764 | 0.9046833 | 0.8916595 | 0.9159316 |
| SA2583 | | 485 | 0.7751156 | 0.7560678 | 0.7923466 |
| SA2586 | | 200 | 0.4595361 | 0.4411085 | 0.4770137 |
| SA2595 | | 104 | 0.2738294 | 0.2610581 | 0.2861368 |
| SA2601 | | 293 | 0.5940213 | 0.5735828 | 0.6131093 |
| SA2602 | | 365 | 0.6746886 | 0.6541621 | 0.693631 |
| SA2604 | | 122 | 0.312951 | 0.298755 | 0.3265907 |
| SA2605 | | 806 | 0.9162375 | 0.9041196 | 0.9266304 |
| SA2608 | | 719 | 0.8905297 | 0.876507 | 0.9027314 |
| SA2609 | | 446 | 0.7464464 | 0.7267625 | 0.7643685 |
| SA2611 | | 95 | 0.2534409 | 0.2414564 | 0.2650075 |
| SA2614 | panC | 848 | 0.926391 | 0.9151468 | 0.9359677 |
| SA2618 | ldh | 956 | 0.9472011 | 0.9380237 | 0.9548785 |
| SA2621 | | 413 | 0.7193512 | 0.6992323 | 0.7377699 |
| SA2622 | fda | 887 | 0.934714 | 0.9242474 | 0.9435707 |
| SA2625 | | 440 | 0.7417224 | 0.7219516 | 0.7597415 |
| SA2626 | | 209 | 0.4742961 | 0.455551 | 0.4920483 |
| SA2629 | | 92 | 0.2465183 | 0.2348076 | 0.2578263 |
| SA2630 | | 560 | 0.8214554 | 0.8038822 | 0.8371556 |
| SA2632 | cudT | 1619 | 0.9931333 | 0.9909923 | 0.9947377 |
| SA2633 | | 107 | 0.280501 | 0.2674788 | 0.2930441 |
| SA2637 | | 92 | 0.2465183 | 0.2348076 | 0.2578263 |
| SA2640 | | 89 | 0.2395316 | 0.2281006 | 0.250575 |
| SA2641 | gpxA | 494 | 0.7812572 | 0.7623713 | 0.7983162 |
| SA2642 | | 110 | 0.2871114 | 0.2738437 | 0.2998845 |
| SA2645 | | 884 | 0.9341086 | 0.9235835 | 0.9430194 |
| SA2646 | | 662 | 0.8695459 | 0.8542348 | 0.8829954 |
| SA2647 | | 197 | 0.4545246 | 0.4362098 | 0.4719039 |
| SA2649 | | 98 | 0.2602999 | 0.2480474 | 0.2721192 |
| SA2650 | | 452 | 0.751084 | 0.7314902 | 0.7689063 |
| SA2660 | | 524 | 0.8005432 | 0.78223 | 0.8170027 |
| SA2677 | | 107 | 0.280501 | 0.2674788 | 0.2930441 |
| SA2679 | | 425 | 0.7295237 | 0.7095503 | 0.7477728 |
| SA2680 | | 299 | 0.6014469 | 0.5809609 | 0.6205601 |
| SA2706 | | 494 | 0.7812572 | 0.7623713 | 0.7983162 |
| SA2717 | | 461 | 0.7578819 | 0.7384289 | 0.7755497 |
| SA2730 | | 188 | 0.4392094 | 0.4212542 | 0.456273 |
| SA2731 | cspB | 224 | 0.4980058 | 0.4787972 | 0.5161518 |
| SA2739 | rnpA | 350 | 0.6593238 | 0.6387373 | 0.6783689 |
| SA2740 | rpmH | 134 | 0.3378541 | 0.3228118 | 0.3522782 |

The invention claimed is:

1. A method for identifying a library of putative essential or important genes using a High Throughput Transposon Insertion Map (HTTIM) database, comprising:
   a) mutagenizing a *Staphylococcus* genome with a transposon such that individual cells, each containing one or more transposon insertion sites that received a transposon insertion, are isolated;
   b) sequencing said one or more transposon insertion sites in each individual cell so as to form a database of polynucleotide sequences of transposon insertion sites, or an HTTIM database, wherein said sequencing comprises amplification of a polynucleotide fragment containing one of said transposon insertion sites and the inserted transposon;
   c) comparing said polynucleotide sequences of the transposon insertion sites with the *Staphylococcus* genomic sequence to identify open reading frames in said *Staphylococcus* genomic sequence that are not disrupted by a transposon insertion; and
   d) forming a library of putative essential or important genes from said open reading frames in said *Staphylococcus* genomic sequence that are not disrupted by a transposon insertion.

2. The method of claim 1, wherein said genomic sequence is from *S. aureus*.

3. The method of claim 1, wherein said transposon inserts randomly into the target genome.

4. The method of claim 1, wherein said HTTIM database comprises polynucleotide sequences of at least about 3,000 to 6,000 transposon insertion sites.

5. The method of claim 4, wherein said HTTIM database comprises polynucleotide sequences of at least about 4,000 to 5,000 transposon insertion sites.

6. The method of claim 1, further comprising a statistical calculation for identifying putative essential genes.

7. The method of claim 6, wherein the statistical calculation utilizes a Bayessian statistical model.

8. The method of claim 1, further comprising a physical mutagenesis experiment in order to verify essential genes.

9. The method of claim 8, wherein said physical mutagenesis comprises knocking out a putative essential gene or creating a promoter swap mutant.

10. The library of putative essential or important genes identified by the method of claim 1, wherein said library comprises at most about 500 to 1850 genes.

11. The library of putative essential genes identified by the method of claim 1, wherein said library comprises at most about 1000 to 1400 genes.

12. The library of putative essential genes identified by the method of claim 1, wherein said library comprises at most about 600-625 genes.

13. The library of putative essential genes identified by the method of claim 1, wherein said library comprises at most about 530-543 genes.

14. An essential gene identified by the method of claim 8.

* * * * *

SEQUENCE LISTING

<160> NUMBER OF SEQ ID NOS: 13

<210> SEQ ID NO 1
<211> LENGTH: 31
<212> TYPE: DNA
<213> ORGANISM: artificial sequence
<220> FEATURE:
<223> OTHER INFORMATION: primer Cm194-HindF

<400> SEQUENCE: 1
tatataagct tgttacagta atattgactt t                              31

<210> SEQ ID NO 2
<211> LENGTH: 31
<212> TYPE: DNA
<213> ORGANISM: artificial sequence
<220> FEATURE:
<223> OTHER INFORMATION: primer Cm194-KpnR

<400> SEQUENCE: 2
taacgggtac cgttagtgac attagaaaac c                              31

<210> SEQ ID NO 3
<211> LENGTH: 30
<212> TYPE: DNA
<213> ORGANISM: artificial sequence
<220> FEATURE:
<223> OTHER INFORMATION: primer Erm917-HindF

<400> SEQUENCE: 3
aaataagctt tagaagcaaa cttaagagtg                                30

<210> SEQ ID NO 4
<211> LENGTH: 30
<212> TYPE: DNA
<213> ORGANISM: artificial sequence
<220> FEATURE:
<223> OTHER INFORMATION: primer Erm917-KpnR

<400> SEQUENCE: 4
cggtcgttat ggtaccattc aaatttatcc                                30

<210> SEQ ID NO 5
<211> LENGTH: 20
<212> TYPE: DNA
<213> ORGANISM: artificial sequence
<220> FEATURE:
<223> OTHER INFORMATION: primer TNErm-1R

<400> SEQUENCE: 5
ctgtttcaaa acagtagatg                                           20

<210> SEQ ID NO 6
<211> LENGTH: 19
<212> TYPE: DNA
<213> ORGANISM: artificial sequence
<220> FEATURE:
<223> OTHER INFORMATION: primer TNCm-1R2

<400> SEQUENCE: 6
gataggccta atgactggc                                            19

<210> SEQ ID NO 7
<211> LENGTH: 29
<212> TYPE: DNA

```
<213> ORGANISM: artificial sequence
<220> FEATURE:
<223> OTHER INFORMATION: primer arb-8
<220> FEATURE:
<221> NAME/KEY: misc_feature
<222> LOCATION: (1)..(29)
<223> OTHER INFORMATION: n = g, a, t, or c

<400> SEQUENCE: 7
ggccacgcgt cgactagtac nnnngatat                                       29

<210> SEQ ID NO 8
<211> LENGTH: 22
<212> TYPE: DNA
<213> ORGANISM: artificial sequence
<220> FEATURE:
<223> OTHER INFORMATION: primer TNErm-2R

<400> SEQUENCE: 8
caacatgacg aatccctcct tc                                              22

<210> SEQ ID NO 9
<211> LENGTH: 24
<212> TYPE: DNA
<213> ORGANISM: artificial sequence
<220> FEATURE:
<223> OTHER INFORMATION: primer TNCm-2R2

<400> SEQUENCE: 9
gtcggttttc taatgtcact aacg                                            24

<210> SEQ ID NO 10
<211> LENGTH: 20
<212> TYPE: DNA
<213> ORGANISM: artificial sequence
<220> FEATURE:
<223> OTHER INFORMATION: pirmer arb-tail

<400> SEQUENCE: 10
ggccacgcgt cgactagtac                                                 20

<210> SEQ ID NO 11
<211> LENGTH: 2470
<212> TYPE: DNA
<213> ORGANISM: artificial sequence
<220> FEATURE:
<223> OTHER INFORMATION: plasmid pMOD

<400> SEQUENCE: 11
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aaggcgatc ggtgcgggcc tcttcgctat     300
tacgccagct gtctcttata cacatctcaa ccatcatcga tgaattcgag ctcggtaccc    360
ggggatcctc tagagtcgac ctgcaggcat gcaagcttca gggttgagat gtgtataaga    420
gacagctgca ttaatgaatc ggccaacgcg cggggagagg cggtttgcgt attgggcgct    480
cttccgcttc ctcgctcact gactcgctgc gctcggtcgt tcggctgcgg cgagcggtat    540
cagctcactc aaaggcggta atacggttat ccacagaatc aggggataac gcaggaaaga    600
acatgtgagc aaaaggccag caaaaggcca ggaaccgtaa aaaggccgcg ttgctggcgt    660
```

| | |
|---|---:|
| ttttccatag gctccgcccc cctgacgagc atcacaaaaa tcgacgctca agtcagaggt | 720 |
| ggcgaaaccc gacaggacta taagatacc aggcgtttcc ccctggaagc tccctcgtgc | 780 |
| gctctcctgt tccgaccctg ccgcttaccg gatacctgtc cgcctttctc ccttcgggaa | 840 |
| gcgtggcgct ttctcatagc tcacgctgta ggtatctcag ttcggtgtag gtcgttcgct | 900 |
| ccaagctggg ctgtgtgcac gaaccccccg ttcagcccga ccgctgcgcc ttatccggta | 960 |
| actatcgtct tgagtccaac ccggtaagac acgacttatc gccactggca gcagccactg | 1020 |
| gtaacaggat tagcagagcg aggtatgtag gcggtgctac agagttcttg aagtggtggc | 1080 |
| ctaactacgg ctacactaga aggacagtat ttggtatctg cgctctgctg aagccagtta | 1140 |
| ccttcggaaa aagagttggt agctcttgat ccggcaaaca accaccgct ggtagcggtg | 1200 |
| gtttttttgt ttgcaagcag cagattacgc gcagaaaaaa aggatctcaa gaagatcctt | 1260 |
| tgatcttttc tacggggtct gacgctcagt ggaacgaaaa ctcacgttaa gggattttgg | 1320 |
| tcatgagatt atcaaaaagg atcttcacct agatcctttt aaattaaaaa tgaagtttta | 1380 |
| aatcaatcta agtatatat gagtaaactt ggtctgacag ttaccaatgc ttaatcagtg | 1440 |
| aggcacctat ctcagcgatc tgtctatttc gttcatccat agttgcctga ctccccgtcg | 1500 |
| tgtagataac tacgatacgg gagggcttac catctggccc cagtgctgca atgataccgc | 1560 |
| gagacccacg ctcaccggct ccagatttat cagcaataaa ccagccagcc ggaagggccg | 1620 |
| agcgcagaag tggtcctgca actttatccg cctccatcca gtctattaat tgttgccggg | 1680 |
| aagctagagt aagtagttcg ccagttaata gtttgcgcaa cgttgttgcc attgctacag | 1740 |
| gcatcgtggt gtcacgctcg tcgtttggta tggcttcatt cagctccggt tcccaacgat | 1800 |
| caaggcgagt tacatgatcc cccatgttgt gcaaaaaagc ggttagctcc ttcggtcctc | 1860 |
| cgatcgttgt cagaagtaag ttggccgcag tgttatcact catggttatg gcagcactgc | 1920 |
| ataattctct tactgtcatg ccatccgtaa gatgcttttc tgtgactggt gagtactcaa | 1980 |
| ccaagtcatt ctgagaatag tgtatgcggc gaccgagttg ctcttgcccg gcgtcaatac | 2040 |
| gggataatac cgcgccacat agcagaactt taaaagtgct catcattgga aaacgttctt | 2100 |
| cggggcgaaa actctcaagg atcttaccgc tgttgagatc cagttcgatg taacccactc | 2160 |
| gtgcacccaa ctgatcttca gcatctttta ctttcaccag cgtttctggg tgagcaaaaa | 2220 |
| caggaaggca aaatgccgca aaaaagggaa taagggcgac acggaaatgt tgaatactca | 2280 |
| tactcttcct ttttcaatat tattgaagca tttatcaggg ttattgtctc atgagcggat | 2340 |
| acatatttga atgtatttag aaaaataaac aaataggggt tccgcgcaca tttccccgaa | 2400 |
| aagtgccacc tgacgtctaa gaaaccatta ttatcatgac attaacctat aaaaataggc | 2460 |
| gtatcacgag | 2470 |

<210> SEQ ID NO 12
<211> LENGTH: 3685
<212> TYPE: DNA
<213> ORGANISM: artificial
<220> FEATURE:
<223> OTHER INFORMATION: plasmid pMOD (Erm1)

<400> SEQUENCE: 12

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |

```
attcgccatt caggctgcgc aactgttggg aagggcgatc ggtgcgggcc tcttcgctat    300
tacgccagct gtctcttata cacatctcaa ccatcatcga tgaattcgag ctcggtaccg    360
taccattcaa atttatcctt attgtacaaa ataacagcga aatttttaaa tctattcctt    420
atcgatacaa attccccgta ggcgctaggg acctctttag ctccttggaa gctgtcagta    480
gtatacctaa taatttatct acattccctt tagtaacgtg taactttcca aatttacaaa    540
agcgactcat agaattattt cctcccgtta ataatagat aactattaaa aatagacaat     600
acttgctcat aagtaacggt acttaaattg tttactttgg cgtgtttcat tgcttgtgaa    660
actgattttt agtaaacagt tgacgatatt ctcgattgac ccattttgaa acaaagtacg    720
tatatagctt ccaatattta tctggaacat ctgtggtatg gcgggtaagt tttattaaga    780
cactgtttac ttttggttta ggatgaaagc attccgctgg cagcttaagc aattgctgaa    840
tcgagacttg agtgtgcaag agcaacccta gtgttcggtg aatatccaag gtacgcttgt    900
agaatccttc ttcaacaatc agatagatgt cagacgcatg gctttcaaaa accactttt    960 taataatttg tgtgcttaaa tggtaaggaa tattcccaac aattttatac ctctgtttgt    1020
tagggaattg aaactgtaga atatcttggt gaattaaagt gacacgaatg ttcagttta     1080 attttttctga cgataagttg aatagatgac tgtctaattc aatagacgtt acctgtttac   1140 ttatttagc cagtttcgtc gttaaatgcc ctttacctgt tccaatttcg taaacggtat     1200
cggtttcttt taaattcaat tgttttatta tttggttgag tacctttca ttcgttaaaa     1260 agttttgaga atattttata ttttgttca tgtaatcact cctgaagtga tacatctata     1320
aataaataca gaagttaaac gatttgtttg taattttagt tatctgttta aaagtcata     1380 agattagtca ctggtaggaa ttaatctaaa cgtatttatc tgcgtaatca ctgttttag     1440 tctgtttcaa aacagtagat gttttatcta cattacgcat ttggaatacc aacatgacga    1500
atccctcctt cttaattaca aatttttagc atctaattta acttcaattc ctattataca    1560
aaattttaag ataatgcact atcaacacac tcttaagttt gcttctaaag cttcagggtt    1620
gagatgtgta taagagacag ctgcattaat gaatcggcca acgcgcgggg agaggcggtt    1680
tgcgtattgg gcgctcttcc gcttcctcgc tcactgactc gctgcgctcg gtcgttcggc    1740
tgcggcgagc ggtatcagct cactcaaagg cggtaatacg gttatccaca gaatcagggg    1800
ataacgcagg aaagaacatg tgagcaaaag gccagcaaaa ggccaggaac cgtaaaaagg    1860
ccgcgttgct ggcgtttttc cataggctcc gcccccctga cgagcatcac aaaaatcgac    1920
gctcaagtca gaggtggcga aacccgacag gactataaag ataccaggcg tttccccctg    1980
gaagctccct cgtgcgctct cctgttccga ccctgccgct taccggatac ctgtccgcct    2040
ttctcccttc gggaagcgtg gcgctttctc atagctcacg ctgtaggtat ctcagttcgg    2100
tgtaggtcgt tcgctccaag ctgggctgtg tgcacgaacc ccccgttcag cccgaccgct    2160
gcgccttatc cggtaactat cgtcttgagt ccaacccggt aagacacgac ttatcgccac    2220
tggcagcagc cactggtaac aggattagca gagcgaggta tgtaggcggt gctacagagt    2280
tcttgaagtg gtggcctaac tacggctaca ctagaaggac agtatttggt atctgcgctc    2340
tgctgaagcc agttaccttc ggaaaaagag ttggtagctc ttgatccggc aaacaaacca    2400
ccgctggtag cggtggtttt tttgtttgca agcagcagat tacgcgcaga aaaaaggat     2460 ctcaagaaga tcctttgatc ttttctacgg ggtctgacgc tcagtggaac gaaaactcac    2520
gttaagggat tttggtcatg agattatcaa aaaggatctt cacctagatc cttttaaatt    2580
aaaaatgaag ttttaaatca atctaaagta tatatgagta aacttggtct gacagttacc    2640
```

| | | | | | |
|---|---|---|---|---|---|
| aatgcttaat | cagtgaggca | cctatctcag | cgatctgtct | atttcgttca | tccatagttg | 2700
| cctgactccc | cgtcgtgtag | ataactacga | tacgggaggg | cttaccatct | ggccccagtg | 2760
| ctgcaatgat | accgcgagac | ccacgctcac | cggctccaga | tttatcagca | ataaaccagc | 2820
| cagccggaag | ggccgagcgc | agaagtggtc | ctgcaacttt | atccgcctcc | atccagtcta | 2880
| ttaattgttg | ccgggaagct | agagtaagta | gttcgccagt | taatagtttg | cgcaacgttg | 2940
| ttgccattgc | tacaggcatc | gtggtgtcac | gctcgtcgtt | tggtatggct | tcattcagct | 3000
| ccggttccca | acgatcaagg | cgagttacat | gatcccccat | gttgtgcaaa | aaagcggtta | 3060
| gctccttcgg | tcctccgatc | gttgtcagaa | gtaagttggc | cgcagtgtta | tcactcatgg | 3120
| ttatggcagc | actgcataat | tctcttactg | tcatgccatc | cgtaagatgc | ttttctgtga | 3180
| ctggtgagta | ctcaaccaag | tcattctgag | aatagtgtat | gcggcgaccg | agttgctctt | 3240
| gcccggcgtc | aatacgggat | aataccgcgc | cacatagcag | aactttaaaa | gtgctcatca | 3300
| ttggaaaacg | ttcttcgggg | cgaaaactct | caaggatctt | accgctgttg | agatccagtt | 3360
| cgatgtaacc | cactcgtgca | cccaactgat | cttcagcatc | ttttactttc | accagcgttt | 3420
| ctgggtgagc | aaaaacagga | aggcaaaatg | ccgcaaaaaa | gggaataagg | gcgacacgga | 3480
| aatgttgaat | actcatactc | ttcctttttc | aatattattg | aagcatttat | cagggttatt | 3540
| gtctcatgag | cggatacata | tttgaatgta | tttagaaaaa | taaacaaata | ggggttccgc | 3600
| gcacatttcc | ccgaaaagtg | ccacctgacg | tctaagaaac | cattattatc | atgacattaa | 3660
| cctataaaaa | taggcgtatc | acgag | | | | 3685

<210> SEQ ID NO 13
<211> LENGTH: 3245
<212> TYPE: DNA
<213> ORGANISM: artificial sequence
<220> FEATURE:
<223> OTHER INFORMATION: plasmid pMOD (Cm)

<400> SEQUENCE: 13

| | | | | | |
|---|---|---|---|---|---|
| tcgcgcgttt | cggtgatgac | ggtgaaaacc | tctgacacat | gcagctcccg | gagacggtca | 60
| cagcttgtct | gtaagcggat | gccgggagca | gacaagcccg | tcagggcgcg | tcagcgggtg | 120
| ttggcgggtg | tcggggctgg | cttaactatg | cggcatcaga | gcagattgta | ctgagagtgc | 180
| accatatgcg | gtgtgaaata | ccgcacagat | gcgtaaggag | aaaataccgc | atcaggcgcc | 240
| attcgccatt | caggctgcgc | aactgttggg | aagggcgatc | ggtgcgggcc | tcttcgctat | 300
| tacgccagct | gtctcttata | cacatctcaa | ccatcatcga | tgaattcgag | ctcggtaccg | 360
| ttagtgacat | tagaaaaccg | actgtaaaaa | gtacagtcgg | cattatctca | tattataaaa | 420
| gccagtcatt | aggcctatct | gacaattcct | gaatagagtt | cataaacaat | cctgcatgat | 480
| aaccatcaca | aacagaatga | tgtacctgta | aagatagcgg | taaatatatt | gaattacctt | 540
| tattaatgaa | ttttcctgct | gtaataatgg | gtagaaggta | attactatta | ttattgatat | 600
| ttaagttaaa | cccagtaaat | gaagtccatg | gaataataga | aagagaaaaa | gcattttcag | 660
| gtataggtgt | tttgggaaac | aatttccccg | aaccattata | tttctctaca | tcagaaaggt | 720
| ataaatcata | aaactctttg | aagtcattct | tacaggagt | ccaaatacca | gagaatgttt | 780
| tagatacacc | atcaaaaatt | gtataaagtg | gctctaactt | atcccaataa | cctaactctc | 840
| cgtcgctatt | gtaaccagtt | ctaaaagctg | tatttgagtt | tatcacccctt | gtcactaaga | 900
| aaataaatgc | agggtaaaat | ttatatcctt | cttgttttat | gtttcggtat | aaaacactaa | 960
| tatcaatttc | tgtggttata | ctaaaagtcg | tttgttggtt | caaataatga | ttaaatatct | 1020

```
cttttctctt ccaattgtct aaatcaattt tattaaagtt catttgatat gcctcctaaa    1080
tttttatcta aagtgaattt aggaggctta cttgtctgct ttcttcatta gaatcaatcc    1140
ttttttaaaa gtcaatatta ctgtaacaag cttcagggtt gagatgtgta taagagacag    1200
ctgcattaat gaatcggcca acgcgcgggg agaggcggtg tgcgtattgg gcgctcttcc    1260
gcttcctcgc tcactgactc gctgcgctcg gtcgttcggc tgcggcgagc ggtatcagct    1320
cactcaaagg cggtaatacg gttatccaca gaatcagggg ataacgcagg aaagaacatg    1380
tgagcaaaag gccagcaaaa ggccaggaac cgtaaaaagg ccgcgttgct ggcgtttttc    1440
cataggctcc gcccccctga cgagcatcac aaaaatcgac gctcaagtca gaggtggcga    1500
aacccgacag gactataaag ataccaggcg tttccccctg gaagctccct cgtgcgctct    1560
cctgttccga ccctgccgct taccggatac ctgtccgcct ttctcccttc gggaagcgtg    1620
gcgctttctc atagctcacg ctgtaggtat ctcagttcgg tgtaggtcgt tcgctccaag    1680
ctgggctgtg tgcacgaacc ccccgttcag cccgaccgct gcgccttatc cggtaactat    1740
cgtcttgagt ccaacccggt aagacacgac ttatcgccac tggcagcagc cactggtaac    1800
aggattagca gagcgaggta tgtaggcggt gctacagagt tcttgaagtg gtggcctaac    1860
tacggctaca ctagaaggac agtatttggt atctgcgctc tgctgaagcc agttaccttc    1920
ggaaaaagag ttggtagctc ttgatccggc aaacaaacca ccgctggtag cggtggtttt    1980
tttgtttgca agcagcagat tacgcgcaga aaaaaggat ctcaagaaga tcctttgatc     2040
ttttctacgg ggtctgacgc tcagtggaac gaaaactcac gttaagggat tttggtcatg    2100
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacgggaggg cttaccatct ggccccagtg ctgcaatgat accgcgagac    2340
ccacgctcac cggctccaga tttatcagca ataaaccagc cagccggaag ggccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagcag aactttaaaa gtgctcatca ttggaaaacg ttcttcgggg    2880
cgaaaactct caaggatctt accgctgttg agatccagtt cgatgtaacc cactcgtgca    2940
cccaactgat cttcagcatc ttttactttc accagcgttt ctgggtgagc aaaaacagga    3000
aggcaaaatg ccgcaaaaaa gggaataagg gcgacacgga aatgttgaat actcatactc    3060
ttcctttttc aatattattg aagcatttat cagggttatt gtctcatgag cggatacata    3120
tttgaatgta tttagaaaaa taaacaaata ggggttccgc gcacatttcc ccgaaaagtg    3180
ccacctgacg tctaagaaac cattattatc atgacattaa cctataaaaa taggcgtatc    3240
acgag                                                                3245
```